United States Patent
Bruno et al.

(10) Patent No.: US 8,389,710 B2
(45) Date of Patent: *Mar. 5, 2013

(54) THERAPEUTIC NUCLEIC ACID-3'-CONJUGATES

(75) Inventors: John G. Bruno, San Antonio, TX (US); Judson C. Miner, San Antonio, TX (US)

(73) Assignee: Operational Technologies Corporation, San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/716,088

(22) Filed: Mar. 2, 2010

(65) Prior Publication Data

US 2012/0123096 A1    May 17, 2012

Related U.S. Application Data

(63) Continuation-in-part of application No. 11/735,221, filed on Apr. 13, 2007, which is a continuation-in-part of application No. 11/058,054, filed on Feb. 15, 2005, now Pat. No. 7,910,297.

(60) Provisional application No. 60/548,629, filed on Feb. 27, 2004, provisional application No. 61/156,765, filed on Mar. 2, 2009, provisional application No. 61/161,505, filed on Mar. 19, 2009.

(51) Int. Cl.
*C07H 21/04* (2006.01)

(52) U.S. Cl. .................... 536/24.5; 536/24.31; 536/24.1; 514/44

(58) Field of Classification Search .................... None
See application file for complete search history.

(56) References Cited

U.S. PATENT DOCUMENTS

| | | | |
|---|---|---|---|
| 5,270,163 A | 12/1993 | Gold et al. | |
| 5,475,096 A | 12/1995 | Gold et al. | |
| 5,573,913 A | 11/1996 | Rosemeyer et al. | |
| 6,127,119 A | 10/2000 | Stephens et al. | |
| 6,172,208 B1 | 1/2001 | Cook | |
| 6,235,886 B1 | 5/2001 | Manoharan et al. | |
| 6,566,343 B2 | 5/2003 | Biesecker et al. | |
| 6,623,926 B1 | 9/2003 | Lohse et al. | |
| 6,780,850 B1 | 8/2004 | Dougan et al. | |
| 2003/0049644 A1* | 3/2003 | Rabin et al. .................... | 435/6 |

OTHER PUBLICATIONS

Chu, Ted, C., et al.; Aptamer: Toxin Conjugates that specifically target prostate tumor cells: Cancer Research: Jun. 15, 2006: pp. 5989-5992; 66(12): American Association for Cancer Research; Austin, TX, US.

Abe, Ikuro et al.; Enzymatic formation of unnatural cytokinin analogs by adenylate isopentenyltransferase from mulberry; Science Direct: Feb. 15, 2007; pp. 795-800; Biochemical and Biophysical Research Communications 355.

Zahler, Alan M. et al.; Telomere terminal transferase activity in the hypotrichous ciliate Oxytricha nova and a model for replication of the ends of linear DNA molecules; Nucleic Acids Research; 1988; pp. 6953-6972; IRL Press Ltd.; Oxford, England.

Bell et al.,"Oligonucelotide NX1838 inhibits VEGF165-mediated cellular responses in vitro"; In vitro Cell Develop. Biol. Animal (1999) 35: 533-542.

Biesecker, et al, :Derivation of RNA Aptamer inhibitors of Human Complement C5, Immunopharm (1999) 42:219-230.

Blank, et al. "Systematic Evolution of a DNA Aptamer Binding to Rat Brain Tumor Microvessels, Selective Targeting of Endothelial Regulatory Protein Pigpen," J. Biol. Chem. (2001) 276:16464-16468.

Brody, E.N. and Gold, L., "Aptamers as Therapeutic and Diagnostic Agents," Reviews in Mol. Biotechnol. (2000), 74:5-13.

Bruno, In Vitro Selection of DNA to Chloroaromatics Using Magnetic Microbead-Based Affinity Separation and Fluorescence Detection, Biochem. Biophys. Res. Comm. (1997) 234: 117-120.

Bruno and Kiel, "In Vitro Selection of DNA Aptamers to Anthrax Spores with Electrochemiluminescence Detection,"Biosensors & Bioelectronics (1999) 14:457-464.

Bruno and Kiel, "Use of Magnetic Beads in Selection and Detection of Biotoxin Aptamers by ECL and Enzymatic Methods," Bio Techniques (2002) 32:178-183.

Dougan, et al., "Extending the Lifetime of Anticoagulant Oligodeoxynucleotide Aptamers in Blood," Nuclear Med. Biol. (2000) 27:289-297.

Drolet, et al., "Pharmacokinetics and Safety of Anti-Vascular Endothelial Growth Factor Aptamer (NX1838) Following Injection into the Vitreous Humor or Rhesus Monkeys." (2000) Pharm. Res. 17:1503-1510.

Hicke, et al., "Tenascin-C Aptamers are generated Using Tumor Cells and Purified Protein," J. Biol. Chem. (2001) 276:48644-48654.

Homann and Goringer, "Uptake and Intracellular Transport of RNA Aptamers in African Trypanosomes Suggest Therapeutic "Piggy-Back" Approach," Bioorg. Med. Chem (2001) 9:2571-2580.

Huang, et al. "Highly Specific Antiangiogenic Therapy is Effective in Suppressing Growth of Experimental Wilms Tumors," J. Pediatric Surg. (2001) 36:357-361.

Murphy, et al., "An Improved Method for the in Vitro Evolution of Aptamers and Applications in protein Detection and Purification," Nucleic Acids Res. (2003) 31:e110-e118.

Ono, T, et al., "2-Fluoro Modified Nucleic Acids: Polymerase-Directed Synthesis, Properties and Stability to Analysis by Matrix Assisted Laser Desorption/Ionization Mass Spectrometry." Nucl. Acids Res. (1997), 25:4581-4588.

Ruckman, J., et al., 2-Fluropyrimidine RNA-Based Aptamers to the 165 Amino Acid Form of Vascular Endothelial Growth Factor (VEGF 165) J. Biol. Chem. (1998) 273:20556-20567.

(Continued)

*Primary Examiner* — Kimberly Chong
(74) *Attorney, Agent, or Firm* — Winstead PC

(57) ABSTRACT

Methods are described for improvement of the serum half life of therapeutic nucleic acids by 3' conjugation to useful target proteins, or other large molecules with useful function. In one embodiment, a 3' A, C or G overhang is added to ds-DNA and the primary amines conjugated using biocompatible bifunctional linkers to proteins. The resulting nucleic acid-3' conjugates are serum nuclease-resistant and retained in vivo for long periods without rapid kidney clearance. Further, the choice of conjugate imparts additional functionality to the nucleic acid-3' conjugate.

20 Claims, 7 Drawing Sheets

OTHER PUBLICATIONS

Ulrich, et al., "In Vitro Selection of RNA Aptamers that Bind the Cell Adhesion Receptors of Trypanosome cruzi and inhibit cell invasion," J. Biol. Chem. (2002) 277:20756-20762.
Welkos, et al., "The Role of Antibodies to Bacillus Anthracis and Anthrax toxin components in Inhibiting the Early Stages of Inflection of Anthrax Spores," Microbiology (2001), 147:1677-1685.
Petrie et al. An Improved CPG Support for the Synthesis of 3' amine-tailed oligonucleotides. Bioconjugate chem. 192, vol. 3: 85-87, 1992.
Alderson, Formaldehyde-induced mutagenesis: a novel mechanism for its action; Mutation Research, 154 (1985) 101-110.
Anorbe, Perturbation of the NH2 pKa Value of Adenine in Platinum(II) Complexes: Distinct Stereochemical Internucleobase Effects; Chem. Eur. J. (2004), 10:1046-1057.
Dolan, Robust and effecient synthetic method for forming DNA microarrays; Nucleic Acids Research, 2001, vol. 29, No. 21 e107.
Gacesa; The Immobolization of Adenine Nucleotides on Polysaccharides by using Glutaraldehyde Coupling and Borohydride Reduction; Biochem. J. (1978) 175, 349-352.
Harrison, Site-Specific Methylation of Adenine in the Nuclear Genome of a Eucaryote, Tetrahymena thermophila; Molecular and Cellular Biology, Jul. 1986, p. 2364-2370.
Hayatsu, N-Sulfomethylation of guanine, adenine and cytosine with formaldehyde-bisulfite. A selective modification of guanine in DNA; Nucleic Acids Research, vol. 10 No. 20 1982.
Hopwood, The reactions of glutaraldehyde with nucleic acids; Histochemical Journal, 7 (1975), 267-276.
Kloepfer, Uptake of CdSe and CdSe/ZnS Quantum Dots into Bacteria via Purine-Dependent Mechanisms; Applied and Environmental Microbiology, May 2005, p. 2548-2557, vol. 71, No. 5.
Matsuura, Facile Synthesis of Stable and Lectin-Recognizable DNA-Carbohydrate Conjugates via Diazo Coupling, Bioconjugate Chem. 2000, 11, 202-211.
Pues, Functional Roles of the Conserved Aromatic Amino Acid Residues at Position 108; Biochemistry 1999, 38, 1426-1434.
Rall, Evidence for Cross-Linking of Cyclic AMP to Constituents of Brain Tissue by Aldehyde Fixatives: Potential Utility in Histochemical Procedures; Journal of Cyclic Nucleotide Research 8(4): 243-265 (1982).
Scavetta, Structure of Rsrl methyltransferase, a member of the N6-adenine B class of DNA methyltransferases; 3950-3961, Nucleic Acids Research, 2000, vol. 28, No. 20.
Wang, Catalytic Mechanism of Hamster Arylamine N-Acetyltransferase 2, Biochemistry 2005, 44, 11295-11306.
Yamazaki, A New Method of Chemical Modification of N6-Amino Group; Eur. J. Biochem 92, 197-207 (1978).
Zhou, Universal TA Cloning; Curr. Issues Mol. Biol. (2000) 2(1): 1-7.
Zinoviev, Phage T4 DNA [N6-Adenine] Methyltransferase, Biol Chem 379:481-488, 1998.

* cited by examiner

SEQUENCE LISTING

<160> NUMBER OF SEQ ID NOS: 381

<210> SEQ ID NO 1
<211> LENGTH: 60
<212> TYPE: DNA
<213> ORGANISM: Artificial
<220> FEATURE:
<223> OTHER INFORMATION: Synthesized Oligonucleotide Sequence

<400> SEQUENCE: 1
catccgtcac acctgctctg ctatcacatg cctgctgaag tggtgttggc tcccgtatca    60

<210> SEQ ID NO 2
<211> LENGTH: 60
<212> TYPE: DNA
<213> ORGANISM: Artificial
<220> FEATURE:

<223> OTHER INFORMATION: Synthesized Oligonucleotide Sequence

<400> SEQUENCE: 2
catccgtcac acctgctctg atcagggaag acgccaacac tggtgttggc tcccgtatca    60

<210> SEQ ID NO 3
<211> LENGTH: 62
<212> TYPE: DNA
<213> ORGANISM: Artificial
<220> FEATURE:
<223> OTHER INFORMATION: Synthesized Oligonucleotide Sequence

<400> SEQUENCE: 3
catccgtcac acctgctctg gggagggtgg cgcccgtctc ggtggtgttg gctcccgtat    60
ca    62

<210> SEQ ID NO 4
<211> LENGTH: 62
<212> TYPE: DNA
<213> ORGANISM: Artificial
<220> FEATURE:
<223> OTHER INFORMATION: Synthesized Oligonucleotide Sequence

<400> SEQUENCE: 4
catccgtcac acctgctctg ggatagggtc tcgtgctaga tgtggtgttg gctcccgtat    60
ca    62

<210> SEQ ID NO 5
<211> LENGTH: 62
<212> TYPE: DNA
<213> ORGANISM: Artificial
<220> FEATURE:
<223> OTHER INFORMATION: Synthesized Oligonucleotide Sequence

<400> SEQUENCE: 5
catccgtcac acctgctctg gaccggcgct tattcctgct tgtggtgttg gctcccgtat    60
ca    62

<210> SEQ ID NO 6
<211> LENGTH: 62
<212> TYPE: DNA
<213> ORGANISM: Artificial
<220> FEATURE:
<223> OTHER INFORMATION: Synthesized Oligonucleotide Sequence

<400> SEQUENCE: 6
catccgtcac acctgcyctg gagctgatat tggatggtcc ggtggtgttg gctcccgtat    60
ca    62

<210> SEQ ID NO 7
<211> LENGTH: 62
<212> TYPE: DNA
<213> ORGANISM: Artificial
<220> FEATURE:
<223> OTHER INFORMATION: Synthesized Oligonucleotide Sequence

<400> SEQUENCE: 7
catccgtcac acctgcycyg cccagagcag gtgtgacgga tgtggtgttg gctcccgtat    60
ca    62

<210> SEQ ID NO 8
<211> LENGTH: 62
<212> TYPE: DNA

```
<213> ORGANISM: Artificial
<220> FEATURE:
<223> OTHER INFORMATION: Synthesized Oligonucleotide Sequence

<400> SEQUENCE: 8
catccgtcac acctgcycyg ccggaccatc caatatcagc tgtggtgttg gctcccgtat      60
ca                                                                    62

<210> SEQ ID NO 9
<211> LENGTH: 60
<212> TYPE: DNA
<213> ORGANISM: Artificial
<220> FEATURE:
<223> OTHER INFORMATION: Synthesized Oligonucleotide Sequence

<400> SEQUENCE: 9
catccgtcac acctgctctg gttcgccccg gtcaaggaga gtggtgttgg ctcccgtatc      60

<210> SEQ ID NO 10
<211> LENGTH: 60
<212> TYPE: DNA
<213> ORGANISM: Artificial
<220> FEATURE:
<223> OTHER INFORMATION: Synthesized Oligonucleotide Sequence

<400> SEQUENCE: 10
gatacgggag ccaacaccac tctccttgac cggggcgaac cagagcaggt gtgacggatg      60

<210> SEQ ID NO 11
<211> LENGTH: 61
<212> TYPE: DNA
<213> ORGANISM: Artificial
<220> FEATURE:
<223> OTHER INFORMATION: Synthesized Oligonucleotide Sequence

<400> SEQUENCE: 11
catccgtcac acctgctctg gataagatca gcaacaagtt agtggtgttg gctcccgtat      60
c                                                                     61

<210> SEQ ID NO 12
<211> LENGTH: 60
<212> TYPE: DNA
<213> ORGANISM: Artificial
<220> FEATURE:
<223> OTHER INFORMATION: Synthesized Oligonucleotide Sequence

<400> SEQUENCE: 12
gatacgggag ccaacaccac taacttgttg ctgatcttat cagagcaggt gtgacggatg      60

<210> SEQ ID NO 13
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 13
atacgggagc caacaccatc atttgcaaat atgaattcca cttaaagaaa ttcaagagca      60
ggtgtgacgg at                                                         72

<210> SEQ ID NO 14
<211> LENGTH: 72
<212> TYPE: DNA
<213> ORGANISM: Artificial
<220> FEATURE:
```

<223> OTHER INFORMATION: Synthesized Oligonucleotide Sequence

<400> SEQUENCE: 14

```
atacgggagc caacaccatt aaatcaattg tgccgtgttg gtcttgtctc atcgagagca    60
ggtgtgacgg at                                                        72
```

<210> SEQ ID NO 15
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 15

```
atacgggagc caacaccatt tttattatcg gtatgatcct acgagttcct cccaagagca    60
ggtgtgacgg at                                                        72
```

<210> SEQ ID NO 16
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 16

```
atacgggagc caacaccacc gtatatctta ttatgcacag catcacgaaa gtgcagagca    60
ggtgtgacgg at                                                        72
```

<210> SEQ ID NO 17
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 17

```
atacgggagc caacaccatt aacgttaagc ggcctcactt cttttaatcc tttcagagca    60
ggtgtgacgg at                                                        72
```

<210> SEQ ID NO 18
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 18

```
atccgtcaca cctgctctaa tatagaggta ttgctcttgg acaaggtaca gggatggtgt    60
tggctcccgt at                                                        72
```

<210> SEQ ID NO 19
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 19

```
atccgtcaca cctgctcttg aatttcttta agtggaattc atatttgcaa atgatggtgt    60
tggctcccgt at                                                        72
```

<210> SEQ ID NO 20

```
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 20
atacgggagc caacaccagc agtcaagaag ttaagagaaa acaattgtg tataagagca      60 ggtgtgacgg at                                                        72

<210> SEQ ID NO 21
<211> LENGTH: 71
<212> TYPE: DNA
<213> ORGANISM: Artificial
<220> FEATURE:
<223> OTHER INFORMATION: Synthesized Oligonucleotide Sequence

<400> SEQUENCE: 21
atccgtcaca cctgctctgc gccacaagat tgcggaaaga cacccggggg gcttggtgtt     60
ggctcccgta t                                                         71

<210> SEQ ID NO 22
<211> LENGTH: 57
<212> TYPE: DNA
<213> ORGANISM: Artificial
<220> FEATURE:
<223> OTHER INFORMATION: Synthesized Oligonucleotide Sequence

<400> SEQUENCE: 22
atccgtcaca cctgctctgg ccttatgtaa agcgttgggt ggtgttggct cccgtat        57

<210> SEQ ID NO 23
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 23
atccgtcaca cctgctctcg atgagacaag accaacacgg cacaattgat ttaatggtgt     60
tggctcccgt at                                                        72

<210> SEQ ID NO 24
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 24
atccgtcaca cctgctcttg ggaggaactc gtaggatcat accgataata aaaatggtgt     60
tggctcccgt at                                                        72

<210> SEQ ID NO 25
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 25
atccgtcaca cctgctcttt tttattatcg gtatgatcct acgagttcct cccatggtgt     60
tggctcccgt at                                                        72
```

<210> SEQ ID NO 26
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 26
atccgtcaca cctgctctga aaggattaaa agaagtgagg ccgcttaacg ttaatggtgt    60
tggctcccgt at                                                       72

<210> SEQ ID NO 27
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 27
atacgggagc caacaccatc cctgtacctt gtccaagagc aatacctcta tattaccaca    60
accgagggca ta                                                       72

<210> SEQ ID NO 28
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 28
atccgtcaca cctgctctta tacacaattg tttttctctt aacttcttga ctgctggtgt    60
tggctcccgt at                                                       72

<210> SEQ ID NO 29
<211> LENGTH: 71
<212> TYPE: DNA
<213> ORGANISM: Artificial
<220> FEATURE:
<223> OTHER INFORMATION: Synthesized Oligonucleotide Sequence

<400> SEQUENCE: 29
atacgggagc caacaccaag cccccgggt gtctttccgc aatcttgtgg cgcagagcag    60
gtgtgacgga t                                                        71

<210> SEQ ID NO 30
<211> LENGTH: 57
<212> TYPE: DNA
<213> ORGANISM: Artificial
<220> FEATURE:
<223> OTHER INFORMATION: Synthesized Oligonucleotide Sequence

<400> SEQUENCE: 30
atacgggagc caacaccacc caacgcttta cataaggcca gagcaggtgt gacggat       57

<210> SEQ ID NO 31
<211> LENGTH: 76
<212> TYPE: DNA
<213> ORGANISM: Artificial
<220> FEATURE:
<223> OTHER INFORMATION: Synthesized Oligonucleotide Sequence

<400> SEQUENCE: 31
atccgtcaca cctgctctgg tggaatggac taagctagct agctagcgtt ttaaaaggtg    60

```
gtgttggctc ccgtat                                              76

<210> SEQ ID NO 32
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 32
atccgtcaca cctgctctgt aaggggggg aatcgctttc gtcttaagat gacatggtgt      60
tggctcccgt at                                                         72

<210> SEQ ID NO 33
<211> LENGTH: 59
<212> TYPE: DNA
<213> ORGANISM: Artificial
<220> FEATURE:
<223> OTHER INFORMATION: Synthesized Oligonucleotide Sequence

<400> SEQUENCE: 33
atccgtcaca cctgctctgc cggaccatcc aatatcagct gtggtgttgg ctcccgtat      59

<210> SEQ ID NO 34
<211> LENGTH: 71
<212> TYPE: DNA
<213> ORGANISM: Artificial
<220> FEATURE:
<223> OTHER INFORMATION: Synthesized Oligonucleotide Sequence

<400> SEQUENCE: 34
atccgtcaca cctgctctat ccgtcacgcc tgctctatcc gtcacacctg ctctggtgtt      60
ggctcccgta t                                                          71

<210> SEQ ID NO 35
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 35
atccgtcaca cctgctctat caaatgtgca gatatcaaga cgatttgtac aagatggtgt      60
tggctcccgt at                                                         72

<210> SEQ ID NO 36
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 36
atccgtcaca cctgctctgt agatggcaag gcataagcgt ccggaacgat agaatggtgt      60
tggctcccgt at                                                         72

<210> SEQ ID NO 37
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 37
```

```
atccgtcaca cctgctctgt agatggcaag gcataagcgt ccggaacgat agaatggtgt      60
tggctcccgt at                                                          72

<210> SEQ ID NO 38
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 38
atacgggagc caacaccacc ttttaaaacg ctagctagct tagtccattc caccagagca      60
ggtgtgacgg at                                                          72

<210> SEQ ID NO 39
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 39
atacgggagc caacaccatg tcatcttaag acgaaagcga ttcccccccc ttacagagca      60
ggtgtgacgg at                                                          72

<210> SEQ ID NO 40
<211> LENGTH: 59
<212> TYPE: DNA
<213> ORGANISM: Artificial
<220> FEATURE:
<223> OTHER INFORMATION: Synthesized Oligonucleotide Sequence

<400> SEQUENCE: 40
atacgggagc caacaccaca gctgatattg gatggtccgg cagagcaggt gtgacggat       59

<210> SEQ ID NO 41
<211> LENGTH: 71
<212> TYPE: DNA
<213> ORGANISM: Artificial
<220> FEATURE:
<223> OTHER INFORMATION: Synthesized Oligonucleotide Sequence

<400> SEQUENCE: 41
atacgggagc caacaccaga gcaggtgtga cggatagagc aggcgtgacg gatagagcag      60
gtgtgacgga t                                                           71

<210> SEQ ID NO 42
<211> LENGTH: 71
<212> TYPE: DNA
<213> ORGANISM: Artificial
<220> FEATURE:
<223> OTHER INFORMATION: Synthesized Oligonucleotide Sequence

<400> SEQUENCE: 42
atacgggagc caacaccatc ttgtacaatc gtcttgatat ctgcacattt gatagagcag      60
gtgtgacgga t                                                           71

<210> SEQ ID NO 43
<211> LENGTH: 72
<212> TYPE: DNA
<213> ORGANISM: Artificial
<220> FEATURE:
<223> OTHER INFORMATION: Synthesized Oligonucleotide Sequence
```

<400> SEQUENCE: 43
atacgggagc caacaccatt ctatcgttcc ggacggttat gccttgccat ctacagagca    60
ggtgtgacgg at    72

<210> SEQ ID NO 44
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 44
atacgggagc caacaccatt ctatcgttcc ggacgcttat gccttgccat ctacagagca    60
ggtgtgacgg at    72

<210> SEQ ID NO 45
<211> LENGTH: 60
<212> TYPE: DNA
<213> ORGANISM: Artificial
<220> FEATURE:
<223> OTHER INFORMATION: Synthesized Oligonucleotide Sequence

<400> SEQUENCE: 45
atccgtcaca cctgctctgc cggaccatcc aatatcagct gtggtgttgg gctcccgtat    60

<210> SEQ ID NO 46
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 46
atccgtcaca cctgctctgg tggaatggac taagctagct agcgttttaa aaggtggtgt    60
tggctcccgt at    72

<210> SEQ ID NO 47
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 47
atccgtcaca cctgctctta aagtagaggc tgttctccag acgtcgcagg aggatggtgt    60
tggctcccgt at    72

<210> SEQ ID NO 48
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 48
atccgtcaca cctgctctgt agatggcaag gcataagcgt ccggaacgat agaatggtgt    60
tggctcccgt at    72

<210> SEQ ID NO 49
<211> LENGTH: 72
<212> TYPE: DNA
<213> ORGANISM: Artificial
<220> FEATURE:

```
<223> OTHER INFORMATION: Synthesized Oligonucleotide Sequence

<400> SEQUENCE: 49
atccgtcaca cctgctctgt agatggcaag gcataagcgt ccggaacgat agaatggtgt    60
ggctccccgt at                                                         72

<210> SEQ ID NO 50
<211> LENGTH: 59
<212> TYPE: DNA
<213> ORGANISM: Artificial
<220> FEATURE:
<223> OTHER INFORMATION: Synthesized Oligonucleotide Sequence

<400> SEQUENCE: 50
atacgggagc caacaccaca gctgatattg gatggtccgg cagagcaggt gtgacggat     59

<210> SEQ ID NO 51
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 51
atccgtcaca cctgctcttg ggcaggagcg agagactcta atggtaagca agaatggtgt    60
tggctcccgt at                                                         72

<210> SEQ ID NO 52
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 52
atccgtcaca cctgctctcc aacaaggcga ccgaccgcat gcagatagcc aggttggtgt    60
tggctcccgt at                                                         72

<210> SEQ ID NO 53
<211> LENGTH: 58
<212> TYPE: DNA
<213> ORGANISM: Artificial
<220> FEATURE:
<223> OTHER INFORMATION: Synthesized Oligonucleotide Sequence

<400> SEQUENCE: 53
atacggagcc aacaccacag ctgatattgg atggtccggc agagcaggtg tgacggat      58

<210> SEQ ID NO 54
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 54
atacgggagc caacaccacc ttttaaaacg ctagctagct tagtccattc caccagagca    60
ggtgtgacgg at                                                         72

<210> SEQ ID NO 55
<211> LENGTH: 72
<212> TYPE: DNA
<213> ORGANISM: Artificial
<220> FEATURE:
```

<223> OTHER INFORMATION: Synthesized Oligonucleotide Sequence

<400> SEQUENCE: 55
atacgggagc caacaccatc ctcctgcgac gtctggagaa cagcctctac tttaagagca    60
ggtgtgacgg at    72

<210> SEQ ID NO 56
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 56
atacgggagc caacaccatt ctatcgttcc ggacgcttat gccttgccat ctacagagca    60
ggtgtgacgg at    72

<210> SEQ ID NO 57
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 57
atacgggagc caacaccatt ctatcgttcc ggacgcttat gccttgccat ctacagagca    60
ggtgtgacgg at    72

<210> SEQ ID NO 58
<211> LENGTH: 59
<212> TYPE: DNA
<213> ORGANISM: Artificial
<220> FEATURE:
<223> OTHER INFORMATION: Synthesized Oligonucleotide Sequence

<400> SEQUENCE: 58
atccgtcaca cctgctctgc cggaccatcc aatatcagct gtggtgttgg ctcccgtat    59

<210> SEQ ID NO 59
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 59
atacgggagc caacaccatt cttgcttacc attagagtct ctcgctcctg cccaagagca    60
ggtgtgacgg at    72

<210> SEQ ID NO 60
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 60
atacgggagc caacaccacc ctggctatct gcatgcggtc ggtcgccttg ttggagagca    60
ggtgtgacgg at    72

<210> SEQ ID NO 61
<211> LENGTH: 72
<212> TYPE: DNA

<213> ORGANISM: Artificial
<220> FEATURE:
<223> OTHER INFORMATION: Synthesized Oligonucleotide Sequence

<400> SEQUENCE: 61
atccgtcaca cctgctctgt agatggcaag gcataagcgt ccggaacgat agaatggtgt    60
tggctcccgt at    72

<210> SEQ ID NO 62
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 62
atccgtcaca cctgctctgt agatggcaag gcataagcgt ccggaacgat agaatggtgt    60
tggctcccgt at    72

<210> SEQ ID NO 63
<211> LENGTH: 59
<212> TYPE: DNA
<213> ORGANISM: Artificial
<220> FEATURE:
<223> OTHER INFORMATION: Synthesized Oligonucleotide Sequence

<400> SEQUENCE: 63
atccgtcaca cctgctctgc cggaccatcc aatatcagct gtggtgttgg ctcccgtat    59

<210> SEQ ID NO 64
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 64
atccgtcaca cctgctctga agcctaacgg agaagatggc cctactgccg taggtggtgt    60
tggctcccgt at    72

<210> SEQ ID NO 65
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 65
atccgtcaca cctgctctac taaacaaggg caaactgtaa acacagtagg ggcgtggtgt    60
tggctcccgt at    72

<210> SEQ ID NO 66
<211> LENGTH: 68
<212> TYPE: DNA
<213> ORGANISM: Artificial
<220> FEATURE:
<223> OTHER INFORMATION: Synthesized Oligonucleotide Sequence

<400> SEQUENCE: 66
atccgtcaca cctgctctgg tgttggctcc cgtatagctt ggctcccgta tggtgttggc    60
tcccgtat    68

<210> SEQ ID NO 67

```
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 67
atccgtcaca cctgctctgt cgcgatgatg agcagcagcg caggagggag ggggtggtgt      60
tggctcccgt at                                                         72

<210> SEQ ID NO 68
<211> LENGTH: 57
<212> TYPE: DNA
<213> ORGANISM: Artificial
<220> FEATURE:
<223> OTHER INFORMATION: Synthesized Oligonucleotide Sequence

<400> SEQUENCE: 68
atccgtcaca cctgctctga tcagggaaga cgccaacact ggtgttggct cccgtat        57

<210> SEQ ID NO 69
<211> LENGTH: 71
<212> TYPE: DNA
<213> ORGANISM: Artificial
<220> FEATURE:
<223> OTHER INFORMATION: Synthesized Oligonucleotide Sequence

<400> SEQUENCE: 69
atacgggagc caacaccatc tatcgttccg gacgcttatg ccttgccatc tacagagcag      60
gtgtgacgga t                                                          71

<210> SEQ ID NO 70
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 70
atacgggagc caacaccatc caaatcgcta gcttggtctc ctacccttt ggttagagca       60 ggtgtgacgg at                                                         72

<210> SEQ ID NO 71
<211> LENGTH: 59
<212> TYPE: DNA
<213> ORGANISM: Artificial
<220> FEATURE:
<223> OTHER INFORMATION: Synthesized Oligonucleotide Sequence

<400> SEQUENCE: 71
atacgggagc caacaccaca gctgatattg gatggtccgg cagagcaggt gtgacggat       59

<210> SEQ ID NO 72
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 72
atacgggagc caacaccacc tacggcagta gggccatctt ctccgttagg cttcagagca      60
ggtgtgacgg at                                                         72

<210> SEQ ID NO 73
```

<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 73
atacgggagc caacaccacg cccctactgt gtttacagtt tgcccttgtt tagtagagca    60
ggtgtgacgg at                                                       72

<210> SEQ ID NO 74
<211> LENGTH: 68
<212> TYPE: DNA
<213> ORGANISM: Artificial
<220> FEATURE:
<223> OTHER INFORMATION: Synthesized Oligonucleotide Sequence

<400> SEQUENCE: 74
atacgggagc caacaccata cgggagccaa gctatacggg agccaacacc agagcaggtg    60
tgacggat                                                            68

<210> SEQ ID NO 75
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 75
atacgggagc caacaccacc ccctccctcc tgcgctgctg ctcatcatcg cgacagagca    60
ggtgtgacgg at                                                       72

<210> SEQ ID NO 76
<211> LENGTH: 57
<212> TYPE: DNA
<213> ORGANISM: Artificial
<220> FEATURE:
<223> OTHER INFORMATION: Synthesized Oligonucleotide Sequence

<400> SEQUENCE: 76
atacgggagc caacaccagt gttggcgtct tccctgatca gagcaggtgt gacggat       57

<210> SEQ ID NO 77
<211> LENGTH: 58
<212> TYPE: DNA
<213> ORGANISM: Artificial
<220> FEATURE:
<223> OTHER INFORMATION: Synthesized Oligonucleotide Sequence

<400> SEQUENCE: 77
atccgtcaca cctgctctgt ccaaaggcta cgcgttaacg tggtgttggc tcccgtat      58

<210> SEQ ID NO 78
<211> LENGTH: 58
<212> TYPE: DNA
<213> ORGANISM: Artificial
<220> FEATURE:
<223> OTHER INFORMATION: Synthesized Oligonucleotide Sequence

<400> SEQUENCE: 78
atccgtcaca cctgctctgg agcaatatgg tggagaaacg tggtgttggc tcccgtat      58

<210> SEQ ID NO 79
<211> LENGTH: 59
<212> TYPE: DNA

<213> ORGANISM: Artificial
<220> FEATURE:
<223> OTHER INFORMATION: Synthesized Oligonucleotide Sequence

<400> SEQUENCE: 79
atccgtcaca cctgctctgc cggaccataa aatatcagct gtggtgttgg ctcccgtat    59

<210> SEQ ID NO 80
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 80
atccgtcaca cctgctctga acaggatagg gattagcgag tcaactaagc agcatggtgt    60
tggctcccgt at                                                        72

<210> SEQ ID NO 81
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 81
atccgtcaca cctgctctgg cggacaggaa ataagaatga acgcaaaatt tatctggtgt    60
tggctcccgt at                                                        72

<210> SEQ ID NO 82
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 82
atccgtcaca cctgctctac gcaagcggac aggaacattc attatagaat gtgttggtgt    60
tggctcccgt at                                                        72

<210> SEQ ID NO 83
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 83
atccgtcaca cctgctctcg gctgcaatgc gggagagtag ggggaaacca aacctggtgt    60
tggctcccgt at                                                        72

<210> SEQ ID NO 84
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 84
atccgtcaca cctgctctat gactggaaca cgggtatcga tgattagatg tccttcctgt    60
tggctcccgt at                                                        72

<210> SEQ ID NO 85

```
<211> LENGTH: 58
<212> TYPE: DNA
<213> ORGANISM: Artificial
<220> FEATURE:
<223> OTHER INFORMATION: Synthesized Oligonucleotide Sequence

<400> SEQUENCE: 85
atacgggagc caacaccacg ttaacgcgta gcctttggac agagcaggtg tgacggat        58

<210> SEQ ID NO 86
<211> LENGTH: 58
<212> TYPE: DNA
<213> ORGANISM: Artificial
<220> FEATURE:
<223> OTHER INFORMATION: Synthesized Oligonucleotide Sequence

<400> SEQUENCE: 86
atacgggagc caacaccacg tttctccacc atattgctcc agagcaggtg tgacggat        58

<210> SEQ ID NO 87
<211> LENGTH: 59
<212> TYPE: DNA
<213> ORGANISM: Artificial
<220> FEATURE:
<223> OTHER INFORMATION: Synthesized Oligonucleotide Sequence

<400> SEQUENCE: 87
atacgggagc caacaccaca gctgatattg gatggtccgg cagagcaggt gtgacggat       59

<210> SEQ ID NO 88
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 88
atacgggagc caacaccatg ctgcttagtt gactcgctaa tccctatcct gttcagagca      60
ggtgtgacgg at                                                         72

<210> SEQ ID NO 89
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 89
atacgggagc caacaccaga taaattttgc gttcattctt atttcctgtc cgccagagca      60
ggtgtgacgg at                                                         72

<210> SEQ ID NO 90
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 90
atacgggagc caacaccaac acattctata atgaatgttc ctgtcgcgtt gcgtagagca      60
ggtgtgacgg at                                                         72

<210> SEQ ID NO 91
<211> LENGTH: 72
<212> TYPE: DNA
```

<213> ORGANISM: Artificial
<220> FEATURE:
<223> OTHER INFORMATION: Synthesized Oligonucleotide Sequence

<400> SEQUENCE: 91
atacgggagc caacaccagg tttggttccc ccctactctc ccgcattgca gccgagagca    60
ggtgtgacgg at    72

<210> SEQ ID NO 92
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 92
atacgggagc caacaccaag gacatctaat catcgatacc cgtgttccag tcatagagca    60
ggtgtgacgg at    72

<210> SEQ ID NO 93
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 93
atccgtcaca cctgctctaa ttaggatacg gggcaacaga acgagagggg ggaatggtgt    60
tggctcccgt at    72

<210> SEQ ID NO 94
<211> LENGTH: 71
<212> TYPE: DNA
<213> ORGANISM: Artificial
<220> FEATURE:
<223> OTHER INFORMATION: Synthesized Oligonucleotide Sequence

<400> SEQUENCE: 94
atccgtcaca cctgctctcg gaccaggtca gacaagcaca tcggatatcc ggctggtgtt    60
ggctcccgta t    71

<210> SEQ ID NO 95
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 95
atccgtcaca cctgctcttg agtcaaagag tttagggagg agctaacata acagtggtgt    60
tggctcccgt at    72

<210> SEQ ID NO 96
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 96
atccgtcaca cctgctctaa caacaatgca tcagcgggct gggaacgcat gcggtggtgt    60
tggctcccgt at    72

<210> SEQ ID NO 97
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 97
atccgtcaca cctgctctga acaggttata agcaggagtg atagtttcag gatctggtgt    60
tggctcccgt at                                                        72

<210> SEQ ID NO 98
<211> LENGTH: 71
<212> TYPE: DNA
<213> ORGANISM: Artificial
<220> FEATURE:
<223> OTHER INFORMATION: Synthesized Oligonucleotide Sequence

<400> SEQUENCE: 98
atccgtcaca cctgctctcg gcggctcgca aaccgagtgg tcagcacccg ggttggtgtt    60
ggctcccgta t                                                         71

<210> SEQ ID NO 99
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 99
atccgtcaca cctgctctaa caacaatgca tcagcgggct gggaacgcat gcggtggtgt    60
tggctcccgt at                                                        72

<210> SEQ ID NO 100
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 100
atacgggagc caacaccatt cccccctctc gttctgttgc cccgtatcct aattagagca    60
ggtgtgacgg at                                                        72

<210> SEQ ID NO 101
<211> LENGTH: 71
<212> TYPE: DNA
<213> ORGANISM: Artificial
<220> FEATURE:
<223> OTHER INFORMATION: Synthesized Oligonucleotide Sequence

<400> SEQUENCE: 101
atacgggagc caacaccagc cggatatccg atgtgcttgt ctgacctggt ccgagagcag    60
gtgtgacgga t                                                         71

<210> SEQ ID NO 102
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 102

```
atacgggagc caacaccact gttatgttag ctcctcccta aactctttga ctcaagagca    60
ggtgtgacgg at                                                        72
```

<210> SEQ ID NO 103
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 103

```
atacgggagc caacaccacc gcatgcgttc ccagcccgct gatgcattgt tgttagagca    60
ggtgtgacgg at                                                        72
```

<210> SEQ ID NO 104
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 104

```
atacgggagc caacaccaga tcctgaaact atcactcctg cttataacct gttcagagca    60
ggtgtgacgg at                                                        72
```

<210> SEQ ID NO 105
<211> LENGTH: 71
<212> TYPE: DNA
<213> ORGANISM: Artificial
<220> FEATURE:
<223> OTHER INFORMATION: Synthesized Oligonucleotide Sequence

<400> SEQUENCE: 105

```
atacgggagc caacaccaac ccgggtgctg accactcggt ttgcgagccg ccgagagcag    60
gtgtgacgga t                                                         71
```

<210> SEQ ID NO 106
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 106

```
atacgggagc caacaccact atgttttcac ggtcttgtgg attacgtctt gcgcagagca    60
ggtgtgacgg at                                                        72
```

<210> SEQ ID NO 107
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 107

```
atccgtcaca cctgctctag gcgtagtgca taagtcgcgc gaaaatcaca gcattggtgt    60
tggctcccgt at                                                        72
```

<210> SEQ ID NO 108
<211> LENGTH: 72
<212> TYPE: DNA
<213> ORGANISM: Artificial
<220> FEATURE:

<223> OTHER INFORMATION: Synthesized Oligonucleotide Sequence

<400> SEQUENCE: 108
atccgtcaca cctgctctca gcggcagcta tacagtgaga acggactagt gcgttggtgt    60
tggctcccgt at    72

<210> SEQ ID NO 109
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 109
atccgtcaca cctgctctgg caaataatac tagcgatgat ggatctggat agactggtgt    60
tggctcccgt at    72

<210> SEQ ID NO 110
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 110
atccgtcaca cctgctctgg gggtgcgact tagggtaagt gggaaagacg atgctggtgt    60
tggctcccgt at    72

<210> SEQ ID NO 111
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 111
atccgtcaca cctgctctca agaggagatg aaccaatctt agtccgacag gcggtggtgt    60
tggctcccgt at    72

<210> SEQ ID NO 112
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 112
atccgtcaca cctgctctgg cccggaattg tcatgacgtc acctacacct cctgtggtgt    60
tggctcccgt at    72

<210> SEQ ID NO 113
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 113
atacgggagc caacaccaat gctgtgattt tcgcgcgact tagtcactac gcctagagca    60
ggtgtgacgg at    72

<210> SEQ ID NO 114

```
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 114
atacgggagc caacaccaac gcactagtcc gttctcactg tatagctgcc gctgagagca    60
ggtgtgacgg at                                                        72

<210> SEQ ID NO 115
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 115
atacgggagc caacaccagt ctatccagat ccatcatcgc tagtattatt tgccagagca    60
ggtgtgacgg at                                                        72

<210> SEQ ID NO 116
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 116
atacgggagc caacaccagc atcgtctttc ccacttaccc taagtcgcac ccccagagca    60
ggtgtgacgg at                                                        72

<210> SEQ ID NO 117
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 117
atacgggagc caacaccacc gcctgtcgga ctaagattgg ttcatctcct cttgagagca    60
ggtgtgacgg at                                                        72

<210> SEQ ID NO 118
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 118
atacgggagc caacaccaca ggaggtgtag gtgacgtcat gacaattccg ggccagagca    60
ggtgtgacgg at                                                        72

<210> SEQ ID NO 119
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 119
atccgtcacc cctgctctcg tcgctatgaa gtaacaaaga taggagcaat cgggtggtgt    60
```

-continued tggctcccgt at                                                         72

<210> SEQ ID NO 120
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 120
atccgtcaca cctgctctaa cgaagactga aaccaaagca gtgacagtgc tgaatggtgt    60
tggctcccgt at                                                         72

<210> SEQ ID NO 121
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 121
atccgtcaca cctgctctcg gtgacaatag ctcgatcagc ccaaagtcgt cagatggtgt    60
tggctcccgt at                                                         72

<210> SEQ ID NO 122
<211> LENGTH: 71
<212> TYPE: DNA
<213> ORGANISM: Artificial
<220> FEATURE:
<223> OTHER INFORMATION: Synthesized Oligonucleotide Sequence

<400> SEQUENCE: 122
atccgtcaca cctgctctaa cgaaatagac cacaaatcga tactttatgt tattggtgtt    60
ggctcccgta t                                                          71

<210> SEQ ID NO 123
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 123
atccgtcaca cctgctctgt cgaatgctct gcctggaaga gttgttagca gggatggtgt    60
tggctcccgt at                                                         72

<210> SEQ ID NO 124
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 124
atccgtcaca cctgctctta agccgagggg taaatctagg acagggtcc atgatggtgt     60 tggctcccgt at                                                         72

<210> SEQ ID NO 125
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 125
atccgtcaca cctgctctac tggccggctc agcatgacta agaaggaagt tatgtggtgt    60
tggctcccgt at                                                        72

<210> SEQ ID NO 126
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 126
atccgtcaca cctgctctgg tacgaatcac aggggatgct ggaagcttgg ctcttggtgt    60
tggctcccgt at                                                        72

<210> SEQ ID NO 127
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 127
atacgggagc caacaccacc cgattgctcc tatctttgtt acttcatagc gacgagagca    60
ggggtgacgg at                                                        72

<210> SEQ ID NO 128
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 128
atacgggagc caacaccatt cagcactgtc actgctttgg tttcagtctt cgttagagca    60
ggtgtgacgg at                                                        72

<210> SEQ ID NO 129
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 129
atacgggagc caacaccatc tgacgacttt gggctgatcg agctattgtc accgagagca    60
ggtgtgacgg at                                                        72

<210> SEQ ID NO 130
<211> LENGTH: 71
<212> TYPE: DNA
<213> ORGANISM: Artificial
<220> FEATURE:
<223> OTHER INFORMATION: Synthesized Oligonucleotide Sequence

<400> SEQUENCE: 130
atacgggagc caacaccaat aacataaagt atcgatttgt ggtctatttc gttagagcag    60
gtgtgacgga t                                                         71

<210> SEQ ID NO 131
<211> LENGTH: 72
<212> TYPE: DNA

```
<213> ORGANISM: Artificial
<220> FEATURE:
<223> OTHER INFORMATION: Synthesized Oligonucleotide Sequence

<400> SEQUENCE: 131
atacgggagc caacaccatc cctgctaaca actcttccag gcagagcatt cgacagagca    60
ggtgtgacgg at                                                       72

<210> SEQ ID NO 132
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 132
atacgggagc caacaccatc atggacccct gtcctagatt taccccctcgg cttaagagca   60 ggtgtgacgg at                                                       72

<210> SEQ ID NO 133
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 133
atacgggagc caacaccaca taacttcctt cttagtcatg ctgagccggc cagtagagca    60
ggtgtgacgg at                                                       72

<210> SEQ ID NO 134
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 134
atacgggagc caacaccaag agccaagctt ccagcatccc ctgtgattcg taccagagca    60
ggtgtgacgg at                                                       72

<210> SEQ ID NO 135
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 135
atccgtcaca cctgctctcc gcacgtagga ccactttggt acacgctccc gtagtggtgt    60
tggctcccgt at                                                       72

<210> SEQ ID NO 136
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 136
atccgtcaca cctgctctac ggatgaacga agattttaaa gtcaagctaa tgcatggtgt    60
tggctcccgt at                                                       72
```

```
<210> SEQ ID NO 137
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 137
atccgtcaca cctgctctgt agtgaagagt ccgcagtcca cgctgttcaa ctcatggtgt    60
tggctcccgt at                                                       72

<210> SEQ ID NO 138
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 138
atccgtcaca cctgctctac cggctggcac ggttatgtgt gacgggcgaa gatatggtgt    60
tggctcccgt at                                                       72

<210> SEQ ID NO 139
<211> LENGTH: 58
<212> TYPE: DNA
<213> ORGANISM: Artificial
<220> FEATURE:
<223> OTHER INFORMATION: Synthesized Oligonucleotide Sequence

<400> SEQUENCE: 139
atccgtcaca cctgctctgc gtgtggagcg cctaggtgag tggtgttggc tcccgtat     58

<210> SEQ ID NO 140
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 140
atccgtcaca cctgctctga tgtccctttg aagagttcca tgacgctggc tccttggtgt    60
tggctcccgt at                                                       72

<210> SEQ ID NO 141
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 141
atacgggagc caacaccact acgggagcgt gtaccaaagt ggtcctacgt gcggagagca    60
ggtgtgacgg at                                                       72

<210> SEQ ID NO 142
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 142
atacgggagc caacaccatg cattagcttg actttaaaat cttcgttcat ccgtagagca    60
```
ggtgtgacgg at                                                            72

<210> SEQ ID NO 143
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 143
atacgggagc caacaccatg agttgaacag cgtggactgc ggactcttca ctacagagca      60
ggtgtgacgg at                                                            72

<210> SEQ ID NO 144
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 144
atacgggagc caacaccata tcttcgcccg tcacacataa ccgtgccagc cggtagagca      60
ggtgtgacgg at                                                            72

<210> SEQ ID NO 145
<211> LENGTH: 58
<212> TYPE: DNA
<213> ORGANISM: Artificial
<220> FEATURE:
<223> OTHER INFORMATION: Synthesized Oligonucleotide Sequence

<400> SEQUENCE: 145
atacgggagc caacaccact cacctaggcg ctccacacgc agagcaggtg tgacggat         58

<210> SEQ ID NO 146
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 146
atacgggagc caacaccaag gagccagcgt catggaactc ttcaaaggga catcagagca      60
ggtgtgacgg at                                                            72

<210> SEQ ID NO 147
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 147
cattcaccac acctctgctg gcttggctag ccttgatgct aaacgaccca tagtgtggtg      60
tcgtcccgta tc                                                            72

<210> SEQ ID NO 148
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 148

```
gatacgggac gacaccacac tatgggtcgt ttagcatcaa aaacgaccca tagtgtggtg    60
tcgtcccgta tc                                                        72

<210> SEQ ID NO 149
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 149
cattcaccac acctctgctg gaggaggaag tggtctggag ttacttgaca tagtgtggtg    60
tcgtcccgta tc                                                        72

<210> SEQ ID NO 150
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 150
gatacgggac gacaccacac tatgtcaagt aactccagac cacttcctcc tccagcagag    60
gtgtggtgaa tg                                                        72

<210> SEQ ID NO 151
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 151
cattcaccac acctctgctg gacggaaaca atccccgggt acgagaatca gggtgtggtc    60
tcgtcccgta tc                                                        72

<210> SEQ ID NO 152
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 152
gatacgggac gacaccacac cctgattctc gtacccgggg attgtttccg tccagcagag    60
gtgtggtgaa tg                                                        72

<210> SEQ ID NO 153
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 153
cattcaccac acctctgctg gaaacctacc attaatgaga catgatgcgg tggtgtggtg    60
tcgtcccgta tc                                                        72

<210> SEQ ID NO 154
<211> LENGTH: 72
<212> TYPE: DNA
<213> ORGANISM: Artificial
<220> FEATURE:
```

<223> OTHER INFORMATION: Synthesized Oligonucleotide Sequence

<400> SEQUENCE: 154
gatacgggac gacaccacac caccgcatca tgtctcatta atggtaggtt tccagcagag    60
gtgtggtgaa tg                                                        72

<210> SEQ ID NO 155
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 155
atacgggagc caacaccatt ctatcgttcc ggacgcttat gccttgccat ctacagagca    60
ggtgtgacgg at                                                        72

<210> SEQ ID NO 156
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 156
atccgtcact cctgctctgt agatggcaag gcataagcgt ccggaacgat agaatggtgt    60
tggctcccgt at                                                        72

<210> SEQ ID NO 157
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 157
atacgggagc caacaccatg aatatctctt ctacctcctc tcctcccttt acttagagca    60
ggtgtgacgg at                                                        72

<210> SEQ ID NO 158
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 158
atccgtcact cctgctctaa gtaaagggag gagaggaggt agaagagata ttcatggtgt    60
tggctcccgt at                                                        72

<210> SEQ ID NO 159
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 159
atacgggagc caacaccacg ccgccccagt tcatggcctc tatgtccggc aacgagagca    60
ggtgtgacgg at                                                        72

<210> SEQ ID NO 160

```
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 160
atccgtcact cctgctctcg ttgccggaca tagaggccat gaactggggc ggcgtggtgt    60
tggctcccgt at                                                        72

<210> SEQ ID NO 161
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 161
atacgggagc caacaccatc tagatctgaa gaataaaaca aagacaaaga tgctagagca    60
ggtgtgacgg at                                                        72

<210> SEQ ID NO 162
<211> LENGTH: 69
<212> TYPE: DNA
<213> ORGANISM: Artificial
<220> FEATURE:
<223> OTHER INFORMATION: Synthesized Oligonucleotide Sequence

<400> SEQUENCE: 162
atccgtcact cctgctctag catctttgtc tttgttttat tcagatctag atggtgttgg    60
ctcccgtat                                                            69

<210> SEQ ID NO 163
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 163
atacgggagc caacaccacc ttttaaaacg ctagctagct tagtccattc caccagagca    60
ggtgtgacgg at                                                        72

<210> SEQ ID NO 164
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 164
atccgtcact cctgctctgg tggaatggac taagctagct agcgttttaa aaggtggtgt    60
tggctcccgt at                                                        72

<210> SEQ ID NO 165
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 165
atccgtcaca cctgctctcg atgtctgggc cctaatattg gtttgcttgt accatggtgt    60
```

```
tggctcccgt at                                                               72

<210> SEQ ID NO 166
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 166
atacgggagc caacaccatg gtacaagcaa accaatatta gggcccagac atcgagagca          60
ggtgtgacgg at                                                              72

<210> SEQ ID NO 167
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 167
atacgggagc caacaccatg atacccctaag gtaggggagg cctaagcgcc acgtagagca         60
ggtgtgacgg at                                                              72

<210> SEQ ID NO 168
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 168
atccgtcaca cctgctctac gtggcgctta ggcctcccct accttagggt atcatggtgt          60
tggctcccgt at                                                              72

<210> SEQ ID NO 169
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 169
atacgggagc caacaccacg catccccccgc cgggcccgcg ccccgctcgc agacagagca         60
ggtgtgacgg at                                                              72

<210> SEQ ID NO 170
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 170
atccgtcaca cctgctctgt ctgcgagcgg ggcgcgggcc cggcggggga tgcgtggtgt          60
tggctcccgt at                                                              72

<210> SEQ ID NO 171
<211> LENGTH: 73
<212> TYPE: DNA
<213> ORGANISM: Artificial
<220> FEATURE:
<223> OTHER INFORMATION: Synthesized Oligonucleotide Sequence
```

```
<400> SEQUENCE: 171
atccgtcaca cctgctctac ggcgctccca acaggcctct ccttacggca tattatggtg    60
ttggctcccg tat                                                       73

<210> SEQ ID NO 172
<211> LENGTH: 73
<212> TYPE: DNA
<213> ORGANISM: Artificial
<220> FEATURE:
<223> OTHER INFORMATION: Synthesized Oligonucleotide Sequence

<400> SEQUENCE: 172
atccgggagc caacaccata atatgccgta aggagaggcc tgttgggagc gccgtagagc    60
aggtgtgacg gat                                                       73

<210> SEQ ID NO 173
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 173
atacgggagc caacaccagg aaaaaaagag cctgtgaaga ttgtaatatc agttagagca    60
ggtgtgacgg at                                                        72

<210> SEQ ID NO 174
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 174
atccgtcaca cctgctctaa ctgatattac aatcttcaca ggctcttttt ttcctggtgt    60
tggctcccgt at                                                        72

<210> SEQ ID NO 175
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 175
atccgtcaca cctgctctcg gaggtagact aggattgcgg cggggggtca ggtatggtgt    60
tggctcccgt at                                                        72

<210> SEQ ID NO 176
<211> LENGTH: 71
<212> TYPE: DNA
<213> ORGANISM: Artificial
<220> FEATURE:
<223> OTHER INFORMATION: Synthesized Oligonucleotide Sequence

<400> SEQUENCE: 176
atacgggagc caacaccaca aaagccttac ctaactgcca acaatgaata gcaagagcag    60
gtgtgacgga t                                                         71

<210> SEQ ID NO 177
<211> LENGTH: 72
<212> TYPE: DNA
```

<213> ORGANISM: Artificial
<220> FEATURE:
<223> OTHER INFORMATION: Synthesized Oligonucleotide Sequence

<400> SEQUENCE: 177
atccgtcaca cctgctcttg ctattcattg ttggcagtta ggtaaggctt ttgttggtgt    60
tggctcccgt at    72

<210> SEQ ID NO 178
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 178
atacgggagc caacaccata cctgaccccc cgccgcaatc ctagtctacc tccgagagca    60
ggtgtgacgg at    72

<210> SEQ ID NO 179
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 179
atacgggagc caacaccacg actaacacga ccgttggggg gggctcgcgc gggcagagca    60
ggtgtgacgg at    72

<210> SEQ ID NO 180
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 180
atccgtcaca cctgctctgc ccgcgcgagc ccccccaac ggtcgtgtta gtcgtggtgt    60
tggctcccgt at    72

<210> SEQ ID NO 181
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 181
atacgggagc caacaccagt ccccgcccag ccgtgagccg taccccgca caccagagca    60 ggtgtgacgg at    72

<210> SEQ ID NO 182
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 182
atccgtcaca cctgctctgg tgtgcggggg tacggctcac ggctgggcgg ggactggtgt    60
tggctcccgt at    72

```
<210> SEQ ID NO 183
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 183
atccgtcaca cctgctctca aggttgggcc tgcaagagca aaaacggggc gggatggtgt      60
tggctcccgt at                                                          72

<210> SEQ ID NO 184
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 184
atacgggagc caacaccatc ccgccccgtt tttgctcttg caggcccaac cttgagagca      60
ggtgtgacgg at                                                          72

<210> SEQ ID NO 185
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 185
atccgtcaca cctgctctac ttggcttgcg actattattc acagggccaa agactggtgt      60
tggctcccgt at                                                          72

<210> SEQ ID NO 186
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 186
atacgggagc caacaccagt ctttggccct gtgaataata gtcgcaagcc aagtagagca      60
ggtgtgacgg at                                                          72

<210> SEQ ID NO 187
<211> LENGTH: 69
<212> TYPE: DNA
<213> ORGANISM: Artificial
<220> FEATURE:
<223> OTHER INFORMATION: Synthesized Oligonucleotide Sequence

<400> SEQUENCE: 187
atacgggagc caacaccata gtgttggacc aatacggtaa cgtgtccttg gagagcaggt      60
gtgacgaat                                                              69

<210> SEQ ID NO 188
<211> LENGTH: 69
<212> TYPE: DNA
<213> ORGANISM: Artificial
<220> FEATURE:
<223> OTHER INFORMATION: Synthesized Oligonucleotide Sequence

<400> SEQUENCE: 188
```

```
atccgtcaca cctgctctcc aaggacacgt taccgtattg gtccaacact atggtgttgg      60
ctcccgtat                                                              69

<210> SEQ ID NO 189
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 189
atccgtcaca cctgctcttg gaatgtcggt gttttccaa ttccttgggt cgtgtggtgt       60
tggctcccgt at                                                          72

<210> SEQ ID NO 190
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 190
atacgggagc caacaccaca cgacccaagg aattggaaaa acaccgacat tccaagagca      60
ggtgtgacgg at                                                          72

<210> SEQ ID NO 191
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 191
atccgtcaca cctgctctgc gacggcgacg cggtccgggc ggggggtggag gacgtggtgt     60 tggctcccgt at                                                          72

<210> SEQ ID NO 192
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 192
atacgggagc caacaccacg tcctccaccc ccgcccggac cgcgtcgccg tcgcagagca      60
ggtgtgacgg at                                                          72

<210> SEQ ID NO 193
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 193
atacgggagc caacaccaga gggttctagc gtcacttcca tgagaatggc tcacagagca      60
ggtgtgacgg at                                                          72

<210> SEQ ID NO 194
<211> LENGTH: 72
<212> TYPE: DNA
<213> ORGANISM: Artificial
<220> FEATURE:
```

<223> OTHER INFORMATION: Synthesized Oligonucleotide Sequence

<400> SEQUENCE: 194
atccgtcaca cctgctctgg cctggggacg cgagggaggc gggggagtc gtggtggtgt    60 tggctcccgt at    72

<210> SEQ ID NO 195
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 195
atacgggagc caacaccacc acgactcccc ccgcctccct cgcgtcccca ggccagagca    60
ggtgtgacgg at    72

<210> SEQ ID NO 196
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 196
atccgtcaca cctgctctgg cctggggacg cgagggaggc gggggagtc gtggtggtgt    60 tggctcccgt at    72

<210> SEQ ID NO 197
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 197
atccgtcaca cctgctctca cagggcctct tactatacag ttctccagcg ctgctggtgt    60
tggctcccgt at    72

<210> SEQ ID NO 198
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 198
atacgggagc caaccaccagc agcgctggag aactgtatag taagaggccc tgtgagagca    60
ggtgtgacgg at    72

<210> SEQ ID NO 199
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 199
atccgtcaca cctgctctgc acgggctcag tttggctttg tatcctaaga gagatggtgt    60
tggctcccgt at    72

<210> SEQ ID NO 200

```
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 200
atacgggagc caacaccatc tctcttagga tacaaagcca aactgagccc gtgcagagca      60
ggtgtgacgg at                                                         72

<210> SEQ ID NO 201
<211> LENGTH: 71
<212> TYPE: DNA
<213> ORGANISM: Artificial
<220> FEATURE:
<223> OTHER INFORMATION: Synthesized Oligonucleotide Sequence

<400> SEQUENCE: 201
atacgggagc caacaccagg ggtggcgaac atggtataac ttgataagtg tgaagagcag      60
gtgtgacgga t                                                          71

<210> SEQ ID NO 202
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 202
atccgtcaca cctgctcttc acacttatca agttatacca tgttcgccac ccctggtgt      60 tggctcccgt at                                                         72

<210> SEQ ID NO 203
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 203
atacgggagc caacaccact ccgacaccgg ccgccggcac cacccactcc ccctagagca      60
ggtgtgacgg at                                                         72

<210> SEQ ID NO 204
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 204
atccgtcaca cctgctctag ggggagtggg tggtgccggc ggccggtgtc ggagtggtgt      60
tggctcccgt at                                                         72

<210> SEQ ID NO 205
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 205
atacgggagc caacaccatc cggcgcgccc tcctccccca ctgctccccg cccgagagca      60
```

```
ggtgtgacgg at                                                              72

<210> SEQ ID NO 206
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 206
atccgtcaca cctgctctcg ggcggggagc agtgggggag gagggcgcgc cggatggtgt         60
tggctcccgt at                                                              72

<210> SEQ ID NO 207
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 207
atacgggagc caacaccata cgcagaggtc ccctacccag gccagccgga tgccagagca         60
ggtgtgacgg at                                                              72

<210> SEQ ID NO 208
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 208
atccgtcaca cctgctctgg catccggctg gcctgggtag gggacctctg cgtatggtgt         60
tggctcccgt at                                                              72

<210> SEQ ID NO 209
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 209
atccgtcaca cctgctctgg agacattaaa aaccggagtt tatttatacc tttctggtgt         60
tggctcccgt at                                                              72

<210> SEQ ID NO 210
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 210
atacgggagc caacaccaga aaggtataaa taaactccgg tttttaatgt ctccagagca         60
ggtgtgacgg at                                                              72

<210> SEQ ID NO 211
<211> LENGTH: 59
<212> TYPE: DNA
<213> ORGANISM: Artificial
<220> FEATURE:
<223> OTHER INFORMATION: Synthesized Oligonucleotide Sequence
```

```
<400> SEQUENCE: 211
atacgggagc caacaccact aacttgttgc tgatcttatc cagagcaggt gtgacggat       59

<210> SEQ ID NO 212
<211> LENGTH: 59
<212> TYPE: DNA
<213> ORGANISM: Artificial
<220> FEATURE:
<223> OTHER INFORMATION: Synthesized Oligonucleotide Sequence

<400> SEQUENCE: 212
atccgtcaca cctgctctgg ataagatcag caacaagtta gtggtgttgg ctcccgtat       59

<210> SEQ ID NO 213
<211> LENGTH: 58
<212> TYPE: DNA
<213> ORGANISM: Artificial
<220> FEATURE:
<223> OTHER INFORMATION: Synthesized Oligonucleotide Sequence

<400> SEQUENCE: 213
atccgtcaca cctgctctgc atggagagtt ttttggtcag tggtgttggc tcccgtat       58

<210> SEQ ID NO 214
<211> LENGTH: 58
<212> TYPE: DNA
<213> ORGANISM: Artificial
<220> FEATURE:
<223> OTHER INFORMATION: Synthesized Oligonucleotide Sequence

<400> SEQUENCE: 214
atacgggagc caacaccact gaccaaaaaa ctctccatgc agagcaggtg tgacggat       58

<210> SEQ ID NO 215
<211> LENGTH: 58
<212> TYPE: DNA
<213> ORGANISM: Artificial
<220> FEATURE:
<223> OTHER INFORMATION: Synthesized Oligonucleotide Sequence

<400> SEQUENCE: 215
atacgggagc caacaccacg ttaacgcgta gcctttggac agagcaggtg tgacggat       58

<210> SEQ ID NO 216
<211> LENGTH: 58
<212> TYPE: DNA
<213> ORGANISM: Artificial
<220> FEATURE:
<223> OTHER INFORMATION: Synthesized Oligonucleotide Sequence

<400> SEQUENCE: 216
atccgtcaca cctgctctgt ccaaaggcta cgcgttaacg tggtgttggc tcccgtat       58

<210> SEQ ID NO 217
<211> LENGTH: 59
<212> TYPE: DNA
<213> ORGANISM: Artificial
<220> FEATURE:
<223> OTHER INFORMATION: Synthesized Oligonucleotide Sequence

<400> SEQUENCE: 217
atccgtcaca cctgctctgc cggaccatcc aatatcagct gtggtgttgg ctcccgtat       59

<210> SEQ ID NO 218
<211> LENGTH: 59
<212> TYPE: DNA
```

<213> ORGANISM: Artificial
<220> FEATURE:
<223> OTHER INFORMATION: Synthesized Oligonucleotide Sequence

<400> SEQUENCE: 218
atacgggagc caacaccaca gctgatattg gatggtccgg cagagcaggt gtgacggat    59

<210> SEQ ID NO 219
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 219
atccgtcaca cctgctctcg tccgtcatta agttcggagg ctggcgggtt gcgttggtgt    60
tggctcccgt at    72

<210> SEQ ID NO 220
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 220
atacgggagc caacaccaac gcaacccgcc agcctccgaa cttaatgacg gacgagagca    60
ggtgtgacgg at    72

<210> SEQ ID NO 221
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 221
atacgggagc caacaccatt ctatcgttcc ggacgcttat gccttgccat ctacagagca    60
ggtgtgacgg at    72

<210> SEQ ID NO 222
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 222
atccgtcaca cctgctctgt agatggcaag gcataagcgt ccggaacgat agaatggtgt    60
tggctcccgt at    72

<210> SEQ ID NO 223
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 223
atccgtcaca cctgctctaa ctcttactac tttgttgcta tcacattcaa ctgttggtgt    60
tggctcccgt at    72

<210> SEQ ID NO 224

-continued

```
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 224
atacgggagc caacaccaac agttgaatgt gatagcaaca aagtagtaag agttagagca      60
ggtgtgacgg at                                                         72

<210> SEQ ID NO 225
<211> LENGTH: 58
<212> TYPE: DNA
<213> ORGANISM: Artificial
<220> FEATURE:
<223> OTHER INFORMATION: Synthesized Oligonucleotide Sequence

<400> SEQUENCE: 225
atccgtcaca cctgctctgg cctttcacca agcgtccttg tggtgttggc tcccgtat       58

<210> SEQ ID NO 226
<211> LENGTH: 58
<212> TYPE: DNA
<213> ORGANISM: Artificial
<220> FEATURE:
<223> OTHER INFORMATION: Synthesized Oligonucleotide Sequence

<400> SEQUENCE: 226
atacgggagc caacaccaca aggacgcttg gtgaaaggcc agagcaggtg tgacggat       58

<210> SEQ ID NO 227
<211> LENGTH: 58
<212> TYPE: DNA
<213> ORGANISM: Artificial
<220> FEATURE:
<223> OTHER INFORMATION: Synthesized Oligonucleotide Sequence

<400> SEQUENCE: 227
atccgtcaca cctgctctgg caccgagcac gggaacccag tggtgttggc tcccgtat       58

<210> SEQ ID NO 228
<211> LENGTH: 58
<212> TYPE: DNA
<213> ORGANISM: Artificial
<220> FEATURE:
<223> OTHER INFORMATION: Synthesized Oligonucleotide Sequence

<400> SEQUENCE: 228
atacgggagc caacaccact gggttcccgt gctcggtgcc agagcaggtg tgacggat       58

<210> SEQ ID NO 229
<211> LENGTH: 69
<212> TYPE: DNA
<213> ORGANISM: Artificial
<220> FEATURE:
<223> OTHER INFORMATION: Synthesized Oligonucleotide Sequence

<400> SEQUENCE: 229
atacgggagc caacaccata gtgttgggcc aatacggtaa cgtgtccttg gagagcaggt     60
gtgacggat                                                            69

<210> SEQ ID NO 230
<211> LENGTH: 69
<212> TYPE: DNA
<213> ORGANISM: Artificial
<220> FEATURE:
```

<223> OTHER INFORMATION: Synthesized Oligonucleotide Sequence

<400> SEQUENCE: 230

```
atccgtcaca cctgctctcc aaggacacgt taccgtattg gcccaacact atggtgttgg    60
ctcccgtat                                                             69
```

<210> SEQ ID NO 231
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 231

```
atccgtcaca cctgctctac ccgatgccgc cccgggattg ttgtatgacc atcttggtgt    60
tggctcccgt at                                                         72
```

<210> SEQ ID NO 232
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 232

```
atacgggagc caacaccaag atggtcatac aacaatcccg ggcggcatc gggtagagca     60
ggtgtgacgg at                                                         72
```

<210> SEQ ID NO 233
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 233

```
atacgggagc caacaccacc ccatgagtac acgtgaacgg acacagcctc cggcagagca    60
ggtgtgacgg at                                                         72
```

<210> SEQ ID NO 234
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 234

```
atccgtcaca cctgctctgc cggaggctgt gtccgttcac gtgtactcat ggggtggtgt    60
tggctcccgt at                                                         72
```

<210> SEQ ID NO 235
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 235

```
atccgtcaca cctgctctta accattcatt tcttttgtgg tatgaccgtt cgcctggtgt    60
tggctcccgt at                                                         72
```

<210> SEQ ID NO 236

```
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 236
atacgggagc caacaccagg cgaacggtca taccacaaaa gaaatgaatg gttaagagca      60
ggtgtgacgg at                                                          72

<210> SEQ ID NO 237
<211> LENGTH: 58
<212> TYPE: DNA
<213> ORGANISM: Artificial
<220> FEATURE:
<223> OTHER INFORMATION: Synthesized Oligonucleotide Sequence

<400> SEQUENCE: 237
atccgtcaca cctgctctgg ggctcttttc gttaaccagg tggtgttggc tcccgtat        58

<210> SEQ ID NO 238
<211> LENGTH: 58
<212> TYPE: DNA
<213> ORGANISM: Artificial
<220> FEATURE:
<223> OTHER INFORMATION: Synthesized Oligonucleotide Sequence

<400> SEQUENCE: 238
atacgggagc caacaccacc tggttaacga aaagagcccc agagcaggtg tgacggat        58

<210> SEQ ID NO 239
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 239
atacgggagc caacaccaga taaattttgc gttcattctt atttcctgtc cgccagagca      60
ggtgtgacgg at                                                          72

<210> SEQ ID NO 240
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 240
atccgtcaca cctgctctgg cggacaggaa ataagaatga acgcaaaatt tatctggtgt      60
tggctcccgt at                                                          72

<210> SEQ ID NO 241
<211> LENGTH: 71
<212> TYPE: DNA
<213> ORGANISM: Artificial
<220> FEATURE:
<223> OTHER INFORMATION: Synthesized Oligonucleotide Sequence

<400> SEQUENCE: 241
atacgggagc caacaccaga taaattttgg ttcattctta tttcctgtcc gccagagcag      60
gtgtgacgga t                                                           71

<210> SEQ ID NO 242
```

```
<211> LENGTH: 71
<212> TYPE: DNA
<213> ORGANISM: Artificial
<220> FEATURE:
<223> OTHER INFORMATION: Synthesized Oligonucleotide Sequence

<400> SEQUENCE: 242
atccgtcaca cctgctctgg cggacaggaa ataagaatga accaaaattt atctggtgtt      60
ggctcccgta t                                                          71

<210> SEQ ID NO 243
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 243
atacgggagc caacaccacg gggctaccag caccgtcacc cctcattctg ccacagagca      60
ggtgtgacgg at                                                         72

<210> SEQ ID NO 244
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 244
atccgtcaca cctgctctgt ggcagaatga ggggtgacgg tgctggtagc cccgtggtgt      60
tggctcccgt at                                                         72

<210> SEQ ID NO 245
<211> LENGTH: 69
<212> TYPE: DNA
<213> ORGANISM: Artificial
<220> FEATURE:
<223> OTHER INFORMATION: Synthesized Oligonucleotide Sequence

<400> SEQUENCE: 245
atacgggagc caacaccaaa agatggaaaa cactggaagg aaaatgcggt cagagcaggt      60
gtgacggat                                                             69

<210> SEQ ID NO 246
<211> LENGTH: 69
<212> TYPE: DNA
<213> ORGANISM: Artificial
<220> FEATURE:
<223> OTHER INFORMATION: Synthesized Oligonucleotide Sequence

<400> SEQUENCE: 246
atccgtcaca cctgctctga ccgcattttc cttccagtgt tttccatctt tggtgttgg      60 ctcccgtat                                                             69

<210> SEQ ID NO 247
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 247
atacgggagc caacaccacc gggccgatgg gcaccaggaa ctctcggacg agtgagagca      60
```

```
ggtgtgacgg at                                                            72

<210> SEQ ID NO 248
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 248
atccgtcaca cctgctctca ctcgtccgag agttcctggt gcccatcggc ccggtggtgt        60
tggctcccgt at                                                            72

<210> SEQ ID NO 249
<211> LENGTH: 59
<212> TYPE: DNA
<213> ORGANISM: Artificial
<220> FEATURE:
<223> OTHER INFORMATION: Synthesized Oligonucleotide Sequence

<400> SEQUENCE: 249
atacgggagc caacaccaca gctgatattg gatggtccgg cagagcaggt gtgacggat         59

<210> SEQ ID NO 250
<211> LENGTH: 59
<212> TYPE: DNA
<213> ORGANISM: Artificial
<220> FEATURE:
<223> OTHER INFORMATION: Synthesized Oligonucleotide Sequence

<400> SEQUENCE: 250
atccgtcaca cctgctctgc cggaccatcc aatatcagct gtggtgttgg ctcccgtat        59

<210> SEQ ID NO 251
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 251
atacgggagc caacaccagt gggctaccag cgaaaggcgg ccgtccagtc gagtgatttg        60
acctagagca at                                                            72

<210> SEQ ID NO 252
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 252
atccgtcaca cctgctctag gtcaaatcac tcgactggac ggccgccttt cgactggtgt        60
tggctcccgt at                                                            72

<210> SEQ ID NO 253
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 253
atacgggagc caacaccacg gggcgtgccg tcaaaagacc gagatgtgg ctgcgagagca       60
```

```
ggtgtgacgg at                                                            72
```

<210> SEQ ID NO 254
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 254

```
atccgtcaca cctgctctcg cagcccactc tcggtctttt gacggcacgc cccgtggtgt        60
tggctcccgt at                                                            72
```

<210> SEQ ID NO 255
<211> LENGTH: 59
<212> TYPE: DNA
<213> ORGANISM: Artificial
<220> FEATURE:
<223> OTHER INFORMATION: Synthesized Oligonucleotide Sequence

<400> SEQUENCE: 255

```
atacgggagc caacaccact aacttgttgc tgatcttatc cagagcaggt gtgacggat         59
```

<210> SEQ ID NO 256
<211> LENGTH: 59
<212> TYPE: DNA
<213> ORGANISM: Artificial
<220> FEATURE:
<223> OTHER INFORMATION: Synthesized Oligonucleotide Sequence

<400> SEQUENCE: 256

```
atccgtcaca cctgctctgg ataagatcag caacaagtta gtggtgttgg ctcccgtat         59
```

<210> SEQ ID NO 257
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 257

```
atacgggagc caacaccatt tagcgtaggg ctcgcttatc atttctcatt ccctagagca        60
ggtgtgacgg at                                                            72
```

<210> SEQ ID NO 258
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 258

```
atccgtcaca cctgctctag ggaatgagaa atgataagcg agccctacgc taaatggtgt        60
tggctcccgt at                                                            72
```

<210> SEQ ID NO 259
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 259

```
atacgggagc caacaccacc gcaacccaaa tctctacacg gattatcgtc gagcagagca        60
```
ggtgtgacgg at                                                           72

<210> SEQ ID NO 260
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 260
atccgtcaca cctgctctgc tcgacgataa tccgtgtaga gatttgggtt gcggtggtgt      60
tggctcccgt at                                                          72

<210> SEQ ID NO 261
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 261
atacgggagc caacaccaac acattctata atgaatgttc ctgtcgcgtt gcgtagagca      60
ggtgtgacgg at                                                          72

<210> SEQ ID NO 262
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 262
atccgtcaca cctgctctac gcaacgcgac aggaacattc attatagaat gtgttggtgt      60
tggctcccgt at                                                          72

<210> SEQ ID NO 263
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 263
atacgggagc caacaccagc ctaccccccc tgtacgaggg ccgcaaccac gtagagagca      60
ggtgtgacgg at                                                          72

<210> SEQ ID NO 264
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 264
atccgtcaca cctgctctct acgtggttgc ggccctcgta caggggggt aggctggtgt       60 tggctcccgt at                                                          72

<210> SEQ ID NO 265
<211> LENGTH: 59
<212> TYPE: DNA
<213> ORGANISM: Artificial
<220> FEATURE:
<223> OTHER INFORMATION: Synthesized Oligonucleotide Sequence

```
<400> SEQUENCE: 265
atacgggagc caacaccaca tctagcacga gaccctatcc cagagcaggt gtgacggat      59

<210> SEQ ID NO 266
<211> LENGTH: 59
<212> TYPE: DNA
<213> ORGANISM: Artificial
<220> FEATURE:
<223> OTHER INFORMATION: Synthesized Oligonucleotide Sequence

<400> SEQUENCE: 266
atccgtcaca cctgctctgg datagggtct cgtgctagat gtggtgttgg ctcccgtat      59

<210> SEQ ID NO 267
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 267
atacgggagc caacaccaac agcgactcga gtctgacgac tcgcggggca aatgagagca    60
ggtgtgacgg at                                                        72

<210> SEQ ID NO 268
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 268
atccgtcaca cctgctctca tttgccccgc gagtcgtcag actcgagtcg ctgttggtgt    60
tggctcccgt at                                                        72

<210> SEQ ID NO 269
<211> LENGTH: 69
<212> TYPE: DNA
<213> ORGANISM: Artificial
<220> FEATURE:
<223> OTHER INFORMATION: Synthesized Oligonucleotide Sequence

<400> SEQUENCE: 269
atacgggagc caacaccata gtgttgggcc aatacggtaa cgtgtccttg gagagcaggt    60
gtgacggat                                                            69

<210> SEQ ID NO 270
<211> LENGTH: 69
<212> TYPE: DNA
<213> ORGANISM: Artificial
<220> FEATURE:
<223> OTHER INFORMATION: Synthesized Oligonucleotide Sequence

<400> SEQUENCE: 270
atccgtcaca cctgctctcc aaggacacgt taccgtattg gcccaacact atggtgttgg    60
ctcccgtat                                                            69

<210> SEQ ID NO 271
<211> LENGTH: 72
<212> TYPE: DNA
<213> ORGANISM: Artificial
<220> FEATURE:
<223> OTHER INFORMATION: Synthesized Oligonucleotide Sequence
```

<400> SEQUENCE: 271
atacgggagc caacaccact aaggagaggt cgcgacagac tcttctggtc aaggagagca    60
ggtgtgacgg at    72

<210> SEQ ID NO 272
<211> LENGTH: 73
<212> TYPE: DNA
<213> ORGANISM: Artificial
<220> FEATURE:
<223> OTHER INFORMATION: Synthesized Oligonucleotide Sequence

<400> SEQUENCE: 272
atccgtcaca cctgctctcc ttgaccagaa gagtctgtcg cgacctctcc ttagtggtgt    60
tggctcccgt atg    73

<210> SEQ ID NO 273
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 273
atacgggagc caacaccaac ttcgactcaa agaagtccac gtgagactgg tggaagagca    60
ggtgtgacgg at    72

<210> SEQ ID NO 274
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 274
atccgtcaca cctgctcttc caccagtctc acgtggactt ctttgagtcg aagttggtgt    60
tggctcccgt at    72

<210> SEQ ID NO 275
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 275
atacgggagc caacaccaac ttcgactcaa agaagtccac gtgagactgg tggaagagca    60
ggtgtgacgg at    72

<210> SEQ ID NO 276
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 276
atccgtcaca cctgctctcg acaaggattg tgcgcccgtg cgggtctccc cgggtggtgt    60
tggctcccgt at    72

<210> SEQ ID NO 277
<211> LENGTH: 72
<212> TYPE: DNA

```
<213> ORGANISM: Artificial
<220> FEATURE:
<223> OTHER INFORMATION: Synthesized Oligonucleotide Sequence

<400> SEQUENCE: 277
atacgggagc caacaccagc tggaccaaac agaagtccac gtgagactgg tggaagagca      60
ggtgtgacgg at                                                          72

<210> SEQ ID NO 278
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 278
atccgtcaca cctgctctcc ggggaccccc acaatgggcg tagtttggtc cagctggtgt      60
tggctcccgt at                                                          72

<210> SEQ ID NO 279
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 279
atacgggagc caacaccatc ctaactggtc taattttgc tgttaccgat cccgagagca       60
ggtgtgacgg at                                                          72

<210> SEQ ID NO 280
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 280
atccgtcaca cctgctctcg ggatcggtaa cagcaaaaat tagaccagtt aggatggtgt      60
tggctcccgt at                                                          72

<210> SEQ ID NO 281
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 281
atacgggagc caacaccagc ctgacgaaaa aattttatca ctaagtgata cgcaagagca      60
ggtgtgacgg at                                                          72

<210> SEQ ID NO 282
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 282
atccgtcaca cctgctcttg cgtatcactt agtgataaaa ttttttcgtc aggctggtgt      60
tggctcccgt at                                                          72
```

```
<210> SEQ ID NO 283
<211> LENGTH: 71
<212> TYPE: DNA
<213> ORGANISM: Artificial
<220> FEATURE:
<223> OTHER INFORMATION: Synthesized Oligonucleotide Sequence

<400> SEQUENCE: 283
atacgggagc caacaccaga cctacttcag aaacggaaat gttcttagcc gtcagagcag      60
gtgtgacgga t                                                          71

<210> SEQ ID NO 284
<211> LENGTH: 71
<212> TYPE: DNA
<213> ORGANISM: Artificial
<220> FEATURE:
<223> OTHER INFORMATION: Synthesized Oligonucleotide Sequence

<400> SEQUENCE: 284
atccgtcaca cctgctctga cggctaagaa catttccgtt tctgaagtag gtctggtgtt      60
ggctcccgta t                                                          71

<210> SEQ ID NO 285
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 285
atacgggagc caacaccagg ccaacgaaac tcctactaca tataatgctt atgcagagca      60
ggtgtgacgg at                                                         72

<210> SEQ ID NO 286
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 286
atccgtcaca cctgctctgc ataagcatta tatgtagtag gagtttcgtt ggcctggtgt      60
tggctcccgt at                                                         72

<210> SEQ ID NO 287
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 287
atacgggagc caacaccatc ctaactggtc taattttttgc tgttaccgat cccgagagca     60
ggtgtgacgg at                                                         72

<210> SEQ ID NO 288
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 288
```

| | |
|---|---|
| atccgtcaca cctgctctcg ggatcggtaa cagcaaaaat tagaccagtt aggatggtgt | 60 |
| tggctcccgt at | 72 |

<210> SEQ ID NO 289
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 289

| | |
|---|---|
| atacgggagc caacaccagg cgaccaagtt tgaatcacca caatcgtgac ggtgagagca | 60 |
| ggtgtgacgg at | 72 |

<210> SEQ ID NO 290
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 290

| | |
|---|---|
| atccgtcaca cctgctctca ccgtcacgat tgtggtgatt caaacttggt cgcctggtgt | 60 |
| tggctcccgt at | 72 |

<210> SEQ ID NO 291
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 291

| | |
|---|---|
| atacgggagc caacaccacc atcacatctt ggcccggtac cctggatact agccagagca | 60 |
| ggtgtgacgg at | 72 |

<210> SEQ ID NO 292
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 292

| | |
|---|---|
| atccgtcaca cctgctctgg ctagtatcca gggtaccggg ccaagatgtg atggtggtgt | 60 |
| tggctcccgt at | 72 |

<210> SEQ ID NO 293
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 293

| | |
|---|---|
| atacgggagc caacaccagc actagctcgg gtaacgggga cattagagtt tgccagagca | 60 |
| ggtgtgacgg at | 72 |

<210> SEQ ID NO 294
<211> LENGTH: 72
<212> TYPE: DNA
<213> ORGANISM: Artificial
<220> FEATURE:

<223> OTHER INFORMATION: Synthesized Oligonucleotide Sequence

<400> SEQUENCE: 294
atccgtcaca cctgctctgg caaactctaa tgtccccgtt acccgagcta gtgctggtgt    60
tggctcccgt at    72

<210> SEQ ID NO 295
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 295
atccgtcaca cctgctctag ttggaagtct tgtagatctg ggcgcggtgg gctttggtgt    60
tggctcccgt at    72

<210> SEQ ID NO 296
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 296
atacgggagc caacaccaaa gcccaccgcg cccagatcta caagacttcc aactagagca    60
ggtgtgacgg at    72

<210> SEQ ID NO 297
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 297
atacgggagc caacaccatc tttgtcactc tggattaggt taatgcactg aaacagagca    60
ggtgtgacgg at    72

<210> SEQ ID NO 298
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 298
atccgtcaca cctgctctgt ttcagtggat taagctaatc cagagtgaca aagatggtgt    60
tggctcccgt at    72

<210> SEQ ID NO 299
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 299
atccgtcaca cctgctctcg ctcgagggg acaattgcta gaatcccggg ttcgtggtgt    60
tggctcccgt at    72

<210> SEQ ID NO 300

```
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 300
atacgggagc caagaccacg aacccgggat tctagcaatt gtcccccctcg agcgagagca      60 ggtgtgacgg at                                                          72

<210> SEQ ID NO 301
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 301
atacgggagc caacaccaat gattaataga acccctatg acctggccgc tgggagagca        60
ggtgtgacgg at                                                          72

<210> SEQ ID NO 302
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 302
atccgtcaca cctgctctcc cagcggccag gtcatagggg gttctattaa tcattggtgt       60
tggctcccgt at                                                          72

<210> SEQ ID NO 303
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 303
atccgtcaca cctgctcttg ttaaacccga caacatggac atgctatccg accatggtgt      60
tggctcccgt at                                                          72

<210> SEQ ID NO 304
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 304
atacgggagc caacaccatg gtcggatagc atgtccatgt tgtcgggttt aacaagagca      60
ggtgtgacgg at                                                          72

<210> SEQ ID NO 305
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 305
atacgggagc caacaccagg ggaatcttgc ttgcgtagcg acgcataatg acgtagagca      60
```

```
ggtgtgacgg at                                                         72

<210> SEQ ID NO 306
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 306
atccgtcaca cctgctctac gtcattatgc gtcgctacgc aagcaagatt cccctggtgt    60
tggctcccgt at                                                         72

<210> SEQ ID NO 307
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 307
atccgtcaca cctgctctcc ggtacgtcag gggaacgcac atttgtccac ttcatggtgt    60
tggctcccgt at                                                         72

<210> SEQ ID NO 308
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 308
atacgggagc caacaccatg aagtggacaa atgtgcgttc ccctgacgta ccggagagca    60
ggtgtgacgg at                                                         72

<210> SEQ ID NO 309
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 309
atccgtcaca cctgctctcc tcgactcgat atcacttagt ctaacactaa atggtggtgt    60
tggctcccgt at                                                         72

<210> SEQ ID NO 310
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 310
atacgggagc caacaccacc atttagtgtt agactaagtg atatcgagtc gaggagagca    60
ggtgtgacgg at                                                         72

<210> SEQ ID NO 311
<211> LENGTH: 72
<212> TYPE: DNA
<213> ORGANISM: Artificial
<220> FEATURE:
<223> OTHER INFORMATION: Synthesized Oligonucleotide Sequence
```

-continued

```
<400> SEQUENCE: 311
atacgggagc caacaccact tccactttt cgcctaattg cctgttgcat ggtaagagca    60
ggtgtgacgg at                                                       72

<210> SEQ ID NO 312
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 312
atccgtcaca cctgctctca actatattcg ccttaaagac tttaggacat cgcctggtgt    60
tggctcccgt at                                                       72

<210> SEQ ID NO 313
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 313
atacgggagc caacaccagg cgatgtccta aagtctttaa ggcgaatata gttgagagca    60
ggtgtgacgg at                                                       72

<210> SEQ ID NO 314
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 314
atccgtcaca cctgctctta ccatgcaaca ggcaattagg cgaaaaagtg aagtggtgt    60 tggctcccgt at                                                       72

<210> SEQ ID NO 315
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 315
atacgggagc caacaccacc cccccctccg tgggccgctc ccctcggccg ggccagagca    60
ggtgtgacgg at                                                       72

<210> SEQ ID NO 316
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 316
atccgtcaca cctgctctgg cccggccgag gggagcggcc cacggagggg ggggtggtgt    60
tggctcccgt at                                                       72

<210> SEQ ID NO 317
<211> LENGTH: 72
<212> TYPE: DNA
```

```
<213> ORGANISM: Artificial
<220> FEATURE:
<223> OTHER INFORMATION: Synthesized Oligonucleotide Sequence

<400> SEQUENCE: 317
atccgtcaca cctgctctcc ttcgctcgtc ttgtattgtc gttgcttcac gggatggtgt     60
tggctcccgt at                                                        72

<210> SEQ ID NO 318
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 318
atacgggagc caacaccatc ccgtgaagca acgacaatac aagacgagcg aaggagagca     60
ggtgtgacgg at                                                        72

<210> SEQ ID NO 319
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 319
atccgtcaca cctgctctgg ccccaagcgc tctgtatctg ttgaagaagt cgcgtggtgt     60
tggctcccgt at                                                        72

<210> SEQ ID NO 320
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 320
atacgggagc caacaccacg cgacttcttc aacagataca gagcgcttgg ggccagagca     60
ggtgtgacgg at                                                        72

<210> SEQ ID NO 321
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 321
atacgggagc caacaccagg aaatggtacc taagaaatga gaactttgac gcacagagca     60
ggtgtgacgg at                                                        72

<210> SEQ ID NO 322
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 322
atccgtcaca cctgctctgt gcgtcaaagt tctcatttct taggtaccat ttcctggtgt     60
tggctcccgt at                                                        72
```

```
<210> SEQ ID NO 323
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 323
atacgggagc caacaccatt aaagttaatc ttacacgttt ccgacttcca tttgagagca      60
ggtgtgacgg at                                                          72

<210> SEQ ID NO 324
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 324
atccgtcaca cctgctctca aatggaagtc ggaaacgtgt aagattaact ttaatggtgt      60
tggctcccgt at                                                          72

<210> SEQ ID NO 325
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 325
atccgtcaca cctgctctca aaggccttag ctcgtaaaac gtagacggac tccttggtgt      60
tggctcccgt at                                                          72

<210> SEQ ID NO 326
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 326
atacgggagc caacaccaag gagtccgtct acgttttacg agctaaggcc tttgagagca      60
ggtgtgacgg at                                                          72

<210> SEQ ID NO 327
<211> LENGTH: 61
<212> TYPE: DNA
<213> ORGANISM: Artificial
<220> FEATURE:
<223> OTHER INFORMATION: Synthesized Oligonucleotide Sequence

<400> SEQUENCE: 327
gatacgggag ccaacaccac ccgtatcgtt cccaatgcac tcagagcagg tgtgacggat      60
g                                                                      61

<210> SEQ ID NO 328
<211> LENGTH: 61
<212> TYPE: DNA
<213> ORGANISM: Artificial
<220> FEATURE:
<223> OTHER INFORMATION: Synthesized Oligonucleotide Sequence

<400> SEQUENCE: 328
```

-continued

```
catccgtcac acctgctctg agtgcattgg aacgatacg ggtggtgttg gctcccgtat    60
g                                                                   61
```

<210> SEQ ID NO 329
<211> LENGTH: 60
<212> TYPE: DNA
<213> ORGANISM: Artificial
<220> FEATURE:
<223> OTHER INFORMATION: Synthesized Oligonucleotide Sequence

<400> SEQUENCE: 329

```
gatacgggag ccaacaccac gttcccatac aagttactga cagagcaggt gtgacggatg    60
```

<210> SEQ ID NO 330
<211> LENGTH: 60
<212> TYPE: DNA
<213> ORGANISM: Artificial
<220> FEATURE:
<223> OTHER INFORMATION: Synthesized Oligonucleotide Sequence

<400> SEQUENCE: 330

```
catccgtcac acctgctctg tcagtaactt gtatgggaac ggtggtgtgg ctcccgtatc    60
```

<210> SEQ ID NO 331
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 331

```
atacgggagc caacaccaat aaagagcgga acttttagaa ctggatagac tcatagagca    60
ggtgtgacgg at                                                       72
```

<210> SEQ ID NO 332
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 332

```
atccgtcaca cctgctctat gagtctatcc agttctaaaa gttccgctct ttattggtgt    60
tggctcccgt at                                                       72
```

<210> SEQ ID NO 333
<211> LENGTH: 69
<212> TYPE: DNA
<213> ORGANISM: Artificial
<220> FEATURE:
<223> OTHER INFORMATION: Synthesized Oligonucleotide Sequence

<400> SEQUENCE: 333

```
atacgggagc caacaccata gtgttgggcc aatacggtaa cgtgtccttg gagagcaggt    60
gtgacggat                                                           69
```

<210> SEQ ID NO 334
<211> LENGTH: 69
<212> TYPE: DNA
<213> ORGANISM: Artificial
<220> FEATURE:
<223> OTHER INFORMATION: Synthesized Oligonucleotide Sequence

<400> SEQUENCE: 334

```
atccgtcaca cctgctctcc aaggacacgt taccgtattg gcccaacact atggtgttgg      60
ctcccgtat                                                             69
```

<210> SEQ ID NO 335
<211> LENGTH: 58
<212> TYPE: DNA
<213> ORGANISM: Artificial
<220> FEATURE:
<223> OTHER INFORMATION: Synthesized Oligonucleotide Sequence

<400> SEQUENCE: 335

```
atacgggagc caacaccaca acttgttgct gatcttatcc agagcaggtg tgacggat       58
```

<210> SEQ ID NO 336
<211> LENGTH: 59
<212> TYPE: DNA
<213> ORGANISM: Artificial
<220> FEATURE:
<223> OTHER INFORMATION: Synthesized Oligonucleotide Sequence

<400> SEQUENCE: 336

```
atccgtcaca cctgctctgg ataagatcag caacaagtta gtggtgttgg ctcccgtat      59
```

<210> SEQ ID NO 337
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 337

```
atacgggagc caacaccaat gagagcaaag atcccaggat acactaatcc ctgtagagca     60
ggtgtgacgg at                                                         72
```

<210> SEQ ID NO 338
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 338

```
atccgtcaca cctgctctac agggattagt gtatcctggg atctttgctc tcattggtgt     60
tggctcccgt at                                                         72
```

<210> SEQ ID NO 339
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 339

```
atacgggagc caacaccacc tagtgttgaa tctgaccaca agctaagtct tcggagagca     60
ggtgtgacgg at                                                         72
```

<210> SEQ ID NO 340
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 340

```
atccgtcaca cctgctctcc gaagacttag cttgtggtca gattcaacac taggtggtgt    60
tggctcccgt at                                                        72

<210> SEQ ID NO 341
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 341
atacgggagc caacaccaag cacggaaaga gggtcgcctg atagcccgcc aatcagagca    60
ggtgtgacgg at                                                        72

<210> SEQ ID NO 342
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 342
atccgtcaca cctgctctga ttggcgggct atcaggcgac cctctttccg tgcttggtgt    60
tggctcccgt at                                                        72

<210> SEQ ID NO 343
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 343
atacgggagc caacaccaag aaatgccaac acaacgacac cggtagtgct gcccagagca    60
ggtgtgacgg at                                                        72

<210> SEQ ID NO 344
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 344
atccgtcaca cctgctctgg gcagcactac cggtgtcgtt gtgttggcat ttcttggtgt    60
tggctcccgt at                                                        72

<210> SEQ ID NO 345
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 345
atacgggagc caacaccatg gtgacggacc ttgagagcaa gaccgctacg attcagagca    60
ggtgtgacgg at                                                        72

<210> SEQ ID NO 346
<211> LENGTH: 72
<212> TYPE: DNA
<213> ORGANISM: Artificial
<220> FEATURE:
```

<223> OTHER INFORMATION: Synthesized Oligonucleotide Sequence

<400> SEQUENCE: 346

```
atccgtcaca cctgctctga atcgtagcgg tcttgctctc aaggtccgtc accatggtgt    60
tggctcccgt at                                                        72
```

<210> SEQ ID NO 347
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 347

```
atacgggagc caacaccaga agaacactgc ctagaataag tggtgcaggg ccgtagagca    60
ggtgtgacgg at                                                        72
```

<210> SEQ ID NO 348
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 348

```
atccgtcaca cctgctctac ggccctgcac cacttattct aggcagtgtt cttctggtgt    60
tggctcccgt at                                                        72
```

<210> SEQ ID NO 349
<211> LENGTH: 71
<212> TYPE: DNA
<213> ORGANISM: Artificial
<220> FEATURE:
<223> OTHER INFORMATION: Synthesized Oligonucleotide Sequence

<400> SEQUENCE: 349

```
atacgggagc caacaccatt aggtggtaga ctgtaggtta cagatagccg gggagagcag    60
gtgtgacgga t                                                         71
```

<210> SEQ ID NO 350
<211> LENGTH: 71
<212> TYPE: DNA
<213> ORGANISM: Artificial
<220> FEATURE:
<223> OTHER INFORMATION: Synthesized Oligonucleotide Sequence

<400> SEQUENCE: 350

```
atccgtcaca cctgctctcc ccggctatct gtaacctaca gtataccacc taatggtgtt    60
ggctcccgta t                                                         71
```

<210> SEQ ID NO 351
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 351

```
atacgggagc caacaccatc tggcgccgac cctgtggatt gcagtcgcgg ttacagagca    60
ggtgtgacgg at                                                        72
```

<210> SEQ ID NO 352

```
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 352
atccgtcaca cctgctctgt aaccgcgact gcaatccaca gggtcggcgc cagatggtgt      60
tggctcccgt at                                                          72

<210> SEQ ID NO 353
<211> LENGTH: 69
<212> TYPE: DNA
<213> ORGANISM: Artificial
<220> FEATURE:
<223> OTHER INFORMATION: Synthesized Oligonucleotide Sequence

<400> SEQUENCE: 353
atacgggagc caacaccata gtgttgggcc aatacggtaa cgtgtccttg gagagcaggt      60
gtgacggat                                                              69

<210> SEQ ID NO 354
<211> LENGTH: 69
<212> TYPE: DNA
<213> ORGANISM: Artificial
<220> FEATURE:
<223> OTHER INFORMATION: Synthesized Oligonucleotide Sequence

<400> SEQUENCE: 354
atccgtcaca cctgctctcc aaggacacgt taccgtattg gcccaacact atggtgttgg      60
ctcccgtat                                                              69

<210> SEQ ID NO 355
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 355
atacgggagc caacaccaca gacaccgaat gagcaacaca acaacgggac ccgtagagca      60
ggtgtgacgg at                                                          72

<210> SEQ ID NO 356
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 356
atccgtcaca cctgctctac gggtcccgtt gttgtgttgc tcattcggtg tctgtggtgt      60
tggctcccgt at                                                          72

<210> SEQ ID NO 357
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 357
atacgggagc caacaccagg tatccgaccg gacacggcac tacgacctct ttgcagagca      60
```
ggtgtgacgg at                                                          72

<210> SEQ ID NO 358
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 358
atccgtcaca cctgctctgc aaagaggtcg tagtgccgtg tccggtcgga tacctggtgt      60
tggctcccgt at                                                          72

<210> SEQ ID NO 359
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 359
atacgggagc caacaccagg gttggtgtaa agtggccagc cctttacgct aagtagagca      60
ggtgtgacgg at                                                          72

<210> SEQ ID NO 360
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 360
atccgtcaca cctgctctac ttagcgtaaa gggctggcca ctttacacca accctggtgt      60
tggctcccgt at                                                          72

<210> SEQ ID NO 361
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 361
atacgggagc caacaccaca gctgacaata gaaggatatc ctgggtaccg atgcagagca      60
ggtgtgacgg at                                                          72

<210> SEQ ID NO 362
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 362
atccgtcaca cctgctctgc atcggtaccc aggatatcct tctattgtca gctgtggtgt      60
tggctcccgt at                                                          72

<210> SEQ ID NO 363
<211> LENGTH: 72
<212> TYPE: DNA
<213> ORGANISM: Artificial
<220> FEATURE:
<223> OTHER INFORMATION: Synthesized Oligonucleotide Sequence -continued

<400> SEQUENCE: 363
atacgggagc caacaccact gtgtataacc ctaacgctct atgttcgtta tgcaagagca    60
ggtgtgacgg at    72

<210> SEQ ID NO 364
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 364
atccgtcaca cctgctcttg cataacgaac atagagcgtt agggttatac acagtggtgt    60
tggctcccgt at    72

<210> SEQ ID NO 365
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 365
atacgggagc caacaccagc ccccgcctgg ttcccgcagg ccgctcgcgt cccgagagca    60
ggtgtgacgg at    72

<210> SEQ ID NO 366
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 366
atccgtcaca cctgctctcg ggacgcgagc ggcctgcggg aaccaggcgg gggctggtgt    60
tggctcccgt at    72

<210> SEQ ID NO 367
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 367
atacgggagc caacaccacg ggcgtcacta gctcagaccg tcccccgttg gtatagagca    60
ggtgtgacgg at    72

<210> SEQ ID NO 368
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 368
atccgtcaca cctgctctat accaacgggg dacggtctga gctagtgacg cccgtggtgt    60
tggctcccgt at    72

<210> SEQ ID NO 369
<211> LENGTH: 69
<212> TYPE: DNA

```
<213> ORGANISM: Artificial
<220> FEATURE:
<223> OTHER INFORMATION: Synthesized Oligonucleotide Sequence

<400> SEQUENCE: 369
atacgggagc caacaccata gtgttgggcc aatacggtga cgtgtccttg gagagcaggt    60
gtgacggat                                                            69

<210> SEQ ID NO 370
<211> LENGTH: 69
<212> TYPE: DNA
<213> ORGANISM: Artificial
<220> FEATURE:
<223> OTHER INFORMATION: Synthesized Oligonucleotide Sequence

<400> SEQUENCE: 370
atccgtcaca cctgctctcc aaggacacgt caccgtattg gcccaacact atggtgttgg    60
ctcccgtat                                                            69

<210> SEQ ID NO 371
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 371
atacgggagc caacaccaat gtcctcgtta caagaatatt tcctgttacg caccagagca    60
ggtgtgacgg at                                                        72

<210> SEQ ID NO 372
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 372
atccgtcaca cctgctctgg tgcgtaacag gaaatattct tgtaacgagg acattggtgt    60
tggctcccgt at                                                        72

<210> SEQ ID NO 373
<211> LENGTH: 69
<212> TYPE: DNA
<213> ORGANISM: Artificial
<220> FEATURE:
<223> OTHER INFORMATION: Synthesized Oligonucleotide Sequence

<400> SEQUENCE: 373
atacgggagc caacaccata gtgttgggcc aatacggtaa cgtgtccttg gagagcaggt    60
gtgacggat                                                            69

<210> SEQ ID NO 374
<211> LENGTH: 69
<212> TYPE: DNA
<213> ORGANISM: Artificial
<220> FEATURE:
<223> OTHER INFORMATION: Synthesized Oligonucleotide Sequence

<400> SEQUENCE: 374
atccgtcaca cctgctctcc aaggacacgt taccgtattg gcccaacact atggtgttgg    60
ctcccgtat                                                            69
```

<210> SEQ ID NO 375
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 375
atacgggagc caacaccagt cgtgctcact ggtcatcaat acgtcgctct gcctagagca    60
ggtgtgacgg at    72

<210> SEQ ID NO 376
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 376
atccgtcaca cctgctctag gcagagcgac gtattgatga ccagtgagca cgactggtgt    60
tggctcccgt at    72

<210> SEQ ID NO 377
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 377
atacgggagc caacaccaac tccggcccct cccattgccg tgacgtgatg gcgcagagca    60
ggtgtgacgg at    72

<210> SEQ ID NO 378
<211> LENGTH: 72
<212> TYPE: DNA
<213> ORGANISM: Artificial
<220> FEATURE:
<223> OTHER INFORMATION: Synthesized Oligonucleotide Sequence

<400> SEQUENCE: 378
atccgtcaca cctgctctgc gccatcacgt cacggcaatg ggaggggccg gagttggtgt    60
tggctcccgt at    72

<210> SEQ ID NO 379
<211> LENGTH: 72
<212> TYPE: DNA
<213> ORGANISM: Artificial
<220> FEATURE:
<221> NAME/KEY: misc_feature
<222> LOCATION: (19)...(54)
<223> OTHER INFORMATION: n is a or g or c or t
<220> FEATURE:
<223> OTHER INFORMATION: Synthesized Oligonucleotide Sequence

<400> SEQUENCE: 379
atccgtcaca cctgctctnn nnnnnnnnn nnnnnnnnn nnnnnnnnn nnntggtgt    60 tggctcccgt at    72

<210> SEQ ID NO 380
<211> LENGTH: 18
<212> TYPE: DNA
<213> ORGANISM: Artificial
<220> FEATURE:

-continued

```
<223> OTHER INFORMATION: Synthesized Oligonucleotide Sequence

<400> SEQUENCE: 380
atacgggagc caacacca                                            18

<210> SEQ ID NO 381
<211> LENGTH: 18
<212> TYPE: DNA
<213> ORGANISM: Artificial
<220> FEATURE:
<223> OTHER INFORMATION: Synthesized Oligonucleotide Sequence

<400> SEQUENCE: 381
atccgtcaca cctgctct                                            18
```

THERAPEUTIC NUCLEIC ACID-3'-CONJUGATES

CROSS-REFERENCES TO RELATED APPLICATIONS

This patent application claims priority to U.S. Provisional Application No. 61/156,765, filed Mar. 2, 2009, and U.S. Provisional Application No. 61/161,505, filed Mar. 19, 2009, and is a continuation-in-part of U.S. Non-Provisional application Ser. No. 11/735,221, filed Apr. 13, 2007, which is a continuation-in-part of U.S. Non-Provisional application Ser. No. 11/058,054, filed Feb. 15, 2005 now U.S. Pat. No. 7,910,297, which claims priority to U.S. Provisional Application No. 60/548,629, filed Feb. 27, 2004, the disclosures of which are incorporated by reference in their entirety herein.

FIELD OF THE INVENTION

The present invention relates to the field of nucleic acid-based therapeutics where nucleic acid stability and retention are improved by a 3' conjugation to a therapeutic protein. More specifically, the present invention relates to methods for production of aptamers, antisense and other nucleic acid based therapeutics that are blocked at their 3' ends. The 3' blocked nucleic acids have surprisingly increased stability, increased retention in the body, and with the judicious selection of conjugate can have additional therapeutic benefit as well.

STATEMENT REGARDING FEDERALLY SPONSORED RESEARCH

This invention was made with U.S. Government support under various SBIR contracts. The Government has certain rights in the invention.

BACKGROUND OF THE INVENTION

Aptamers, derived from the Latin aptus, meaning, 'to fit', are oligonucleotides that have a specific three dimensional shape and consequent biological activity. Aptamers are generally produced through a process named "systematic evolution of ligands by exponential enrichment" or "SELEX," which is an iterative selection and amplification process. Nucleic acids that bind to a target are selected (non-binders are simply washed away) and then subjected to a round of amplification. As this process is reiterated, tightly binding aptamers are enriched in the population, and extremely tight and specific binding between the aptamer and the target can be achieved. The reader is referred to U.S. Pat. No. 5,270,163 and the very large family of related patents for detailed SELEX protocols.

The extraordinary capacity of aptamers to bind tightly to specific targets underlines their tremendous potential as molecular therapeutics. For example, aptamers can be used to selectively target cells (such as tumor cells or pathogens) for death.

For example, U.S. Pat. No. 6,566,343 discusses the potential for aptamers directed at cell surface components of bacteria, cancer cells and parasites to activate the complement system and bring about the lysis of target cells. The patent discloses the linkage of two aptamers—one directed against the target cell and a second one against a component of the complement system (thus recruiting the complement cascade to the target cell)—to achieve complement activation and targeted cell death.

There are two distinct disadvantages to this approach. First, the aptamer-aptamer conjugates are subject to degradation from serum nucleases and second, the aptamer-aptamer conjugates are subject to rapid clearance by the kidneys. Thus, although aptamers are a powerful targeting system, in vivo nucleic acid stability remains a problem.

A Canadian team of researchers (Dougan et al., 2000) demonstrated that 3'-biotinylation of DNA significantly increased its resistance to serum nuclease activity. This was presumably due to steric hindrance and suggests that any 3' or 5' capping or nucleic acid modification should improve nucleic acid stability in vivo.

However, our research surprisingly indicates that 5'-biotinylation is not very effective against serum degradation of DNA, nor is the incorporation of 2'-Fluoro-modified deoxynucleotide triphosphates (2'F-dNTPs). Thus, the stability issue is not as simply addressed as one might predict. Hence, improved methods of stabilizing nucleic acids for in vivo therapeutic use are still needed and the invention addresses this problem.

While many researchers have utilized addition of primary aliphatic amines and other functional groups to the 3' ends of solid-phase synthetic DNA, Vaijayanthi et al. (*Indian Journal of Biochem. And Biophysics*. Vol. 40, p. 382, 2003) teach that "3'-terminal modifications are somewhat difficult to achieve, as these days, most of the syntheses are being carried out on solid supports and the 3'-hydroxyl function is inaccessible for the desired modification to be incorporated. Moreover, the 3'-hydroxyl group is not sufficiently nucleophilic for introducing modifications during post-synthesis work-up." The presently revealed invention identifies a facile means for direct attachment to the 3' ends of double-stranded PCR products, thereby eliminating the difficulty in attaching to the 3' ends of DNA oligonucleotides produced by solid-phase synthesis.

In addition to the difficulties with attachment of functional groups to the 3' ends of solid-phase synthetic single-stranded DNA oligonucleotides, the oligonucleotides are limited in length to approximately 100 bases. This problem stems from the maximal 99% coupling efficiency which causes yields to be quite low for longer oligonucleotides. Yields can be theoretically estimated as $(0.99)^n$ where n is the length of the oligonucleotide in bases. Hence, an oligonucleotide of 100 bases in length would yield $(0.99)^{100}$ or 0.366 (about 37% yield). This is a severely limiting factor for the mass production of lengthy anti-sense and artificial gene DNA conjugates. Again, the natural solution to such a problem lies in PCR which because of its enzymatic nature (using Taq DNA polymerase) is capable of synthesizing DNA amplicons that are hundreds to thousands of bases in length.

A further problem with solid-phase DNA synthesis that makes it impractical at present for large-scale industrial or pharmaceutical use is cost. A gram of solid-phase synthesized DNA can cost several thousand dollars. To deal with the problem, Vaijayanthi et al., 2003 and Pons et al. 2001 teach the strategies of reusable DNA synthesis columns and multiple synthesis columns in parallel to enhance overall productivity.

A revolutionary approach to the issue of large-scale DNA synthesis cost has been recognized by Vandalia Research Corp. which published in *Genetic Engineering and Biotechnology News* (Dutton, 2009) that it uses scaled-up PCR (via its Triathlon system) for the cost-effective mass production of 1 gram or more of DNA per machine per day. It is the primary intention of the present invention to provide a facile and cost-effective means to directly couple peptides, proteins and other useful molecules to the 3' adenine overhanging ends of PCR products made by Vandalia Research or other industrial entities to lower the cost of large-scale short and lengthy DNA-3'-conjugates for the future pharmaceutical industry.

SUMMARY OF THE INVENTION

The invention presents a novel means to conjugate nucleic acid at its 3' end to protein moieties or other large macromolecules (e.g., polyethylene glycols, nanotubes, and the like). The 3' conjugation inhibits the action of serum nucleases that would otherwise rapidly breakdown the DNA in blood, and it dramatically increases retention of the aptamers in blood, which would otherwise be rapidly filtered out by the kidneys.

Various embodiments of the invention allow for the production of aptamers, antisense and other nucleic acid-based therapeutics that are blocked at their 3' ends with therapeutic proteins and therapeutic uses for the nucleic acid-3'-conjugates. Generally speaking, double-stranded (ds)-DNA is conjugated at its 3' end, followed by conversion to single-stranded (ss)-DNA-3'-conjugates. The 3' conjugates show remarkable serum nuclease resistance and retention in the body and exhibit enhanced therapeutic efficacy as compared with the same DNA in a naked (unconjugated) form.

Various embodiments of the conjugation require the addition of adenine (A), cytosine (C), or guanine (G) to the 3' end of ds-DNA by means of various enzymes (thymine has no free primary amine group). In particular, *Thermus aquaticus* (Taq) DNA polymerase adds a 3'-A overhang during the PCR process and the template-independent enzyme terminal deoxynucleotide transferase (TdT) can add A, C, or G to the 3' end of blunt-ended ds-DNA, if only A, C, and G are supplied (i.e., no thymine is provided). In various embodiments, with TdT, the undesired complementary strand will become conjugated to the protein as well, but it will be nonfunctional and nonallergenic, because DNA is of low immunogenicity.

Free primary amines in the terminal A, C, or G's can then be used to link the DNA to a protein (or other conjugate) via a bifunctional linker with an N-hydroxy-succinimide or other suitable functionality. The conjugate is specifically added to the 3' overhang because the remainder of the DNA molecule is double-stranded and cannot participate in conjugation.

After conjugation, the ds-DNA is converted to ss-DNA by means of heating beyond the DNA's melting temperature ($T_m$) for a brief period (several minutes). Care should be taken to avoid protein denaturation during the melting step. Melting is followed by purification of the ss-DNA-3'-conjugate by chromatographic or other physical and chemical means including affinity separation methods, differential or density centrifugation, and preparative electrophoresis.

Such aptamer-3'-conjugates have a variety of applications. A key application is the targeted killing of pathogens or tumor cells. For example, if the protein moiety is human or animal C1qrs (or some portion of the complex) it will activate the complement cascade as shown herein, thus targeting the cell for destruction by the immune system. The C1qrs is delivered to the target cell by virtue of being coupled to an aptamer specific for that cell.

Alternatively, one can couple aptamers to carbon nanotubes or other types of nanotubes to bind the surface of an undesirable target cell and kill it by puncturing the cell membrane or cell wall with the attached nanotube. To be effective at killing, aptamer-3'-nanotube conjugates would require energy input via a molecular motor driven by adenosine triphosphate (ATP), creatine phosphate, or other innovative means of energetically driving the nanotube into the target cell membrane to puncture and lyse the target cell.

Another key application of aptamer-3'-conjugates is the neutralization of toxins (e.g., botulinum toxins, cholera and diphtheria toxins, digitalis, ricin, staphylococcal enterotoxins, etc.) by use of specifically developed ss-aptamers linked to serum albumin (SA) to prevent aptamer breakdown and clearance from the blood. The aptamer-3'-SA binds tightly to the toxin, thus neutralizing its effect.

Coupling of aptamers to the complement system could be advantageous in the killing of antibiotic-resistant bacteria, cancer cells, parasites and other target cells. Carbon nanotubes, toxins, and destructive enzymes might also be coupled to the 3'-end of aptamers to create highly effective and long-lived therapeutics against invading cells or target cells.

A greater understanding of the present invention may be had from reference to the following detailed description and the appended claims.

BRIEF DESCRIPTION OF THE DRAWINGS

In order that the manner in which the above recited and other advantages and objects of the invention are obtained, a more particular description of the invention briefly described above will be rendered by reference to specific embodiments thereof, which are illustrated, in the appended drawings. Understanding that these drawings depict only typical embodiments of the invention and are therefore not to be considered limiting of its scope, the invention will be described with additional specificity and detail through the use of the accompanying drawings in which:

FIG. 5. Secondary stem-loop structures of the various DNA aptamers developed against botulinum neurotoxin (BoNT) serotype A holotoxin and its enzymatic light chain. Structures were derived from Vienna RNA free energy minimization software using DNA parameters and room temperature input.

Figures 6, 7:
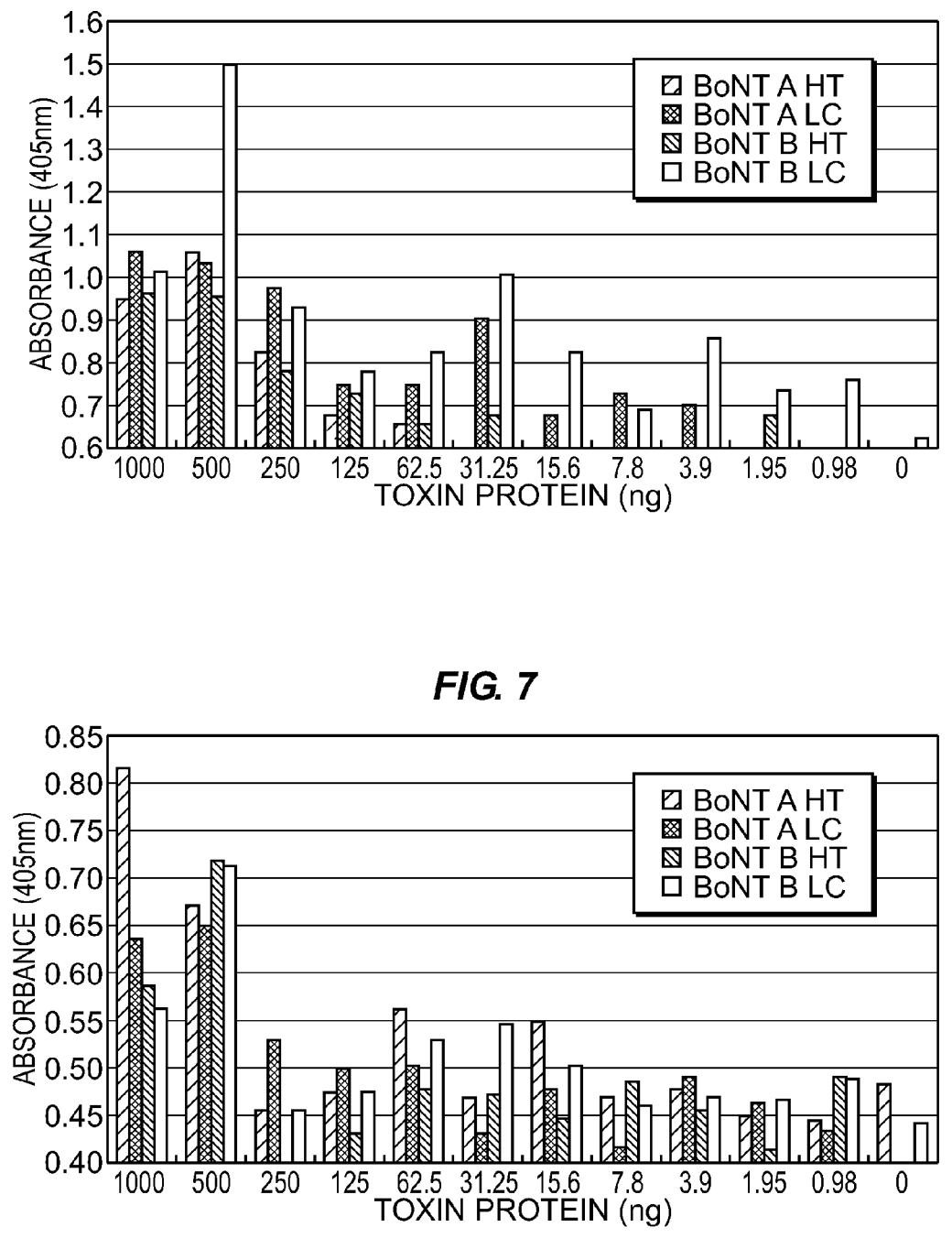

FIG. 6. Enzyme-Linked Aptamer Sorbent Assay (ELASA) results for an anti-botulinum A holotoxin-derived aptamer (SEQ ID NO 1) showing a significant level of cross-reactivity for binding of the aptamer sequence to botulinum A and B holotoxins (HT) and light chains (LC).

FIG. 7. Enzyme-Linked Aptamer Sorbent Assay (ELASA) results for an anti-botulinum A toxin light chain-derived aptamer (SEQ ID NO 2) showing a significant level of cross-reactivity for binding of the aptamer sequence to botulinum A and B holotoxins (HT) and light chains (LC).

DETAILED DESCRIPTION OF ILLUSTRATIVE EMBODIMENTS

Figure 1:
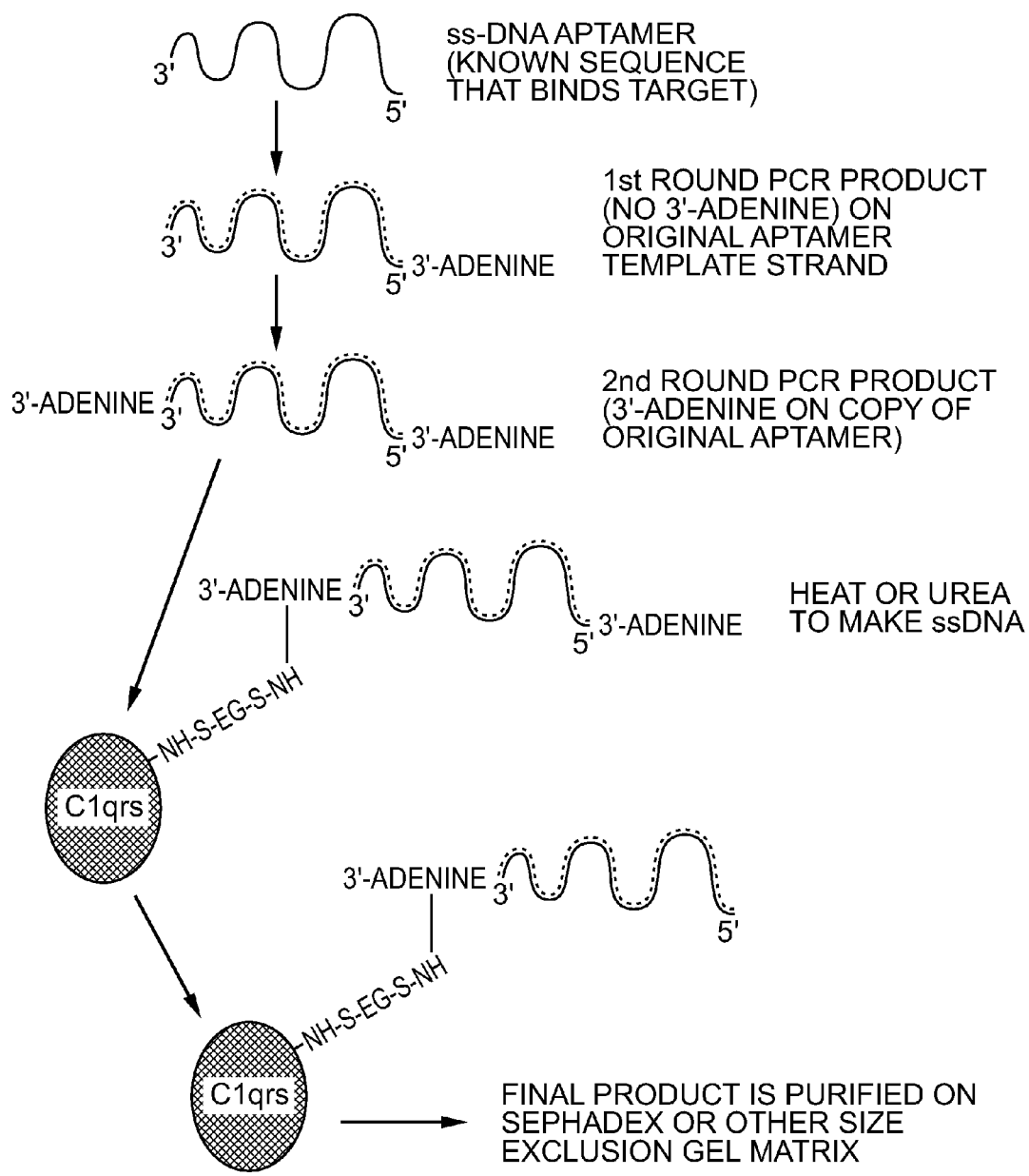
FIG. 1 shows a schematic of the process for conjugation of a known DNA aptamer sequence at its 3' end to an effector protein of choice (in this example, C1qrs to activate the complement cascade).
Figure 2:
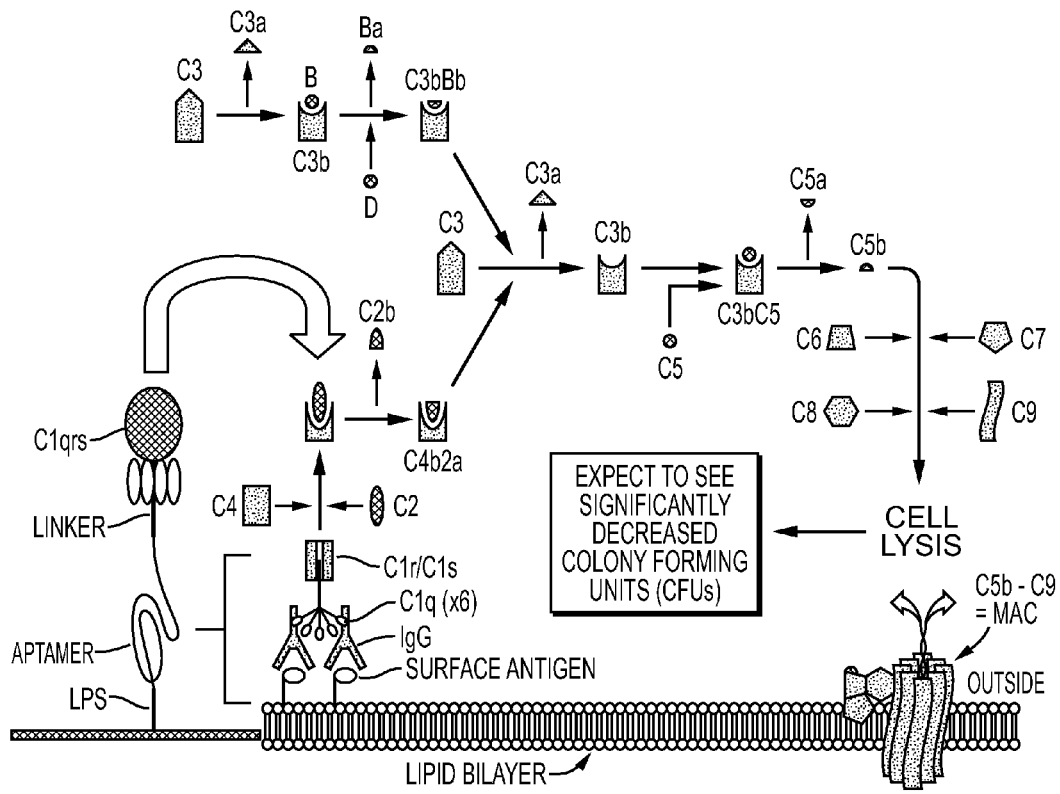
FIG. 2 shows the theoretical aptamer-3'-C1 qrs conjugate bacterial killing mechanism. In the figure, IgG antibodies are replaced by the aptamer-3'-C1qrs conjugate and activate the Classical complement cascade. Lipopolysaccharide (LPS) is shown as a target surface antigen for Gram negative bacteria, but LPS could be replaced by any bacterial cell surface component that is accessible.
Figure 3:
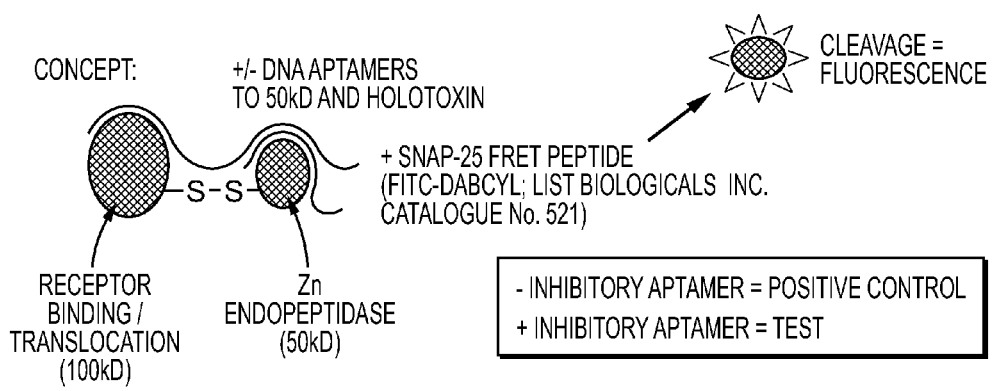
FIG. 3 illustrates how an aptamer can be used to inhibit or inactivate a toxin, such a botulinum toxin. The aptamer-3'-protein conjugate is not shown in this figure, but human serum albumin would be a good candidate for such conjugation to ensure no allergic reaction in human patients. The figure shows botulinum toxin as an example and illustrates binding and inhibition of the holotoxin and the 50 kiloDalton zinc endopeptidase subunit, which is enzymatically active on the SNAP25 peptide in neurons and is used as the basis for a fluorescence resonance energy transfer (FRET) assay known as the SNAPtide™ assay.

The references cited herein, to the extent that they provide exemplary procedural or other details supplementary to those set forth herein, are specifically incorporated by reference.

Those of skill in the art, in light of the present disclosure, will appreciate that obvious modifications of the embodiments disclosed herein can be made without departing from the spirit and scope of the invention. All of the embodiments disclosed herein can be made and executed without undue experimentation in light of the present disclosure. The full scope of the invention is set out in the disclosure and equivalent embodiments thereof. The specification should not be construed to unduly narrow the full scope of protection to which the present invention is entitled.

As used herein and unless otherwise indicated, the terms "a" and "an" are taken to mean "one", "at least one" or "one or more".

As used herein, the term "aptamer" means and refers to at least one oligonucleotide that has a specific three dimensional shape and consequent biological activity. As herein defined, "aptamer" specifically includes nucleotide sequences with, in an embodiment, about 75% sequence identity, or, in an embodiment, about 80% sequence identity, or, in an embodiment, about 85% sequence identity, or, in an embodiment about 90% sequence identity, or, in an embodiment, about 95% sequence identity, or, in an embodiment, about 99% sequence identity, or, in an embodiment, about 99.5% sequence identity with the aptamer of interest.

As used herein, the term "percent identity" describes the percentage of contiguous nucleotides in a first nucleic acid molecule that is the same as in a set of contiguous nucleotides of the same length in a second nucleic acid molecule. The term "percent complementarity" describes the percentage of contiguous nucleotides in a first nucleic acid molecule that can base pair in the Watson-Crick sense with a set of contiguous nucleotides in a second nucleic acid molecule.

Nucleic acid sequences cited herein are written in a 5' to 3' direction unless indicated otherwise. The term "nucleic acid," as used herein, refers to either DNA or RNA or a modified form thereof comprising the purine or pyrimidine bases present in DNA (adenine "A," cytosine "C," guanine "G," thymine "T") or in RNA (adenine "A," cytosine "C," guanine "G," uracil "U"). "Nucleic acid" includes the terms "oligonucleotide" and "polynucleotide" and can refer to a single-stranded molecule or a double-stranded molecule. A double-stranded molecule is formed by Watson-Crick base pairing between A and T bases, C and G bases, and between A and U bases. The strands of a double-stranded molecule may have partial, substantial or full complementarity to each other and will form a duplex hybrid, the strength of bonding of which is dependent upon at least in part on the nature and degree of complementarity of the sequence of bases.

As used herein, the term "nucleotide sequence" specifically includes the nucleotide sequence, its complement, derivatives, and homologs.

As used herein, "coordination complex" means and refers to a complex in chemistry usually is used to describe molecules or ensembles formed by the combination of ligands and metal ions.

The following examples are illustrative of various embodiments the invention and are not intended to be limiting. For example, we have exemplified the invention using aptamers, but it is equally applicable to antisense, ribozymes, gene therapy, and other therapeutic nucleic acids. Additionally, we have added the 3'-conjugate using the free primary amine of A, C, or G, which is a convenient means of specifically conjugating the 3' end, but other means of conjugation to the 3' end can be used. For example, the free carbonyl on G, T, C and U, can be used. Alternatively, a modified nucleotide equipped with target moieties for conjugation can be added as the 3' overhang. The diol on the 3'-ribose residue of RNA may be oxidized to result in two aldehyde groups using sodium meta-periodate and the aldehydes then can be conjugated to the amine groups on a protein using reductive amination with sodium cyanoborohydride. Nucleic acid conjugation techniques are well known in the art and need not be further detailed herein.

In various examples given herein, the bifunctional linker SULFO-EGS™ (PIERCE CHEMICAL CO.™) was used to couple the free primary amine from adenine to a protein moiety. However, any biocompatible, nonallergenic, bifunctional linker could be used including EDP=3-[(2-aminoethyl)dithio]propionic acid; BMPH=N-[beta-maleimidopropionic acid] hydrazide; BMPS N-[beta-maleimidopropyloxy] succinimide ester; SULFO-DST=disulfosuccinimidyl tartrate; SULFO-EMCS=N-[epsilon-maleimidocaproyloxy]sulfosuccinimide ester.

Further embodiments comprise various other linkages and/or various other techniques for linking.

In an embodiment, linkage is capable of being accomplished through metal-ion mediated catalysis of relatively non-reactive primary aryl amines in adenine, cytosine and guanine by way of transition metal ions such as, but not limited to, Pt(II) and its chelates or coordination complexes as taught by Anorbe, et al., 2004.

In an alternate embodiment, linkage is capable of being accomplished through homo- and hetero-bifunctional aldehydes, such glutaraldehyde or aminoacetaldehyde, known to spontaneously attack and bind to $N^6$ amine group of adenine as taught by Gacesa and Whish, 1978; Hopwood, 1975; Rall and Lehne, 1982; Hayatsu, et al. 1982 and many others. After attachment to the primary aryl amine in the adenine, cytosine, or guanine on the 3' end of the ds-DNA, the other end of the bifunctional aldehyde can be attached to a protein by conventional means.

In an alternate embodiment, linkage is capable of being accomplished through diazotization (Sandmeyer reaction) in which the primary aryl amine is converted into a diazo (—N=N$^+$) reactive group that links to other primary amines in proteins. In an embodiment, a diazo group is created only at the primary aryl amine of the overhanging 3' adenine, cytosine or guanine bases as taught indirectly by Matsuura, et al., 2000 and Dolan, et al., 2001.

In yet an alternate embodiment, linkage is capable of being accomplished through the use of naturally occurring enzymes such as methylases or transferases known to add ligands to the primary aryl amines of adenine, cytosine, and guanine as taught by Pues, et al., 1999; Scavetta, et al., 2000; Zinoviev, et al., 1998; Harrison, et al., 1986 and Wang, et al., 2005. In an embodiment, a bifunctional linker that is a structural analog of the normal ligand substrate is attached to the primary aryl amine of adenine, cytosine, or guanine, thereby creating a covalent bond between the base on the 3'-end of the DNA and making the other end of linker available for conjugation to a protein of choice.

In various embodiments, combinations of various linkage methods are used. In an embodiment of a combination, an aldehyde on adenine N$^6$ is capable of being followed by a diazotization of the respective linker. However, any combination is possible.

Additionally, in various embodiments protein moieties were used, because such conjugates enhance the efficacy of the invention by conferring the activity of the protein to the therapeutic nucleic acid. However, various other embodiments comprise nanotubes or other large macromolecules with desirable properties. In various embodiments, conjugates are large enough to prevent the nucleic acid-3'-conjugates from being rapidly cleared by the kidneys, and that it protect the nucleic acid from degradation, without the conjugation adversely affecting the activity of either component.

In various embodiments, where the conjugate has biocidal activity, the nucleic acid-3'-conjugate can be used to selectively target and kill pathogens or cancer cells. Biocides include toxic proteins such as peptide toxin mellitin, peroxidase, TNF-alpha, *Bacillus thuringiensis* crystal (cry) proteins, and/or the like; proteins that recruit the natural cell killing mechanisms, such as C1prs, Fc, C3b, C4b, C5a, and C567; phage lysis proteins, such as the SPOT genes 40, 50 and 51; chemicals such as polystyrenes, eugenol, thymol, trichlorocarbanalide (TCC), didecyldimethylammonium chloride (DDDMAC) and C10-16-alkyldimethyl, N-oxides (ADMAO), Pentachlorophenol (PCP), and nanotobes containing small molecule drugs, such as antibiotics, or when used as a pore to penetrate target cells.

Other conjugates are designed merely to protect the therapeutic nucleic acid from degradation and retain its activity in the bloodstream, such as serum albumin (SA), human serum albumin (HSA), alpha1 and alpha2 globulins, beta-globulins, gamma-globulins, hemoglobin, and the like. Other conjugates can include antibodies or antibody fragments, designed to recruit other proteins or cell types including cytotoxic T lymphocytes or macrophages to the therapeutic nucleic acid bound to a target cell. These are particularly useful in gene therapy techniques, such as suicide gene therapy or rescue gene therapy, where particular cells are to be targeted with a cytotoxic or functional gene.

Further embodiments of the present invention claim various applications. In an embodiment, embodiments of the present invention block organophosphorus nerve agent effects. Various nerve agents are capable of being blocked by with aptamer-3' conjugates to anti-methylphosphonic acid (MPA), acetylcholine, GA (tabun), sarin (GB), soman (GD), cyclosarin (GF), VX (a form of O-ethyl-S-[2(diisopropylamino)ethyl]methylphosphonothiolate), and/or the like. In an alternate embodiment, the aptamer-3' conjugates of the present invention are capable of use as anti-botulinum toxin antidotes. In further embodiments, the aptamer-3' conjugates of the present invention are capable of use in the opsonization and killing of pathogens such as anthrax and *Leishmania* parasites (SEQ ID NOS: 336-339), as is herein illustrated. In general, aptamer-3' conjugates of the present invention are capable of conjugation to any therapeutic agent desired.

In an embodiment of the present invention, various nucleotide sequences of at least near-perfect contiguous complementarity with the nucleotide sequences of an aptamer as disclosed in SEQ ID NOS: 1-378 are within the scope of the appended claims. "Near-perfect," as used herein, means the antisense strand of the nucleotide sequence is "substantially complementary to," and the sense strand of the nucleotide sequence is "substantially identical to" at least a portion of the aptamer. "Identity," as known by one of ordinary skill in the art, is the degree of sequence relatedness between nucleotide sequences as determined by matching the order and identity of nucleotides between the sequences. In one embodiment, the antisense strand of the nucleotide sequence having 80% and between 80% up to 100% complementarity, for example, 85%, 90% or 95% complementarity, to the target mRNA sequence are considered near-perfect complementarity and may be used in the present invention. "Perfect" contiguous complementarity is standard Watson-Crick base pairing of adjacent base pairs. "At least near-perfect" contiguous complementarity includes "perfect" complementarity as used herein. Computer methods for determining identity or complementarity are designed to identify the greatest degree of matching of nucleotide sequences, for example, BLASTN (Altschul, S. F., et al. (1990) *J. Mol. Biol.* 215:403-410).

In one embodiment of the invention, an aptamer has 72 contiguous nucleotides. Accordingly, a nucleotide sequence having 85% sequence complementarity to, or at least 85% sequence identity with, the aptamer has identical nucleotides in 61 positions of the 72 nucleotide long aptamer. Eleven (11) nucleotide substitutions (i.e., 61/72=85% identity/complementarity) are included in such a phrase.

Various embodiments of the present invention have varying degrees of sequence identity. In an embodiment, a nucleotide sequence capable of use with varying embodiments of the present invention has about 75% sequence identity with the aptamer of interest. In an alternate embodiment, a nucleotide sequence capable of use with varying embodiments of the present invention has about 80% sequence identity with the aptamer of interest. In an alternate embodiment, a nucleotide sequence capable of use with varying embodiments of the present invention has about 85% sequence identity with the aptamer of interest. In an alternate embodiment, a nucleotide sequence capable of use with varying embodiments of the present invention has about 90% sequence identity with the aptamer of interest. In an alternate embodiment, a nucleotide sequence capable of use with varying embodiments of the present invention has about 95% sequence identity with the aptamer of interest. In an alternate embodiment, a nucleotide sequence capable of use with varying embodiments of the present invention has about 99% sequence identity with the aptamer of interest. In yet an alternate embodiment, a nucleotide sequence capable of use with varying embodiments of the present invention has about 99.5% sequence identity with the aptamer of interest.

While a particular embodiment of the invention has been shown and described, numerous variations and alternate embodiments will occur to those skilled in the art. Accordingly, it is intended that the invention be limited only in terms of the appended claims.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes to the claims that come within the meaning and range of equivalency of the claims are to be embraced within their scope. Further, all published documents, patents, and applications mentioned herein are hereby incorporated by reference, as if presented in their entirety.

EXAMPLE 1

Nucleic Acid-3'-Protein Conjugation

Two prime (2') modifications of nucleotides in RNA aptamers have been reported to work well for nuclease resistance (Bell et al., 1999 and Ulrich et al., 2002) against certain specific bacterial nucleases and against serum nucleases. Some researchers claim that DNA aptamers can be protected by 2'-Fluoro-deoxynucleotide (dNTP) incorporation (Ono et al., 1997). However, there is not much definitive data on this topic in the literature. Further, it is difficult to incorporate 2'F-dNTPs into DNA by PCR (Ono et al., 1997) or other means as most DNA polymerases either will not incorporate 2'F-dNTPs (i.e., reject them as substrates or they are poorly incorporated) or the 2'-F-dNTPs are excised by the polymerase's editing function.

An alternative method for conferring resistance to serum nucleases is capping of the DNA termini, especially the 3' end as shown by Dougan et al. (2000). Dougan capped aptamers with the small molecule biotin and successfully preserved the aptamers in serum. However, we theorized that a larger peptide or protein could be conjugated to the 3' end of the aptamer with the added benefits of increasing aptamer retention in the blood (i.e., decreasing clearance by the kidneys, because the low molecular weight aptamer is attached to a large protein that cannot be filtered by the kidneys). In addition, a protein conjugate would provide the benefit of adding the functionality of the protein moiety to the aptamer. The latter advantage can then be used for adding a wide variety of functions such as biocidal activity, enzymatic activity, enhancing phagocytosis (opsonization), cell recruitment or cell activation, or serum stability.

The goal of the process shown schematically in FIG. 1 was to terminate the aptamer in a deoxynucleotide containing a free amine group at the 3' end to enable covalent coupling to the protein moiety. In an embodiment, the aptamer may or may not have a free 3' amine group originally, but conjugation of a single-stranded aptamer would surely lead to a family of conjugates at different positions on the aptamer and no guarantee of serum nuclease resistance, or retention of aptamer activity. Hence, the aptamer is subjected to at least one round of the polymerase chain reaction (PCR) to create a complementary strand (dotted line) and a 3'-adenine (A) overhang that has a free amine moiety.

In various embodiments, the 3'-A overhang is on the complementary strand, not on the desired aptamer strand. Therefore at least one more round of PCR is required to place the 3'-A overhang on the original template strand (solid line) and enable conjugation to the protein moiety by means of a common bifunctional linker such as SULFO-EGS™ (ethylene glycol-bis(sulfosuccinimidylsuccinate)). However, specifically included with this disclosure are aptamers wherein the 3'-A overhang is on the desired aptamer strand, not on the complementary strand, thereby only requiring one round of PCR.

Once the aptamer was conjugated to a given protein at its 3' end, the double strand is melted by means of heating. The conjugate is heated to a temperature and/or for a period of time that will not denature the protein. In various other embodiments, a mild chemical treatment such as low concentrations of urea, which could again denature the protein if the concentration is too high. Other means of separating ds-DNA include the use of biological tools, such as SSB (Single-stranded DNA Binding Protein).

Finally, the single-stranded aptamers and the aptamer-3'-protein conjugates can be separated by a variety of physical means such as size exclusion gel chromatography on materials such as Sephadex, density gradient centrifugation, or preparative electrophoresis, etc. The aptamer-3'-conjugate can also be separated by affinity chromatography using an antibody against the protein conjugate, and this system can be coupled with mild denaturation, thus allowing purification and separation in a combined step.

Bruno (1997) and Bruno and Kiel (2002) as well as Murphy et al. (2003) have described a method for immobilizing target molecules onto magnetic microbeads (MBs) and using these target-MBs to magnetically separate out aptamers from a randomized oligonucleotide library which bind the target with high affinity. Then using standard SELEX techniques (Bruno and Kiel 2002), a family of aptamers can be selected that will bind the target with high affinity and can be conjugated at their 3' ends by way of the process shown in FIG. 1.

EXAMPLE 2

Anti-Lipopolysaccharide (LPS; Endotoxin) Aptamer-3'-C1Q or Other Protein to Kill Gram Negative Bacteria and Bind Endotoxin During Sepsis Sulfo-EGS was dissolved at 10 mg/mL in sterile PBS and 132 µL of this stock solution added to 0.1 mg of human C1qrs protein (molecular weight of 750 kD). This ratio provided the 20-fold molar excess of Sulfo-EGS recommended for Sulfo-EGS conjugations.

One hundred µL (approximately 33 µg) of SELEX round 5 or greater DNA aptamers in their cold (double-stranded) form was added to the solution. The reactants were allowed to stand at RT for 1 hour and were then added to a Pharmacia™ PD-10 desalting column (Sephadex™ G-25) equilibrated with several void volumes of sterile PBS. Twelve to fifteen 1 mL fractions were eluted in PBS and collected as individual fractions. Absorbance readings were taken for all fractions at 260 nm and 280 nm. In addition, 5 µL of each fraction was added to 5 µL of native polyacrylamide gel electrophoresis (PAGE) loading buffer and run on 8-10% polyacrylamide gels that were fixed and silver stained to verify successful conjugation.

The following steps were performed for *E. coli* O111:K58 (B4):H— (ATCC No. 33780) killing experiments. Twenty tryptic soy agar (TSA) petri plates were warmed to RT and labeled to represent four groups of five plates each. The five plates cover arbitrary *E. coli* ten-fold dilutions from $10^{-4}$ to $10^{-8}$ where the aptamer-C1qrs conjugates "antibiotic" effect was anticipated. One loopful of freshly cultured *E. coli* O111:

K58(B4):H— (i.e., grown overnight at 35° C. on TSA agar) was added to 1 mL of Gelatin Veronal Buffer (GVB; Sigma-Aldric Co.™, St. Louis, Mo.) at RT. Clumps were broken up by use of a 5 mL syringe and 20 gauge needle that was used to vigorously eject the bacterial sample ten times to achieve a uniform single cell suspension, as confirmed by phase-contrast microscopy at 400× magnification.

This stock bacterial suspension was used to make eight ten-fold dilutions in sterile polypropylene tubes. Both the stock bacterial suspension and nascent dilution were thoroughly mixed throughout the experiments to ensure random sampling. Fifty μL of each bacterial dilution was added to four other polypropylene microfuge tubes (representing the four treatment groups for each specified dilution of interest).

Ten μL of human serum complement proteins (Sigma-Aldrich™ #S-1764) diluted 1:500 (to avoid activation of the alternate complement pathway by LPS) in GVB was added to each tube in Groups 1 and 2.

One hundred μL of the aptamer-3'-C1qrs conjugate was added to five separate PCR tubes, and all were heated at 80° C. in the thermal cycler block for 5 minutes to make the anti-LPS aptamer portion of the conjugate single-stranded (Tm of the 60mer was 78.5° C.). This temperature and duration did not appear to cause damage to the C1qrs part of the conjugate, because it still appeared to initiate bacterial killing, as shown below.

Fifty μL of the hot aptamer-C1qrs conjugate was added to Groups 1 and 4 of each killing experiment (50 μL×10 tubes=500 μL). Total volume of all tubes was equalized to 110 μL by addition of GVB as appropriate. Tubes were capped, shaken ten times, and incubated at 35° C. for 2 hours.

The tubes were decanted onto the TSA plates and the contents spread. Plates were placed face up at RT for 30 minutes and then inverted and incubated overnight at 35° C. The following day, plate counts were obtained and all plates were photographed.

It is well known that LPS from *E. coli* and other Gram negative bacteria can activate the complement cascade by the Alternate pathway. To eliminate or minimize the Alternate pathway of complement activation, a series of dilutions containing only human serum complement protein (HSCP) were added to the test bacteria to determine the lowest concentration (i.e., highest dilution) of HSCPs that did not kill significant numbers of *E. coli* bacteria by the Alternate pathway after a two hour incubation at 35° C. The results of the HSCP dilution experiment are given in Table 1 and indicate that between a 1:800 to 1:500 dilution of the HSCPs was appropriate for use in the later killing experiments, since that is where the killing effect of HSCP itself becomes apparent (i.e., significantly fewer than 300 colonies were seen per plate).

TABLE 1

Colony Counts of *E. coli* O111 as a Function of HSCP Dilution
Colony Forming Units (cfu)

| HSCP Dilution | Trial 1 | Trial 2 |
|---|---|---|
| 1:10,000 | >300 | >300 |
| 1:1,000 | 287 | 283 |
| 1:800 | 241 | 238 |
| 1:500 | 187 | 172 |
| 1:400 | 98 | 90 |
| 1:200 | 57 | 63 |
| 1:100 | 18 | 21 |

Note:
An arbitrary $10^{-4}$ dilution of *E. coli* was used. Grey indicates that at those dilutions there was sufficient complement to begin activating the alternate pathway of cell killing.

The aptamer-3'-C1 qrs-mediated killing experiments contained four treatment groups as follows:

Group 1: Full Test Group—Contained 50 μL of the bacterial dilution plus 50 μL of anti-LPS aptamer-C1qrs conjugate and 10 μL of 1:500 dilution of HSCPs per tube.

Group 2: Control for Alternate Pathway Activation—Contained 50 μL of bacterial dilution and 10 μL of 1:500 dilution of HSCPs plus 50 μL GVB per tube.

Group 3: Bacterial Growth Control—No chemical additives. This group indicates baseline growth levels of the bacteria. The group contained only 50 μL bacterial dilution and 60 μL of GVB per tube.

Group 4: Aptamer-C1qrs Conjugate Control—Contained only 50 μL of bacterial suspension plus 50 μL of aptamer-C1qrs conjugate and 10 μL of GVB (no HSCPs added, therefore the remainder of the complement cascade should not be present).

In the three aptamer-C1 qrs bacterial killing experiments (Table 2), it became clear that, at certain higher dilutions, Groups 1 and 4 consistently showed fewer colonies than Groups 2 and 3. If the classical pathway of complement activation was being invoked by the anti-LPS aptamer-C1qrs conjugate, then one would predict a significantly lower number of colonies in Group 1. However, the lower number of colonies in Group 4 (conjugate only group) is somewhat perplexing. One possible explanation of the lowered colony numbers in Group 4 is that traces or residues of the other complement proteins (HSCPs) are present in the aptamer-C1qrs conjugate preparation and synergize with the conjugate to bring about elevated levels of bacterial killing. If that is not the case, then the aptamer-C1 qrs conjugate may be able to kill bacteria by an unknown alternate mechanism that does not involve invoking the action of the complement cascade.

TABLE 2

Colony Counts from Three *E. coli* Aptamer-C1qrs Killing Experiments

| | Dilution | | | | |
|---|---|---|---|---|---|
| Group | 10e−4 | 10e−5 | 10e−6 | 10e−7 | 10e−8 |
| Experiment 1 | | | | | |
| 1 | TNTC | TNTC | 1 | 0 | 1 |
| 2 | TNTC | TNTC | 267 | 16 | 3 |
| 3 | TNTC | TNTC | 265 | 15 | 2 |
| 4 | TNTC | TNTC | 132 | 5 | 1 |
| Experiment 2 | | | | | |
| 1 | TNTC | TNTC | 141 | 13 | 0 |
| 2 | TNTC | TNTC | TNTC | TNTC | 207 |
| 3 | TNTC | TNTC | TNTC | TNTC | 216 |
| 4 | TNTC | TNTC | TNTC | TNTC | 67 |
| Experiment 3 | | | | | |
| 1 | TNTC | 199 | 34 | 4 | 0 |
| 2 | TNTC | TNTC | 167 | 55 | 2 |
| 3 | TNTC | TNTC | 155 | 74 | 3 |
| 4 | TNTC | 212 | 32 | 7 | 0 |

Note:
TNTC = Too Numerous to Count

EXAMPLE 3

Antitoxin Aptamer-3'-HSA

FIG. 3 illustrates the general concept of aptamer (or aptamer-3'-protein conjugate) binding to toxins to inhibit or inactivate the toxin. If the toxin is a small molecule that is inherently toxic to biological systems, then the binding of target-specific developed aptamers should ameliorate or eliminate toxicity by stoichiometrically wrapping around the toxin to disallow it from interacting within a biological system. If the toxin is an enzyme, then binding of a specific aptamer or aptamer-3'-protein (albumin) conjugate to the active site should diminish or cease enzymatic activity.

Figure 4A:
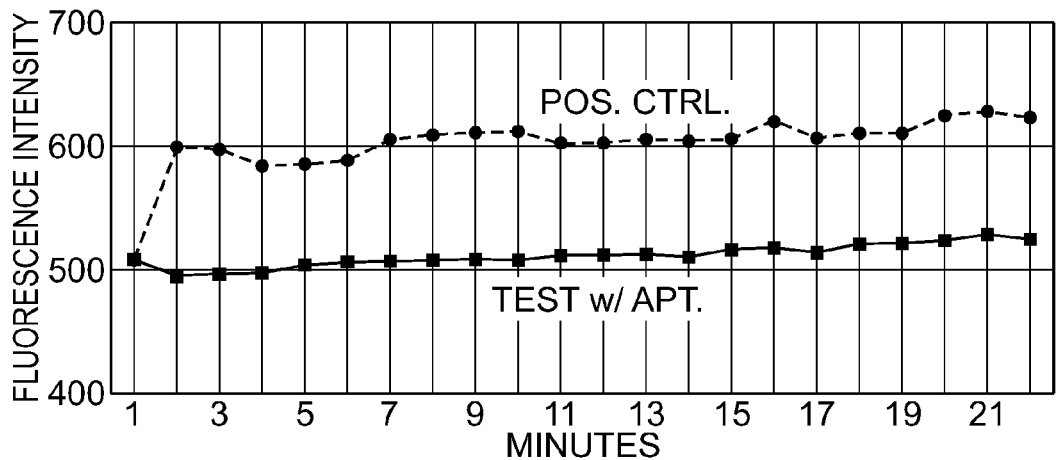
FIG. 4 shows clear inhibition (decreased light levels) of botulinum toxin serotype A (BoNT A) by DNA aptamers developed against BoNT A holotoxin (4A) and the 50 kD zinc endopeptidase subunit (4B) using the SNAPtide™ FRET assay. In the SNAPtide™ FRET assay, the greater the fluorescence intensity, the greater the BoNT A activity, because more SNAP 25 FRET substrate is cleaved.
Figure 4B:
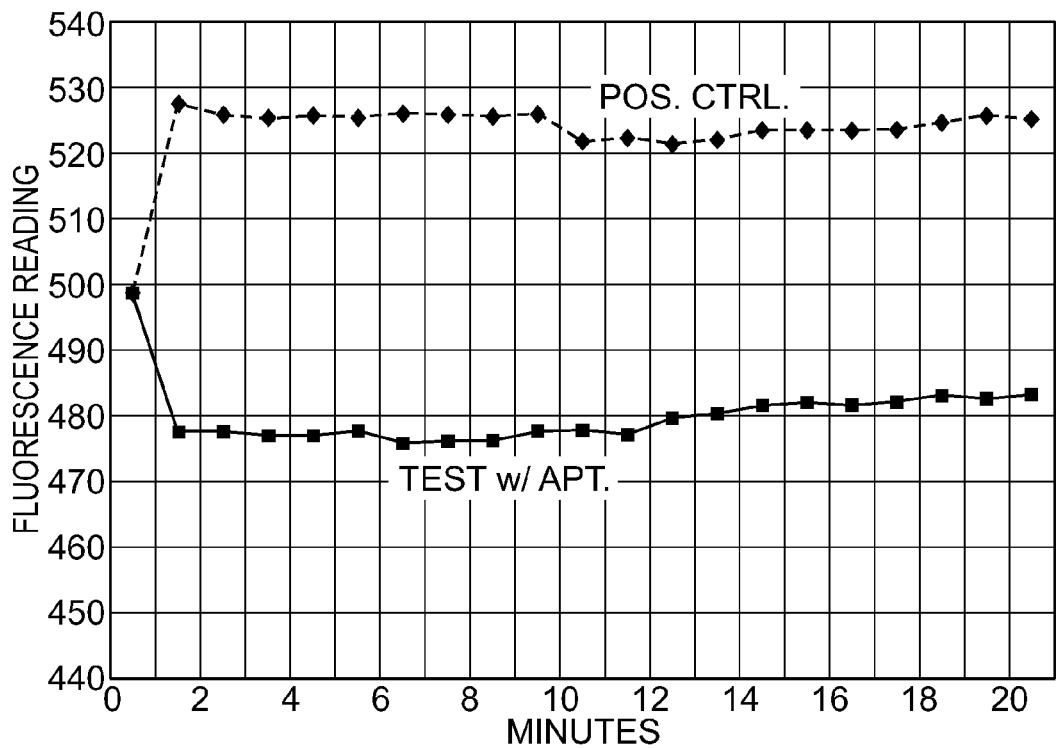
Figure 8:
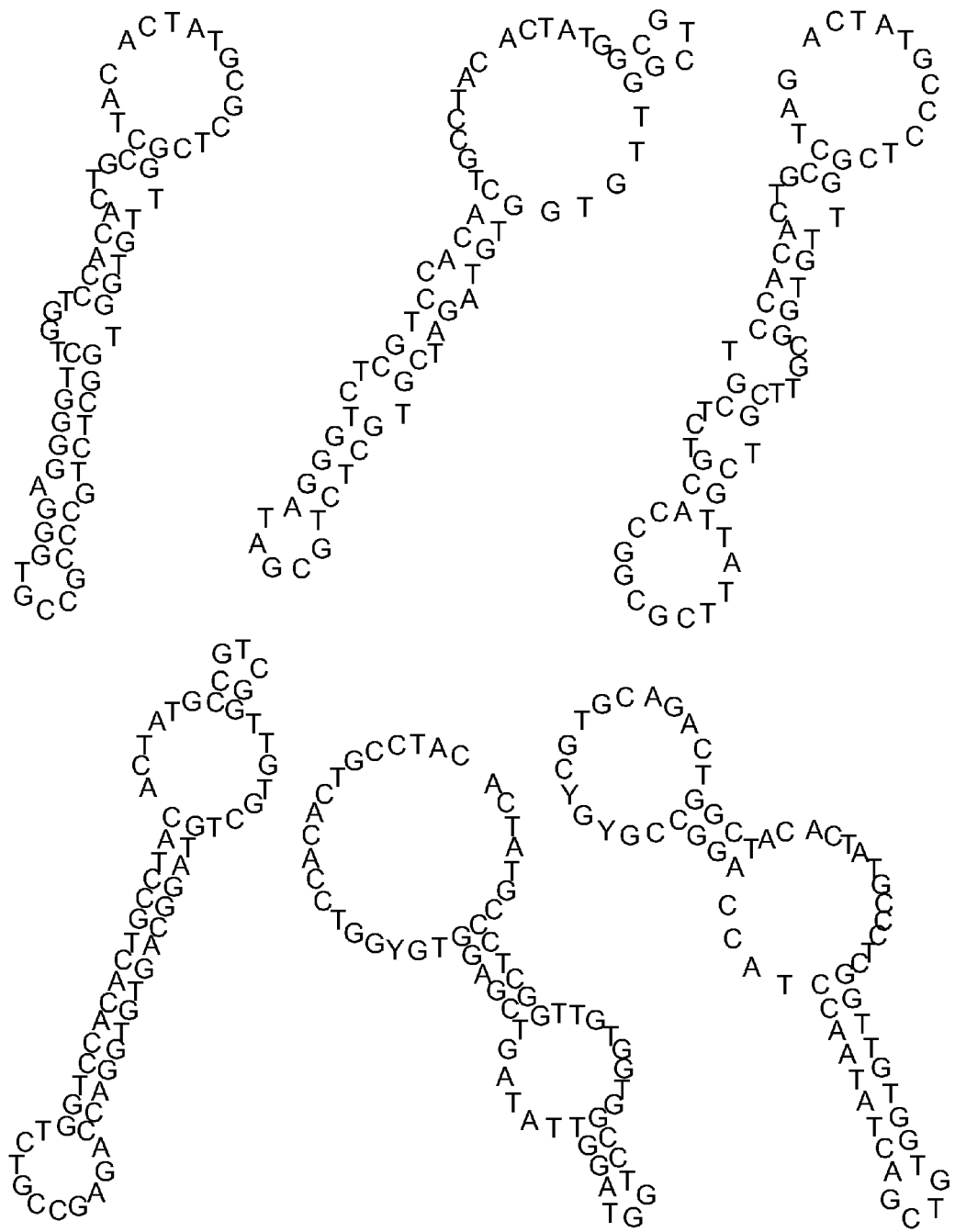
FIG. 8. Secondary stem-loop structures of DNA aptamer sequences (SEQ ID NO 3-8) known to bind *Campylobacter jejuni* surface epitopes. Structures were derived from Vienna RNA free energy minimization software using DNA parameters and room temperature input.
Figure 9:
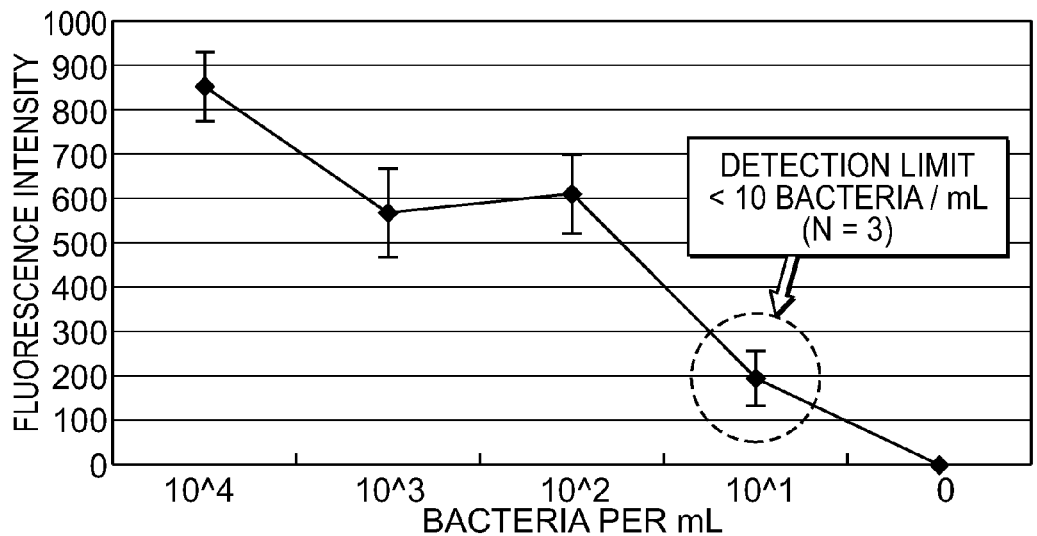
FIG. 9. Fluorescence binding curve for the best combination of DNA aptamer sequences used to detect *Campylobacter jejuni* bacteria to a level of 10 bacteria per milliliter using an immunomagnetic bead sandwich assay format referred to as the Magnetically Assisted Test Strip or "MATS." In the sandwich assay the C2 aptamer (SEQ ID NO 4) was covalently coupled to tosyl-magnetic microbeads and used to capture *C. jejuni* bacteria, followed by detection of bacterial capture with the C3 aptamer which was covalently linked to a red quantum dot (reported aptamer C3; SEQ ID NO. 5). Data points along the curve represent means of 3 independent readings and errors bars represent one standard deviation of the mean value.
Figure 10:
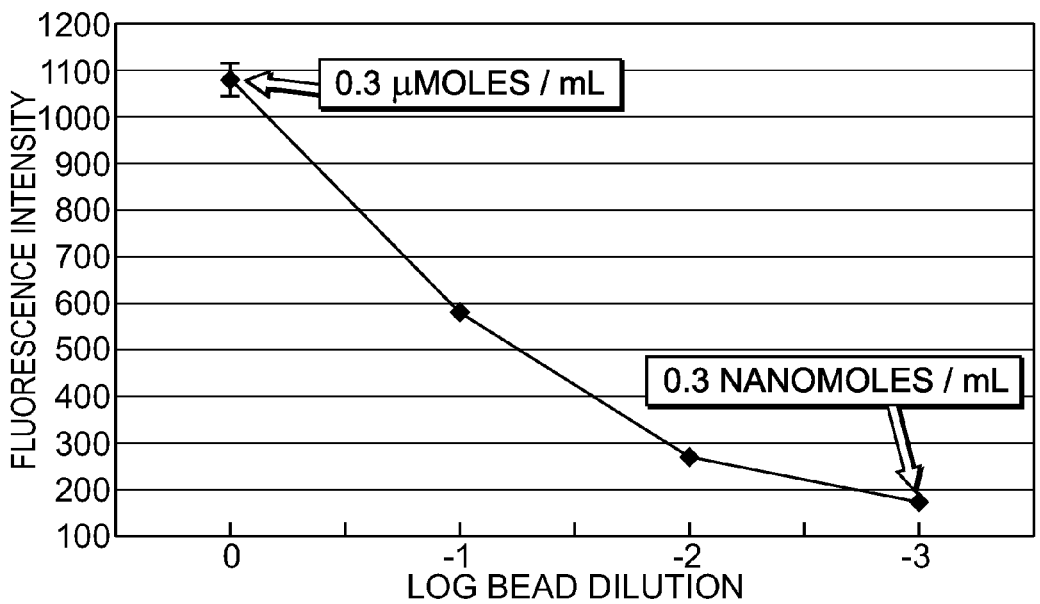
FIG. 10. Fluorescence binding curve for detection of methylphosphonic acid (MPA) bound as amino-MPA linked to tosyl-magnetic microbeads and then reacted with the anti-MPA DNA aptamer (SEQ ID NO. 31) having a 5'-fluorescein added to enable detection. Data points along the curve represent means of 3 independent readings and errors bars represent one standard deviation of the mean value.

One example of DNA aptamer-mediated enzymatic toxin inhibition can be seen in the binding of specific botulinum A toxin (BoNT A) aptamers to BoNT A, thereby inhibiting the toxin's ability to cleave its SNAP 25 peptide substrate. Using a specific SNAP 25 FRET assay known as the SNAPtide™ assay, aptamers developed against both the holotoxin and the 50 kD zinc endopeptidase subunit of BoNT A showed evidence of significant toxin inhibition as seen in FIG. 4. Thus, it is shown that conjugation to a protein did not decrease either the aptamer or the protein conjugate's activity.

The SNAPtide™ assay procedure and buffer formulations are given here. 100 mL of Buffers A and B were made in nuclease-free sterile water according to Table 3 below. The pH was adjusted to 8.0 with strong base or acid, as needed, and the solutions filter sterilized and stored in a refrigerator, but warmed to RT before use.

A SNAPtide™ vial (fluorescein/dabcyl labeled peptide; LIST BIOL. LABS,™ No. 521) was reconstituted in 80 μL of DMSO to a stock concentration of 2.5 mM. 10 μL of BoNT A (10 μg/mL) was preincubated in 190 μL of Buffer A (see composition below) at 37° C. for 30 minutes to activate the toxin.

10 μL of round 5 anti-BoNT A aptamers was added to 90 μL of Buffer B, mixed and preheated to 95° C. for at least 5 minutes in a closed Eppendorf tube under a vented chemical or biological hood.

Hot aptamer solution (100 μL) was added to 100 μL of activated BoNT A in an Eppendorf tube and allowed to bind at 37° C. for 15 minutes. This tube was labeled "Test." Similarly, 100 μL of Buffer B was added to 100 μL of activated BoNT A labeled "Control" and incubated t 37° C. for 10 minutes.

3 μL of stock SNAPtide™ (SNAP 25 FRET peptide fragment) were added to both tubes along with 2.7 mL of Buffer B. The contents of the tubes (3 mL each) were transferred to separate 10 mm methacrylate cuvettes and readings taken by spectrofluorometer with excitation at 490 nm and emission at >520 nm for the next 30 minutes in 1 to 2 minute intervals.

TABLE 3

Buffer Recipes for the SNAPtide ™ Assay Components

| Buffer | 1M HEPES | $ZnCl_2$ | 1M DTT | BSA | Tween 20 | Nuclease Free Water* |
|---|---|---|---|---|---|---|
| A | 2 mL | 4 mg | 500 μL | 100 mg | 0 | 97.5 mL |
| B | 2 mL | 4 mg | 125 μL | 0 | 100 μL | 97.775 mL |

Abbreviations: DTT = dithiothreitol, BSA = bovine serum albumin.

EXAMPLE 4

Antiviral Aptamer-3'-HSA Conjugates

In this example, aptamers coupled to human serum albumin (HSA) at their 3' ends are stabilized in serum and in vivo in order to bind the surface proteins, peptides, or saccharide epitopes on the envelopes or capsids of pathogenic viruses and prevent their attachment to target cells or limit their transmission between cells in vivo and thereby limit their replication and spread internally and between humans. Examples of DNA aptamer sequences that bind the tick-borne virus known to cause Crimean-Congo Hemorrhagic Fever (CCHF) with mortality as high as 80% are identified in SEQ ID Nos. 469-516.

EXAMPLE 5

Aptamer-3'-Fc or Aptamer-3'-C3b Conjugate

If aptamers are conjugated at their 3' end to the Fc fragment of IgG antibodies or the C3b component of complement, they could conceivably be used to opsonize encapsulated bacteria. To test this contention, tosyl-MBs (Dynal Corp.) were conjugated to poly-D-glutamic acid (PDGA) as previously described by Bruno and Kiel (2002). PDGA is the major component of the capsule of *Bacillus anthracis* (anthrax) pathogenic strains, which enables the vegetative cells to escape phagocytosis. PDGA-conjugated MBs were used to emulate vegetative anthrax bacteria and determine if aptamer-3'-Fc conjugates could enhance the phagocytosis of PDGA-MBs and by inference, opsonize encapsulated bacteria. The following describes the protocols used in these experiments.

RAW264.7 murine macrophages were split by scraping and add $10^5$ cells into each well of a sterile six-well culture plate using fresh RPMI-1640 cell culture medium plus 10% fetal bovine serum (FBS). In practice, 1 mL of cell suspension was used with 4 mL of fresh RPMI-1640 plus 10% FBS. The plate sat overnight to allow the cells to attach.

Five different tubes were labeled per Table 4 as follows (all volumes in μL):

TABLE 4

Tube Contents for Aptamer-C1q Experiments

| Rd 5 Apt* | — | — | 20 | — | — |
|---|---|---|---|---|---|
| Fc-Apt* | — | — | — | 20 | 20 |
| 2 X BB | 50 | 50 | 30 | 30 | 30 |
| Final Volume | 60 | 60 | 60 | 60 | 60 |

*Note:
Round 5 aptamer heated at 95° C. for 5 minutes prior to adding to tube; Apt. = aptamer, Fc-Apt conjugate heated at 65° C. for 5 minutes prior to adding to tube. Heating is performed to ensure single-strandedness of the aptamers before they bind PDGA. 2XBB = 2X aptamer binding buffer (Bruno and Kiel, 2002).

Each tube was incubated for 30 minutes at RT to allow binding of any aptamers or aptamer-Fc conjugates with PDGA-MBs or other targets to occur Tube contents were loaded to the appropriate wells of a 6-well plate, and incubated at 37° C. and 5% $CO_2$ and then counted at 1, 2, and 24 hours using an inverted microscope.

Data were evaluated using a "phagocytic index" parameter. The formula used for the phagocytic index according to Welkos et al., 2001 was:

Phagocytic Index=Mean number of *MBs*/cell *X*% of cells with at least one *MB*

Table 5 summarizes the raw data from the opsonization studies, as well as the phagocytic indices, which were derived from the above equation using the raw data. The controls that appeared to show enhanced phagocytosis may be due to some nonspecific binding of the aptamers to other targets or the innate ability of macrophages to recognize certain types of foreign matter (MBs or coated MBs). It also appears from Table 5 that there was some dose-dependence to the Fc-aptamer enhancement because in the first experiment the percentage of cells showing phagocytosis jumped from 74.67% to 96% with an increased level of Fc-aptamer conjugate (see highlighted data in Table 5).

TABLE 5

Raw Data and Phagocytic Indices for All Macrophage Studies in Phase I

Macrophage Test No. 1: 24 hr. Count

| Well | # of cells counted | # w/o MB association | # of MB | Mean # of MB per Cell | % cell w/MB | Phagocytic Index |
|---|---|---|---|---|---|---|
| Blank (2XBB) | 300 | 300 | 0 | 0 | 0.00% | 0.00 |
| 5 uL Tosyl-MBs | 300 | 138 | 416 | 1.39 | 54.00% | 0.75 |
| 50 uL PDGA-MB + FcApt | 300 | 12 | 586 | 1.95 | 96.00% | 1.88 |
| 5 uL PDGA + FcApt | 300 | 76 | 402 | 1.34 | 74.67% | 1.00 |

Macrophage Test No 2: 1 hr. Count

| Well (total volume added 30 uL) | # of cells counted | # w/o MB association | # of MB | Mean # of MB per Cell | % cell w/MB | Phagocytic Index |
|---|---|---|---|---|---|---|
| Blank (2XBB) | 300 | 300 | 0 | 0 | 0.00% | 0.00 |
| Tosyl-MBs | 300 | 273 | 52 | 0.17333333 | 9.00% | 0.02 |
| PDGA-MBs | 300 | 272 | 67 | 0.22 | 9.33% | 0.02 |
| Tosyl + FcApt | 300 | 218 | 139 | 0.46 | 27.33% | 0.13 |
| PDGA + FcApt | 300 | 187 | 243 | 0.81 | 37.67% | 0.31 |

| Well (total volume added 60 uL) | # of cells counted | # w/o MB association | # of MB | Mean # of MB per Cell | % cell w/MB | Phagocytic Index |
|---|---|---|---|---|---|---|

Macrophage Test No. 3: 1 hr. Count

| Blank | 300 | 300 | 0 | 0.00 | 0.00% | 0.00 |
| 2-Tosyl | 300 | 246 | 83 | 0.28 | 18.00% | 0.05 |
| 3-PDGA | 300 | 246 | 116 | 0.39 | 18.00% | 0.07 |
| Tosyl + FcApt | 300 | 252 | 116 | 0.39 | 16.00% | 0.06 |
| PDGA + FcApt | 300 | 206 | 195 | 0.65 | 31.33% | 0.20 |

Macrophage Test No. 3: 2 hr. count

| Blank (2XBB) | 300 | 300 | 0 | 0.00 | 0.00% | 0.00 |
| Tosyl | 300 | 186 | 512 | 1.71 | 38.00% | 0.65 |
| PDGA | 300 | 158 | 256 | 0.85 | 47.33% | 0.40 |
| Tosyl + FcApt | 300 | 212 | 264 | 0.88 | 29.33% | 0.26 |
| PDGA + FcApt | 300 | 136 | 498 | 1.66 | 54.67% | 0.91 |

Macrophage Test No. 3: 24 hr. count

| Blank (2XBB) | 300 | 300 | 0 | 0.00 | 0.00% | 0.00 |
| Tosyl-MB | 300 | 44 | 676 | 2.25 | 85.33% | 1.92 |
| PDGA-MB | 300 | 53 | 628 | 2.09 | 82.33% | 1.72 |
| Tosyl + FcApt | 300 | 92 | 854 | 2.85 | 69.33% | 1.97 |
| PDGA + FcApt | 300 | 52 | 804 | 2.68 | 82.67% | 2.22 |

Figure 5:
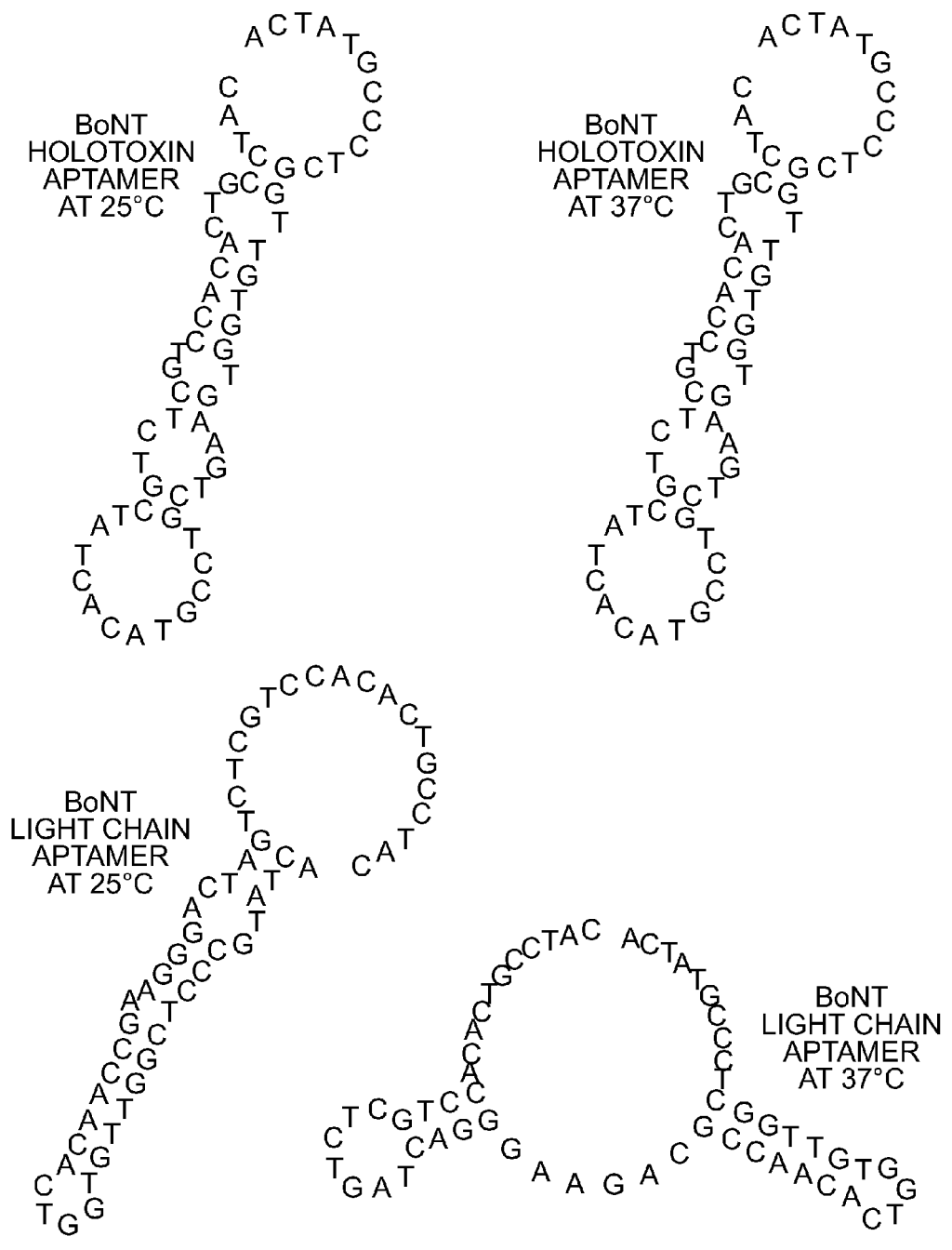

All appended aptamer sequences were generally collected from embodiments of the following procedure: Developing DNA aptamer families to diazinon and malathion by the SELEX (as disclosed in U.S. Pat. No. 5,270,163 cited herein) process. Each of the targets diazinon and malathion has a different attachment chemistry for immobilization. Immobilization is a factor to affinity selection of aptamers from a random library of sequences. Various embodiments of an immobilization approach are outlined in Table 6 below. FIG. 5 demonstrates the basic steps in the aptamer selection process using a bead-immobilized target.

The general magnetic bead (MB)-based SELEX approach of Bruno and Kiel 2002 consisting of alternating iterative phases of affinity selection and PCR amplification was used to eventually yield a set of high-affinity aptamers after 5-12 rounds of selection in all cases.

TABLE 6

Immobilization strategies for each of the aptamer targets

| Target Molecule(s) | Immobilization Strategies | Notes |
|---|---|---|
| p-aminophenol-soman | Diazo or tosyl-mediated coupling to derivatized magnetic beads (MBs) | Ref: Johnson, Cerasoli, and Lenz 2005. OpTech has filed a "research proposal" with USAMRICD (MAJ Maurice Sipos) to complete this task. |
| Amino-MPA | Attaches directly to tosyl-MBs | Amino-MPA is readily available from Aldrich Chemical Co. |

TABLE 6-continued

Immobilization strategies for each of the aptamer targets

| Target Molecule(s) | Immobilization Strategies | Notes |
|---|---|---|
| Acetylcholine, Diazinon, and Malathion | Mannich condensation reaction—due to the lack of functional groups, Mannich chemistry is needed | PharmaLink Columns have been purchased from Pierce Chemical Co. |
| DFP | Phosphonate ester formation with —OH groups on glycerol-glass beads | DFP was obtained from Sigma Chemical Co. and it attaches directly to alcohols such as the side chain of serine |
| MPA, IMPA, and PMPA | Mannich or Mitsunobu ester formation | Ref: Campbell and Bermak, 1994 |

Aptamer Selection Protocol for Magnetic Bead-Immobilized Target Molecules

1. SELEX DNA template (72mer; see Table below) is reconstituted in 1 mL of nuclease-free water. Five hundred μL of this template solution (160-180 nanomoles of DNA) is heated to 95° C. for 5 minutes to ensure that the DNA library is single-stranded (ss).
2. The hot template solution is added to 100 μL of target-MBs ($2 \times 10^7$ MBs) with 600 μL of 2× binding buffer (2XBB; 1M NaCl, 20 mM Tris HCl and 2 mM $MgCl_2$ in nuclease-free deionized sterile water with filter sterilization; pH 7.2-7.4).
3. The DNA library-target-MB suspension (1.2 mL) is mixed in a sterile polypropylene tube at room temperature (RT) for 1 hour.
4. Target-MBs with any bound DNA (round 1 aptamers) are pelleted by use of a strong permanent magnet and, if necessary, a centrifuge.
5. The DNA-target-MBs are washed three times in 0.4 mL of sterile 1XBB (2XBB diluted 1:1 in sterile nuclease-free water).
6. Following the third wash, the MB pellet (about 75 μL) is used in a PCR reaction to amplify the bound DNA as follows: The MB pellet is split into 15 μL aliquots and added to five Molecular BioProducts, Inc. (MBP, San Diego, Calif.) "Easy Start Micro 50" tubes (Catalogue No. 6020, which contain most of the nonperishable components of a PCR reaction beneath a wax seal). Three uL of 1:10 primer mix (10% primer 1 plus 10% primer 2 by volume in nuclease-free deionized water or approximately 20 nanomoles of each primer per mL; Table) plus 2 μl (10 Units) of Taq DNA polymerase and 5 uL of 20 mM $MgCl_2$ are added to each of the five tubes.
7. PCR is carried out on a Perkin-Elmer GeneAmp 2400 or other suitable thermal cycler. Tubes are subjected to an initial 95° C. phase for 5 minutes followed by 20-40 cycles of 1 minute at 95° C., 1 minute at 53° C., and 1 minute at 72° C. followed by a 72° C. completion phase for 7 minutes and refrigeration at 4° C. This constitutes the first round of SELEX.
8. Ten μL of PCR product from one of the five tubes was used per round for agarose gel electrophoresis to verify the presence of the correct length (72 base) PCR product. Ten μL of PCR product is mixed 1:1 with 5× loading buffer (BioRad, Hercules, Calif.) and loaded into a 2% agarose submarine gel with 2 μL of 10 mg/ml ethidium bromide per 45 mL gel and run at 100V in cold 1×TBE (Tris-Borate-EDTA; BioRad) buffer with 5-10 μL of DNA ladder standard (BioRad) mixed 1:1 with loading buffer.
9. To begin the second round and all subsequent rounds, four complete tubes of the five original PCR tubes are heated to 95° C. for 5 minutes to release all bound DNA (aptamers) from the target protein-MBs. Heating is accomplished in the thermal cycler. The fifth tube is always retained as a backup to the SELEX process and refrigerated.
10. All available DNA is siphoned out of the hot tubes while the tubes sit in the thermal cycler block. Generally about 25 μL of fluid can be siphoned per tube (100 μL from four tubes) without removing the MBs.
11. The 100 μL of hot DNA is added to 100 μL of fresh target protein-MBs ($2 \times 10^7$ MBs) in 200 μL of 2XBB and allowed to mix for 1 hour at RT as in step 3 above, and the process is repeated from that point for the remaining rounds of SELEX. At least four more rounds should be accomplished.

TABLE 7

SELEX Aptamer Template and Primer System Used

| Component | Sequence |
|---|---|
| Template | ATCCGTCACACCTGCTCT-N36-TGGTGTTGGCTCCCGTAT (SEQ ID NO: 379) |
| Primer 1 (Forward) | ATACGGGAGCCAACACCA (SEQ ID NO: 380) |
| Primer 2 (Reverse) | ATCCGTCACACCTGCTCT SEQ ID NO: 381) |

Notes:
All sequences are shown 5' to 3' from left to right and "N" indicates the randomized region (36 bases long) wherein an equal (25%) chance exists for the base to be A, C, G, or T. All DNA is obtained from Integrated DNA Technologies, Inc. (IDT; Coralville, IA).

PharmaLink™ Column Immobilization for OP Pesticides

Ligand Coupling

1. Equilibrate a 2 mL PharmaLink gel column (Pierce Chemical Co., Rockford, Ill.) to room temperature (RT) or body temperature (37° C.) as appropriate for aptamer selection. Therapeutic aptamers should generally be selected at 37° C.
2. Remove the top cap and bottom cap sequentially. Remove the caps in this order to prevent the incorporation of bubbles in the gel.
3. Place the column in a sterile 50 mL conical tube.
4. Drain the storage solution.
5. Equilibrate the column with 2×2 mL of 1:3 ethanol: Coupling Buffer and let each aliquot flow through.
6. Replace bottom cap.
7. Dissolve ligand in pure ethanol to its limit of solubility. Notes: Pierce Chemical Co. stated that 1 mL of PharmaLink gel has 16-20 μmoles of amine linkers per mL of gel. This means that a 2 mL gel can hold 32-40 μmoles of ligand. For Diazinon (MW=304.36), the maximum amount per column would be 12.2 mg and for Malathion (MW=330.35), the maximum per column would be 13.2 mg. Hence, dissolve these amounts in 1 mL of pure ethanol and add 3 mL of coupling buffer.

8. Add the ligand solution to the column.
9. Add 200 µL of Coupling Reagent to the column.
10. Resuspend the gel by stirring with a sterile Pasteur pipette or other rod-like instrument.
11. Transfer the gel slurry to a reaction tube and discard the column.
12. Cap the reaction tube. React at 37° C. in the bacterial incubator for a minimum of 24 hrs. Resuspend by stirring periodically.

Transfer Gel Slurry to a New Column 11. Apply bottom cap to an empty column.
2. Add NFW to column until it nearly reaches the top.
3. Set frit on top of NFW and use inverted serum separator to position frit into the bottom of the column.
4. Decant NFW from the column.
5. Resuspend the coupled gel in the reaction tube by swirling and add to the new column.

Column Washing
1. Wash non-coupled ligand from the column with 48 mL of 1:3 ethanol:PharmaLink Wash Buffer (i.e., 12 mL of ethanol added to 36 mL of Wash Buffer).
2. Set top frit in column and slide to within 1 mm of the top of the gel bed.
3. Cap and refrigerate the column until used. Do NOT add azide as this may react with the ligand.

Aptamer Generation Using PharmaLink™ Columns
1. Reconstitute DNA template ($\geq$160 nanomoles of 60mer in 1 mL of 1× binding buffer (1XBB: 0.5M NaCl, 10 mM Tris HCl and 1 mM $MgCl_2$ in nuclease-free deionized sterile water (NFW), pH 7.2-7.4). See Bruno & Kiel, 2002.
2. Heat the 1 mL of template solution at 95° C. for 5 minutes to ensure DNA is single-stranded.
3. Equilibrate a Pierce PharmaLink™ column (Cat. No. 44930) with immobilized target molecules in it with 6 mL of 1XBB. See separate SOP for PharmaLink™ immobilization.
4. Add hot DNA library to the column, allow it to percolate through and bind for 1 hour at room temperature (RT). Note: 1 mL is the void volume of the column and will therefore expel exactly the correct amount of fluid to fill the length of the column with the DNA template solution. Stop the column flow by capping it when the DNA solution has completely entered the column and the top of the column just turns dry.
5. Wash unbound DNA out of column in a total of 16 mL of 1XBB.
6. Cap the column exit port and pre-heat the column to 60° C. in an incubator or water bath for 10-15 minutes.
7. Elute bound DNA by addition of 1 mL volume of 3M sodium acetate at pH 5.2, which is allowed to interact with the column for 10 minutes by stopping the flow after the 3M sodium acetate has percolated fully into the column bed. Note: Hot nuclease free water failed to liberate much DNA from the column and 0.3M sodium acetate at pH 5.2 can be used, but it is much less efficient and requires much higher volumes (8-12 mL).
8. Elute the DNA with an additional 1 mL of 1XBB added to the top of the column. Thereafter, flush the column liberally with 1XBB, cap and store in the refrigerator.
9. Obtain $A_{260nm}$ of the eluted DNA fractions. Absorbance readings of the eluate at 260 nm should generally be >0.100.
10. Prepare primer-conjugated magnetic microbeads (MBs) by heating 400 uL (approximately 12 to 50 ug) of each the 5'-biotinylated 18mer SELEX primers (forward and reverse or primers 1 and 2) described below to 95° C. for 5 min and adding the hot biotinylated primers to 800 uL (8 mg) of Dynal streptavidin-coated M280 (2.8 um diameter) MBs.
11. Collect the primer-MBs with a strong permanent magnet and wash them several times in 1-2 mL volumes of 1XBB.
12. Reconstitute the primer-MBs in 1 mL of 1XBB and add 100 µL to the 20 mL of diluted DNA eluted from the column. This process is referred to as "fishing" for DNA aptamers.
13. Mix the primer-MBs with the 20 mL of eluted DNA for 2 hrs at room temperature
14. Collect the DNA-primer-MBs by means of a strong permanent magnet.
15. Reconstitute the DNA to 75 µL with NFW.
16. Add 15 µL reconstituted DNA to each of 5 Easy Start Micro 50™ tubes, plus 3 µL primer mix (1:10 each 5'-biotin-primer in NFW), 2 µL (10 U) of Takara ExTaq™ or other Taq DNA polymerase, 5 µL 20 mM $MgCl_2$, and enough NFW to bring each tube's total volume to 50 µL.
17. Perform 40 cycles of PCR amplification per the following profile:
    i. 5 min @ 95° C., (40 cycles of: 1 min @ 95° C., 1 min @ 53° C., and 1 min @ 72° C.), 7 min @ 72° C. and hold @ 4° C.
    ii. This constitutes the first round of SELEX.
18. Use 10 µL of PCR product from one tube to verify correct length (60 base) by agarose gel electrophoresis. Mix 10 µL of PCR product in 1:1 ratio with 5× loading buffer (BioRad) and load into 2% agarose submarine gel (containing 2 µL of 10 mg/mL ethidium bromide per 45 mL gel). Run electrophoresis at 100V in cold 1×TBE buffer (Tris-Borate-EDTA; BioRad) with 5 µL DNA ladder standard mixed 1:1 with 5× loading buffer.
19. To begin second and all subsequent rounds, heat two of five PCR tubes from previous round to 95° C. for 5 minutes (retain other tubes as a back-up).
20. Aspirate 100 µL hot ssDNA out of tubes (which remain in thermal cycler heat-block) and add to 900 µL of 1XBB.
21. Heat the 1 mL of DNA solution to 95° C. for 5 minutes.
22. Add hot DNA to column and repeat steps 4-17 for the remaining rounds of SELEX (4-5 rounds minimum should be attempted).
23. If columns do not appear damaged, they may be reused. Therefore, rinse the column with at least 10 mL of 1XBB and store at 4° C. until needed again.

Aptamer DNA Sequences and SEQ ID Nos.

The following Aptamer clones were identified as disclosed herein following the sequences. All of the following sequences are listed from 5' to 3'. Sequences are listed for various classes of therapeutic targets including bacterial and viral pathogens of man and animals, biotoxins (such as LPS endotoxin and *E. coli* Shiga toxins), organophosphorus nerve gas agents such as soman and its methylphosphonic acid core, and pesticides.

Anti Botulinum Toxin A and B Aptamers Developed Against the Holotoxins (HT) and Light Chains (LC):

| Aptamer Clone | DNA sequence |
|---|---|
| BoNT A/B HT | CATCCGTCACACCTGCTCTGCTATCACATGCCTGCTGAAGTGGTGTTGGCTCCCGTATCA (SEQ ID NO: 1) |
| BoNT A/B LC | CATCCGTCACACCTGCTCTGATCAGGGAAGACGCCAACACTGGTGTTGGCTCCCGTATCA (SEQ ID NO: 2) |

*Campylobacter jejuni* MgCl$_2$-Extracted Surface Antigen Aptamer Sequences

| Aptamer Clone | DNA sequence |
|---|---|
| *Campylobacter jejuni* | CATCCGTCACACCTGCTCTGGGGAGGGTGGCGCCCGTCTCGGTGGTGTTGGCTCCCGTATCA (SEQ ID NO: 3) |
| *Campylobacter jejuni* | CATCCGTCACACCTGCTCTGGGATAGGGTCTCGTGCTAGATGTGGTGTTGGCTCCCGTATCA (SEQ ID NO: 4) |
| *Campylobacter jejuni* | CATCCGTCACACCTGCTCTGGACCGGCGCTTATTCCTGCTTGTGGTGTTGGCTCCCGTATCA (SEQ ID NO: 5) |
| *Campylobacter jejuni* | CATCCGTCACACCTGCYCTGGAGCTGATATTGGATGGTCCGGTGGTGTTGGCTCCCGTATCA (SEQ ID NO: 6) |
| *Campylobacter jejuni* | CATCCGTCACACCTGCYCYGCCCAGAGCAGGTGTGACGGATGTGGTGTTGGCTCCCGTATCA (SEQ ID NO: 7) |
| *Campylobacter jejuni* | CATCCGTCACACCTGCYCYGCCGGACCATCCAATATCAGCTGTGGTGTTGGCTCCCGTATCA (SEQ ID NO: 8) |

Poly-D-Glutamic Acid (PDGA) *B. anthracis* Capsular Antigen Aptamer Sequences:

| Aptamer Clone | DNA sequence |
|---|---|
| PDGA 2 M13F | CATCCGTCACACCTGCTCTGGTTCGCCCCGGTCAAGGAGAGTGGTGTTGGCTCCCGTATC (SEQ ID NO: 9) |
| PDGA 2 M13R | GATACGGGAGCCAACACCACTCTCCTTGACCGGGGCGAACCAGAGCAGGTGTGACGGATG (SEQ ID NO: 10) |
| PDGA 5 M13F | CATCCGTCACACCTGCTCTGGATAAGATCAGCAACAAGTTAGTGGTGTTGGCTCCCGTATC (SEQ ID NO: 11) |
| PDGA 5 M13R | GATACGGGAGCCAACACCACTAACTTGTTGCTGATCTTATCAGAGCAGGTGTGACGGATG (SEQ ID NO: 12) |

All of the following sequences are listed from 5' to 3'. In the following, A is acetylcholine, D is diazinon, M is malathion. Only the M13 plasmid forward sequences are shown. However, the M13 reverse sequences are capable likewise as aptamers in each case.

| Aptamer Clone | DNA Sequence |
|---|---|
| A25a | ATACGGGAGCCAACACCA-TCATTTGCAAATATGAATTCCACTTAAAGAAATTCA-AGAGCAGGTGTGACGGAT (SEQ ID NO: 13) |
| A25b | ATCCGTCACACCTGCTCT-TGAATTTCTTTAAGTGGAATTCATATTTGCAAATGA-TGGTGTTGGCTCCCGTAT (SEQ ID NO: 19) |
| D12a | ATACGGGAGCCAACACCA-TTAAATCAATTGTGCCGTGTTGGTCTTGTCTCATCG-AGAGCAGGTGTGACGGAT (SEQ ID NO: 14) |
| D12b | ATCCGTCACACCTGCTCT-CGATGAGACAAGACCAACACGGCACAATTGATTTAA-TGGTGTTGGCTCCCGTAT (SEQ ID NO: 23) |
| D17a | ATACGGGAGCCAACACCA-TTTTTATTATCGGTATGATCCTACGAGTTCCTCCCA-AGAGCAGGTGTGACGGAT (SEQ ID NO: 15) |
| D17b | ATCCGTCACACCTGCTCT-TGGGAGGAACTCGTAGGATCATACCGATAATAAAAA-TGGTGTTGGCTCCCGTAT (SEQ ID NO: 24) |
| D18a | ATACGGGAGCCAACACCA-CCGTATATCTTATTATGCACAGCATCACGAAAGTGC-AGAGCAGGTGTGACGGAT (SEQ ID NO: 16) |
| D18b | ATCCGTCACACCTGCTCT-TTTTTATTATCGGTATGATCCTACGAGTTCCTCCCA-TGGTGTTGGCTCCCGTAT (SEQ ID NO: 25) |
| D19a | ATACGGGAGCCAACACCA-TTAACGTTAAGCGGCCTCACTTCTTTTAATCCTTTC-AGAGCAGGTGTGACGGAT (SEQ ID NO: 17) |
| D19b | ATCCGTCACACCTGCTCT-GAAAGGATTAAAAGAAGTGAGGCCGCTTAACGTTAA-TGGTGTTGGCTCCCGTAT (SEQ ID NO: 26) |
| D20a | ATCCGTCACACCTGCTCT-AATATAGAGGTATTGCTCTTGGACAAGGTACAGGGA-TGGTGTTGGCTCCCGTAT (SEQ ID NO: 18) |
| D20b | ATACGGGAGCCAACACCA-TCCCTGTACCTTGTCCAAGAGCAATACCTCTATATT-ACCACAACCGAGGGCATA (SEQ ID NO: 27) |
| M17a | ATACGGGAGCCAACACCA-GCAGTCAAGAAGTTAAGAGAAAAACAATTGTGTATA-AGAGCAGGTGTGACGGAT (SEQ ID NO: 20) |
| M17b | ATCCGTCACACCTGCTCT-TATACACAATTGTTTTCTCTTAACTTCTTGACTGC-TGGTGTTGGCTCCCGTAT (SEQ ID NO: 28) |
| M21a | ATCCGTCACACCTGCTCT-GCGCCACAAGATTGCGAAAGACACCCGGGGGGCT-TGGTGTTGGCTCCCGTAT (SEQ ID NO: 21) |
| M21b | ATACGGGAGCCAACACCA-AGCCCCCCGGGTGTCTTTCCGCAATCTTGTGGCGC-AGAGCAGGTGTGACGGAT (SEQ ID NO: 29) |
| M25a | ATCCGTCACACCTGCTCT-GGCCTTATGTAAAGCGTTGGG-TGGTGTTGGCTCCCGTAT (SEQ ID NO: 22) |
| M25b | ATACGGGAGCCAACACCA-CCCAACGCTTTACATAAGGCC-AGAGCAGGTGTGACGGAT (SEQ ID NO: 30) |

E. coli O157 Lipopolysaccharide (LPS) Aptamers

SEQ ID NO. 31
(E-5F)
ATCCGTCACACCTGCTCTGGTGGAATGGACTAAGCTAGCTAGCGTTTTAA
AAGGTGGTGTTGGCTCCCGTAT

SEQ ID NO. 32
(E-11F)
ATCCGTCACACCTGCTCTGTAAGGGGGGGAATCGCTTTCGTCTTAAGAT
GACATGGTGTTGGCTCCCGTAT

SEQ ID NO. 33
(E-12F)
ATCCGTCACACCTGCTCTGCCGGACCATCCAATATCAGCTGTGGTGTTGG
CTCCCGTAT

SEQ ID NO. 34
(E-16F)
ATCCGTCACACCTGCTCTATCCGTCACGCCTGCTCTATCCGTCACACCTG
CTCTGGTGTTGGCTCCCGTAT

SEQ ID NO. 35
(E-17F)
ATCCGTCACACCTGCTCTATCAAATGTGCAGATATCAAGACGATTTGTAC
AAGATGGTGTTGGCTCCCGTAT

SEQ ID NO. 36
(E-18F)
ATCCGTCACACCTGCTCTGTAGATGGCAAGGCATAAGCGTCCGGAACGAT
AGAATGGTGTTGGCTCCCGTAT

SEQ ID NO. 37
(E-19F)
ATCCGTCACACCTGCTCTGTAGATGGCAAGGCATAAGCGTCCGGAACGAT
AGAATGGTGTTGGCTCCCGTAT

SEQ ID NO. 38
(E-5R)
ATACGGGAGCCAACACCACCTTTTAAAACGCTAGCTAGCTTAGTCCATTC
CACCAGAGCAGGTGTGACGGAT

SEQ ID NO. 39
(E-11R)
ATACGGGAGCCAACACCATGTCATCTTAAGACGAAAGCGATTCCCCCCCC
TTACAGAGCAGGTGTGACGGAT

SEQ ID NO. 40
(E-12R)
ATACGGGAGCCAACACCACAGCTGATATTGGATGGTCCGGCAGAGCAGGT
GTGACGGAT

SEQ ID NO. 41
(E-16R)
ATACGGGAGCCAACACCAGAGCAGGTGTGACGGATAGAGCAGGCGTGACG
GATAGAGCAGGTGTGACGGAT

SEQ ID NO. 42
(E-17R)
ATACGGGAGCCAACACCATCTTGTACAAATCGTCTTGATATCTGCACATT
TGATAGAGCAGGTGTGACGGAT

SEQ ID NO. 43
(E-18R)
ATACGGGAGCCAACACCATTCTATCGTTCCGGACGCTTATGCCTTGCCAT
CTACAGAGCAGGTGTGACGGAT

SEQ ID NO. 44
(E-19R)
ATACGGGAGCCAACACCATTCTATCGTTCCGGACGCTTATGCCTTGCCAT
CTACAGAGCAGGTGTGACGGAT

Listeriolysin (A surface Protein on *Listeria* monocytogenes) Aptamers

SEQ ID NO. 45
(LO-10F)
GTATATCCGTCACACCTGCTCTGCCGGACCATCCAATATCAGCTGTGGTG
TTGGCTCCCGTAT

SEQ ID NO. 46
(LO-11F)
ATCCGTCACACCTGCTCTGGTGGAATGGACTAAGCTAGCTAGCGTTTTAA
AAGGTGGTGTTGGCTCCCGTAT

SEQ ID NO. 47
(LO-13F)
ATCCGTCACACCTGCTCTTAAAGTAGAGGCTGTTCTCCAGACGTCGCAGG
AGGATGGTGTTGGCTCCCGTAT

SEQ ID NO. 48
(LO-15F)
ATCCGTCACACCTGCTCTGTAGATGGCAAGGCATAAGCGTCCGGAACGAT
AGAATGGTGTTGGCTCCCGTAT

SEQ ID NO. 49
(LO-16F)
ATCCGTCACACCTGCTCTGTAGATGGCAAGGCATAAGCGTCCGGAACGAT
AGAATGGTGTTGGCTCCCGTAT

SEQ ID NO. 50
(LO-17F)
ATACGGGAGCCAACACCACAGCTGATATTGGATGGTCCGGCAGAGCAGGT
GTGACGGAT

SEQ ID NO. 51
(LO-19F)
ATCCGTCACACCTGCTCTTGGGCAGGAGCGAGAGACTCTAATGGTAAGCA
AGAATGGTGTTGGCTCCCGTAT

SEQ ID NO. 52
(LO-20F)
ATCCGTCACACCTGCTCTCCAACAAGGCGACCGACCGCATGCAGATAGCC
AGGTTGGTGTTGGCTCCCGTAT

SEQ ID NO. 53
(LO-10R)
ATACGGGAGCCAACACCACAGCTGATATTGGATGGTCCGGCAGAGCAGGT
GTGACGGAT

SEQ ID NO. 54
(LO-11R)
ATACGGGAGCCAACACCACCTTTTAAAACGCTAGCTAGCTTAGTCCATTC
CACCAGAGCAGGTGTGACGGAT

SEQ ID NO. 55
(LO-13R)
ATACGGGAGCCAACACCATCCTCCTGCGACGTCTGGAGAACAGCCTCTAC
TTTAAGAGCAGGTGTGACGGAT

-continued

SEQ ID NO. 56
(LO-15R)
ATACGGGAGCCAACACCATTCTATCGTTCCGGACGCTTATGCCTTGCCAT

CTACAGAGCAGGTGTGACGGAT

SEQ ID NO. 57
(LO-16R)
ATACGGGAGCCAACACCATTCTATCGTTCCGGACGCTTATGCCTTGCCAT

CTACAGAGCAGGTGTGACGGAT

SEQ ID NO. 58
(LO-17R)
ATCCGTCACACCTGCTCTGCCGGACCATCCAATATCAGCTGTGGTGTTGG

CTCCCGTAT

SEQ ID NO. 59
(LO-19R)
ATACGGGAGCCAACACCATTCTTGCTTACCATTAGAGTCTCTCGCTCCTG

CCCAAGAGCAGGTGTGACGGAT

SEQ ID NO. 60
(LO-20R)
ATACGGGAGCCAACACCAACCTGGCTATCTGCATGCGGTCGGTCGCCTTG

TTGGAGAGCAGGTGTGACGGAT

Listeriolysin (Alternate Form of *Listeria* Surface Protein Designated "Pest-Free") Aptamers SEQ ID NO. 61
(LP-3F)
ATCCGTCACACCTGCTCTGTAGATGGCAAGGCATAAGCGTCCGGAACGAT
AGAATGGTGTTGGCTCCCGTAT SEQ ID NO. 62
(LP-11F)
ATCCGTCACACCTGCTCTAACCAAAAGGGTAGGAGACCAAGCTAGCGATT
TGGATGGTGTTGGCTCCCGTAT SEQ ID NO. 63
(LP-13F)
ATCCGTCACACCTGCTCTGCCGGACCATCCAATATCAGCTGTGGTGTTGG
CTCCCGTAT SEQ ID NO. 64
(LP-14F)
ATCCGTCACACCTGCTCTGAAGCCTAACGGAGAAGATGGCCCTACTGCCG
TAGGTGGTGTTGGCTCCCGTAT SEQ ID NO. 65
(LP-15F)
ATCCGTCACACCTGCTCTACTAAACAAGGGCAAACTGTAAACACAGTAGG
GGCGTGGTGTTGGCTCCCGTAT SEQ ID NO. 66
(LP-17F)
ATCCGTCACACCTGCTCTGGTGTTGGCTCCCGTATAGCTTGGCTCCCGTA
TGGTGTTGGCTCCCGTAT SEQ ID NO. 67
(LP-18F)
ATCCGTCACACCTGCTCTGTCGCGATGATGAGCAGCAGCGCAGGAGGGAG
GGGGTGGTGTTGGCTCCCGTAT -continued SEQ ID NO. 68
(LP-20F)
ATCCGTCACACCTGCTCTGATCAGGGAAGACGCCAACACTGGTGTTGGCT
CCCGTAT SEQ ID NO. 69
(LP-3R)
ATACGGGAGCCAACACCATTCTATCGTTCCGGACGCTTATGCCTTGCCAT
CTACAGAGCAGGTGTGACGGAT SEQ ID NO. 70
(LP-11R)
ATACGGGAGCCAACACCATCCAAATCGCTAGCTTGGTCTCCTACCCTTTT
GGTTAGAGCAGGTGTGACGGAT SEQ ID NO. 71
(LP-13R)
ATACGGGAGCCAACACCACAGCTGATATTGGATGGTCCGGCAGAGCAGGT
GTGACGGAT SEQ ID NO. 72
(LP-14R)
ATACGGGAGCCAACACCACCTACGGCAGTAGGGCCATCTTCTCCGTTAGG
CTTCAGAGCAGGTGTGACGGAT SEQ ID NO. 73
(LP-15R)
ATACGGGAGCCAACACCACGCCCCTACTGTGTTTACAGTTTGCCCTTGTT
TAGTAGAGCAGGTGTGACGGAT SEQ ID NO. 74
(LP-17R)
ATACGGGAGCCAACACCATACGGGAGCCAAGCTATACGGGAGCCAACACC
AGAGCAGGTGTGACGGAT SEQ ID NO. 75
(LP-18R)
ATACGGGAGCCAACACCACCCCCTCCCTCCTGCGCTGCTGCTCATCATCG
CGACAGAGCAGGTGTGACGGAT SEQ ID NO. 76
(LP-20R)
ATACGGGAGCCAACACCAGTGTTGGCGTCTTCCCTGATCAGAGCAGGTGT
GACGGAT

*Salmonella typhimurium* Lipopolysaccharide (LPS) Aptamers

SEQ ID NO. 77
(St-7F)
ATCCGTCACACCTGCTCTGTCCAAAGGCTACGCGTTAACGTGGTGTTGGC
TCCCGTAT

SEQ ID NO. 78
(St-10F)
ATCCGTCACACCTGCTCTGGAGCAATATGGTGGAGAAACGTGGTGTTGGC
TCCCGTAT

SEQ ID NO. 79
(St-11F)
ATCCGTCACACCTGCTCTGCCGGACCATCCAATATCAGCTGTGGTGTTGG
CTCCCGTAT

-continued

SEQ ID NO. 80
(St-15F)
ATCCGTCACACCTGCTCTGAACAGGATAGGGATTAGCGAGTCAACTAAGC
AGCATGGTGTTGGCTCCCGTAT

SEQ ID NO. 81
(St-16F)
ATCCGTCACACCTGCTCTGGCGGACAGGAAATAAGAATGAACGCAAAATT
TATCTGGTGTTGGCTCCCGTAT

SEQ ID NO. 82
(St-18F)
ATCCGTCACACCTGCTCTACGCAACGCGACAGGAACATTCATTATAGAAT
GTGTTGGTGTTGGCTCCCGTAT

SEQ ID NO. 83
(St-19F)
ATCCGTCACACCTGCTCTCGGCTGCAATGCGGGAGAGTAGGGGGGAACCA
AACCTGGTGTTGGCTCCCGTAT

SEQ ID NO. 84
(St-20F)
ATCCGTCACACCTGCTCTATGACTGGAACACGGGTATCGATGATTAGATG
TCCTTGGTGTTGGCTCCCGTAT

SEQ ID NO. 85
(St-7R)
ATACGGGAGCCAACACCACGTTAACGCGTAGCCTTTGGACAGAGCAGGTG
TGACGGAT

SEQ ID NO. 86
(St-10R)
ATACGGGAGCCAACACCACGTTTCTCCACCATATTGCTCCAGAGCAGGTG
TGACGGAT

SEQ ID NO. 87
(St-11R)
ATACGGGAGCCAACACCACAGCTGATATTGGATGGTCCGGCAGAGCAGGT
GTGACGGAT

SEQ ID NO. 88
(St-15R)
ATACGGGAGCCAACACCATGCTGCTTAGTTGACTCGCTAATCCCTATCCT
GTTCAGAGCAGGTGTGACGGAT

SEQ ID NO. 89
(St-16R)
ATACGGGAGCCAACACCAGATAAATTTTGCGTTCATTCTTATTTCCTGTC
CGCCAGAGCAGGTGTGACGGAT

SEQ ID NO. 90
(St-18R)
ATACGGGAGCCAACACCAACACATTCTATAATGAATGTTCCTGTCGCGTT
GCGTAGAGCAGGTGTGACGGAT

SEQ ID NO. 91
(St-19R)
ATACGGGAGCCAACACCAGGTTTGGTTCCCCCTACTCTCCCGCATTGCA
GCCGAGAGCAGGTGTGACGGAT

SEQ ID NO. 92
(St-20R)
ATACGGGAGCCAACACCAAGGACATCTAATCATCGATACCCGTGTTCCAG
TCATAGAGCAGGTGTGACGGAT

Core LPS Antigen (Glucosamine, KDO Antigen, and Rough LPS Core) Aptamers

SEQ ID NO. 93
(Glucosamine(G)1F)
ATCCGTCACACCTGCTCTAATTAGGATACGGGGCAACAGAACGAGAGGGG
GGAATGGTGTTGGCTCCCGTAT SEQ ID NO. 94
(G2F)
ATCCGTCACACCTGCTCTCGGACCAGGTCAGACAAGCACATCGGATATCC
GGCTGGTGTTGGCTCCCGTAT SEQ ID NO. 95
(G5F)
ATCCGTCACACCTGCTCTTGAGTCAAAGAGTTTAGGGAGGAGCTAACATA
ACAGTGGTGTTGGCTCCCGTAT SEQ ID NO. 96
(G7F)
ATCCGTCACACCTGCTCTAACAACAATGCATCAGCGGGCTGGGAACGCAT
GCGGTGGTGTTGGCTCCCGTAT SEQ ID NO. 97
(G8F)
ATCCGTCACACCTGCTCTGAACAGGTTATAAGCAGGAGTGATAGTTTCAG
GATCTGGTGTTGGCTCCCGTAT SEQ ID NO. 98
(G9F)
ATCCGTCACACCTGCTCTCGGCGGCTCGCAAACCGAGTGGTCAGCACCCG
GGTTGGTGTTGGCTCCCGTAT SEQ ID NO. 99
(G10F)
ATCCGTCACACCTGCTCTGCGCAAGACGTAATCCACAAGACCGTGAAAAC
ATAGTGGTGTTGGCTCCCGTAT SEQ ID NO. 100
(G1R)
ATACGGGAGCCAACACCATTCCCCCCTCTCGTTCTGTTGCCCCGTATCCT
AATTAGAGCAGGTGTGACGGAT SEQ ID NO. 101
(G2R)
ATACGGGAGCCAACACCAGCCGGATATCCGATGTGCTTGTCTGACCTGGT
CCGAGAGCAGGTGTGACGGAT SEQ ID NO. 102
(G5R)
ATACGGGAGCCAACACCACTGTTATGTTAGCTCCTCCCTAAACTCTTTGA
CTCAAGAGCAGGTGTGACGGAT SEQ ID NO. 103
(G7R)
ATACGGGAGCCAACACCACCGCATGCGTTCCCAGCCCGCTGATGCATTGT
TGTTAGAGCAGGTGTGACGGAT SEQ ID NO. 104
(G8R)
ATACGGGAGCCAACACCAGATCCTGAAACTATCACTCCTGCTTATAACCT
GTTCAGAGCAGGTGTGACGGAT SEQ ID NO. 105
(G9R)
ATACGGGAGCCAACACCAACCCGGGTGCTGACCACTCGGTTTGCGAGCCG
CCGAGAGCAGGTGTGACGGAT

```
                                        SEQ ID NO. 106
(G10R)
ATACGGGAGCCAACACCACTATGTTTTCACGGTCTTGTGGATTACGTCTT

GCGCAGAGCAGGTGTGACGGAT
                                        SEQ ID NO. 107
(KDO (K) Antigen 2F)
ATCCGTCACACCTGCTCTAGGCGTAGTGACTAAGTCGCGCGAAAATCACA GCATTGGTGTTGGCTCCCGTAT
                                        SEQ ID NO. 108
(K5F)
ATCCGTCACACCTGCTCTCAGCGGCAGCTATACAGTGAGAACGGACTAGT GCGTTGGTGTTGGCTCCCGTAT
                                        SEQ ID NO. 109
(K7F)
ATCCGTCACACCTGCTCTGGCAAATAATACTAGCGATGATGGATCTGGAT AGACTGGTGTTGGCTCCCGTAT
                                        SEQ ID NO. 110
(K8F)
ATCCGTCACACCTGCTCTGGGGGTGCGACTTAGGGTAAGTGGGAAAGACG ATGCTGGTGTTGGCTCCCGTAT
                                        SEQ ID NO. 111
(K9F)
ATCCGTCACACCTGCTCTCAAGAGGAGATGAACCAATCTTAGTCCGACAG GCGGTGGTGTTGGCTCCCGTAT
                                        SEQ ID NO. 112
(K10F)
ATCCGTCACACCTGCTCTGGCCCGGAATTGTCATGACGTCACCTACACCT CCTGTGGTGTTGGCTCCCGTAT
                                        SEQ ID NO. 113
(K2R)
ATACGGGAGCCAACACCAATGCTGTGATTTTCGCGCGACTTAGTCACTAC GCCTAGAGCAGGTGTGACGGAT
                                        SEQ ID NO. 114
(K5R)
ATACGGGAGCCAACACCAACGCACTAGTCCGTTCTCACTGTATAGCTGCC GCTGAGAGCAGGTGTGACGGAT
                                        SEQ ID NO. 115
(K7R)
ATACGGGAGCCAACACCAGTCTATCCAGATCCATCATCGCTAGTATTATT TGCCAGAGCAGGTGTGACGGAT
                                        SEQ ID NO. 116
(K8R)
ATACGGGAGCCAACACCAGCATCGTCTTTCCCACTTACCCTAAGTCGCAC CCCCAGAGCAGGTGTGACGGAT
                                        SEQ ID NO. 117
(K9R)
ATACGGGAGCCAACACCACCGCCTGTCGGACTAAGATTGGTTCATCTCCT CTTGAGAGCAGGTGTGACGGAT
                                        SEQ ID NO. 118
(K10R)
ATACGGGAGCCAACACCACAGGAGGTGTAGGTGACGTCATGACAATTCCG GGCCAGAGCAGGTGTGACGGAT
                                        SEQ ID NO. 119
(Whole LPS from E. coli O111:B4 (L)1F)
ATCCGTCACCCCTGCTCTCGTCGCTATGAAGTAACAAAGATAGGAGCAAT CGGGTGGTGTTGGCTCCCGTAT
                                        SEQ ID NO. 120
(L3F)
ATCCGTCACACCTGCTCTAACGAAGACTGAAACCAAAGCAGTGACAGTGC TGAATGGTGTTGGCTCCCGTAT
                                        SEQ ID NO. 121
(L4F)
ATCCGTCACACCTGCTCTCGGTGACAATAGCTCGATCAGCCCAAAGTCGT CAGATGGTGTTGGCTCCCGTAT
                                        SEQ ID NO. 122
(L6F)
ATCCGTCACACCTGCTCTAACGAAATAGACCACAAATCGATACTTTATGT TATTGGTGTTGGCTCCCGTAT (71)
                                        SEQ ID NO. 123
(L7F)
ATCCGTCACACCTGCTCTGTCGAATGCTCTGCCTGGAAGAGTTGTTAGCA GGGATGGTGTTGGCTCCCGTAT
                                        SEQ ID NO. 124
(L8F)
ATCCGTCACACCTGCTCTTAAGCCGAGGGGTAAATCTAGGACAGGGGTCC ATGATGGTGTTGGCTCCCGTAT
                                        SEQ ID NO. 125
(L9F)
ATCCGTCACACCTGCTCTACTGGCCGGCTCAGCATGACTAAGAAGGAAGT TATGTGGTGTTGGCTCCCGTAT
                                        SEQ ID NO. 126
(L10F)
ATCCGTCACACCTGCTCTGGTACGAATCACAGGGGATGCTGGAAGCTTGG CTCTTGGTGTTGGCTCCCGTAT
                                        SEQ ID NO. 127
(L1R)
ATACGGGAGCCAACACCACCCGATTGCTCCTATCTTTGTTACTTCATAGC GACGAGAGCAGGGGTGACGGAT
                                        SEQ ID NO. 128
(L3R)
ATACGGGAGCCAACACCATTCAGCACTGTCACTGCTTTGGTTTCAGTCTT CGTTAGAGCAGGTGTGACGGAT
                                        SEQ ID NO. 129
(L4R)
ATACGGGAGCCAACACCATCTGACGACTTTGGGCTGATCGAGCTATTGTC ACCGAGAGCAGGTGTGACGGAT
                                        SEQ ID NO. 130
(L6R)
ATACGGGAGCCAACACCAATAACATAAAGTATCGATTTGTGGTCTATTTC GTTAGAGCAGGTGTGACGGAT
                                        SEQ ID NO. 131
(L7R)
ATACGGGAGCCAACACCATCCCTGCTAACAACTCTTCCAGGCAGAGCATT CGACAGAGCAGGTGTGACGGAT
                                        SEQ ID NO. 132
(L8R)
ATACGGGAGCCAACACCATCATGGACCCCTGTCCTAGATTTACCCCTCGG

CTTAAGAGCAGGTGTGACGGAT
```

```
                                                SEQ ID NO. 133
(L9R)
ATACGGGAGCCAACACCACATAACTTCCTTCTTAGTCATGCTGAGCCGGC

CAGTAGAGCAGGTGTGACGGAT

SEQ ID NO. 134
(L10R)
ATACGGGAGCCAACACCAAGAGCCAAGCTTCCAGCATCCCCTGTGATTCG

TACCAGAGCAGGTGTGACGGAT

SEQ ID NO. 135
(Rough (Ra or R) Core LPS Antigens R1F)
ATCCGTCACACCTGCTCTCCGCACGTAGGACCACTTTGGTACACGCTCCC

GTAGTGGTGTTGGCTCCCGTAT

SEQ ID NO. 136
(R5F)
ATCCGTCACACCTGCTCTACGGATGAACGAAGATTTTAAAGTCAAGCTAA

TGCATGGTGTTGGCTCCCGTAT

SEQ ID NO. 137
(R6F)
ATCCGTCACACCTGCTCTGTAGTGAAGAGTCCGCAGTCCACGCTGTTCAA

CTCATGGTGTTGGCTCCCGTAT

SEQ ID NO. 138
(R7F)
ATCCGTCACACCTGCTCTACCGGCTGGCACGGTTATGTGTGACGGGCGAA

GATATGGTGTTGGCTCCCGTAT

SEQ ID NO. 139
(R9F)
ATCCGTCACACCTGCTCTGCGTGTGGAGCGCCTAGGTGAGTGGTGTTGGC

TCCCGTAT

SEQ ID NO. 140
(R10F)
ATCCGTCACACCTGCTCTGATGTCCCTTTGAAGAGTTCCATGACGCTGGC

TCCTTGGTGTTGGCTCCCGTAT

SEQ ID NO. 141
(R1R)
ATACGGGAGCCAACACCACTACGGGAGCGTGTACCAAAGTGGTCCTACGT

GCGGAGAGCAGGTGTGACGGAT

SEQ ID NO. 142
(R5R)
ATACGGGAGCCAACACCATGCATTAGCTTGACTTTAAAATCTTCGTTCAT

CCGTAGAGCAGGTGTGACGGAT

SEQ ID NO. 143
(R6R)
ATACGGGAGCCAACACCATGAGTTGAACAGCGTGGACTGCGGACTCTTCA

CTACAGAGCAGGTGTGACGGAT

SEQ ID NO. 144
(R7R)
ATACGGGAGCCAACACCATATCTTCGCCCGTCACACATAACCGTGCCAGC

CGGTAGAGCAGGTGTGACGGAT

SEQ ID NO. 145
(R9R)
ATACGGGAGCCAACACCACTCACCTAGGCGCTCCACACGCAGAGCAGGTG

TGACGGAT

SEQ ID NO. 146
(R10R)
ATACGGGAGCCAACACCAAGGAGCCAGCGTCATGGAACTCTTCAAAGGGA

CATCAGAGCAGGTGTGACGGAT
```

*Enterococcus faecalis* Teichoic Acid (TA) Aptamers

```
                                                SEQ ID NO. 147
(TA5F)
CATTCACCACACCTCTGCTGGCTTGGCTAGCCTTGATGCTAAACGACCCA

TAGTGTGGTGTCGTCCCGTATC

SEQ ID NO. 148
(TA5R)
GATACGGGACGACACCACACTATGGGTCGTTTAGCATCAAGGCTAGCCAA

GCCAGCAGAGGTGTGGTGAATG

SEQ ID NO. 149
(TA6F)
CATTCACCACACCTCTGCTGGAGGAGGAAGTGGTCTGGAGTTACTTGACA

TAGTGTGGTGTCGTCCCGTATC

SEQ ID NO. 150
(TA6R)
GATACGGGACGACACCACACTATGTCAAGTAACTCCAGACCACTTCCTCC

TCCAGCAGAGGTGTGGTGAATG

SEQ ID NO. 151
(TA7F)
CATTCACCACACCTCTGCTGGACGGAAACAATCCCCGGGTACGAGAATCA

GGGTGTGGTGTCGTCCCGTATC

SEQ ID NO. 152
(TA7R)
GATACGGGACGACACCACACCCTGATTCTCGTACCCGGGGATTGTTTCCG

TCCAGCAGAGGTGTGGTGAATG

SEQ ID NO. 153
(TA9F)
CATTCACCACACCTCTGCTGGAAACCTACCATTAATGAGACATGATGCGG

TGGTGTGGTGTCGTCCCGTATC

SEQ ID NO. 154
(TA9R)
GATACGGGACGACACCACACCACCGCATCATGTCTCATTAATGGTAGGTT

TCCAGCAGAGGTGTGGTGAATG
```

Foot-and-Mouth Disease (FMD) O-Serotype Viral Capsid Aptamers

```
                                                SEQ ID NO. 155
(FMD 1F)
ATACGGGAGCCAACACCATTCTATCGTTCCGGACGCTTATGCCTTGCCAT

CTACAGAGCAGGTGTGACGGAT

SEQ ID NO. 156
(FMD 1R)
ATCCGTCACTCCTGCTCTGTAGATGGCAAGGCATAAGCGTCCGGAACGAT

AGAATGGTGTTGGCTCCCGTAT

SEQ ID NO. 157
(FMD 10F)
ATACGGGAGCCAACACCATGAATATCTCTTCTACCTCCTCTCCTCCCTTT

ACTTAGAGCAGGTGTGACGGAT
```

SEQ ID NO. 158
(FMD 10R)
ATCCGTCACTCCTGCTCTAAGTAAAGGGAGGAGAGGAGGTAGAAGAGATA

TTCATGGTGTTGGCTCCCGTAT

SEQ ID NO. 159
(FMD 11F)
ATACGGGAGCCAACACCACGCCGCCCCAGTTCATGGCCTCTATGTCCGGC

AACGAGAGCAGGTGTGACGGAT

SEQ ID NO. 160
(FMD 11R)
ATCCGTCACTCCTGCTCTCGTTGCCGGACATAGAGGCCATGAACTGGGGC

GGCGTGGTGTTGGCTCCCGTAT

SEQ ID NO. 161
(FMD 12F)
ATACGGGAGCCAACACCATCTAGATCTGAAGAATAAAACAAAGACAAAGA

TGCTAGAGCAGGTGTGACGGAT

SEQ ID NO. 162
(FMD 12R)
ATCCGTCACTCCTGCTCTAGCATCTTTGTCTTTGTTTTATTCAGATCTAG

ATGGTGTTGGCTCCCGTAT

SEQ ID NO. 163
(FMD 13F)
ATACGGGAGCCAACACCACCTTTTAAAACGCTAGCTAGCTTAGTCCATTC

CACCAGAGCAGGTGTGACGGAT

SEQ ID NO. 164
(FMD 13R)
ATCCGTCACTCCTGCTCTGGTGGAATGGACTAAGCTAGCTAGCGTTTTAA

AAGGTGGTGTTGGCTCCCGTAT

*E. coli* Outer Membrane Proteins (OMPs)

SEQ ID NO. 165
(EcO-1F)
ATCCGTCACACCTGCTCTCGATGTCTGGGCCCTAATATTGGTTTGCTTGT

ACCATGGTGTTGGCTCCCGTAT

SEQ ID NO. 166
(EcO-1R)
ATACGGGAGCCAACACCATGGTACAAGCAAACCAATATTAGGGCCCAGAC

ATCG AGAGCAGGTGTGACGGAT

SEQ ID NO. 167
(EcO-2F)
ATACGGGAGCCAACACCATGATACCCTAAGGTAGGGGAGGCCTAAGCGCC

ACGT AGAGCAGGTGTGACGGAT

SEQ ID NO. 168
(EcO-2R)
ATCCGTCACACCTGCTCTACGTGGCGCTTAGGCCTCCCCTACCTTAGGGT

ATCATGGTGTTGGCTCCCGTAT

SEQ ID NO. 169
(EcO-3F)
ATACGGGAGCCAACACCACGCATCCCCCGCCGGGCCCGCGCCCCGCTCGC

AGACAGAGCAGGTGTGACGGAT

SEQ ID NO. 170
(EcO-3R)
ATCCGTCACACCTGCTCTGTCTGCGAGCGGGGCGCGGGCCCGGCGGGGGA

TGCGTGGTGTTGGCTCCCGTAT

SEQ ID NO. 171
(EcO-4F (73))
ATCCGTCACACCTGCTCTACGGCGCTCCCAACAGGCCTCTCCTTACGGCA

TATTATGGTGTTGGCTCCCGTAT

SEQ ID NO. 172
(EcO-4R (73))
ATACGGGAGCCAACACCATAATATGCCGTAAGGAGAGGCCTGTTGGGAGC

GCCGT AGAGCAGGTGTGACGGAT

SEQ ID NO. 173
(EcO-5F)
ATACGGGAGCCAACACCAGGAAAAAAAGAGCCTGTGAAGATTGTAATATC

AGTT AGAGCAGGTGTGACGGAT

SEQ ID NO. 174
(EcO-5R)
ATCCGTCACACCTGCTCTAACTGATATTACAATCTTCACAGGCTCTTTTT

TTCCTGGTGTTGGCTCCCGTAT

SEQ ID NO. 175
(EcO-7Fa)
ATCCGTCACACCTGCTCTCGGAGGTAGACTAGGATTGCGGCGGGGGGTCA

GGTATGGTGTTGGCTCCCGTAT

SEQ ID NO. 176
(EcO-7Fb)
ATACGGGAGCCAACACCACAAAAGCCTTACCTAACTGCCAACAATGAATA

GCAAGAGCAGGTGTGACGGAT

SEQ ID NO. 177
(EcO-7Ra)
ATCCGTCACACCTGCTCTTGCTATTCATTGTTGGCAGTTAGGTAAGGCTT

TTGTTGGTGTTGGCTCCCGTAT

SEQ ID NO. 178
(EcO-7Rb)
ATACGGGAGCCAACACCATACCTGACCCCCCGCCGCAATCCTAGTCTACC

TCCGAGAGCAGGTGTGACGGAT

SEQ ID NO. 179
(EcO-8F)
ATACGGGAGCCAACACCACGACTAACACGACCGTTGGGGGGGCTCGCGC

GGGC AGAGCAGGTGTGACGGAT

SEQ ID NO. 180
(EcO-8R)
ATCCGTCACACCTGCTCTGCCCGCGCGAGCCCCCCCAACGGTCGTGTTA

GTCGTGGTGTTGGCTCCCGTAT

SEQ ID NO. 181
(EcO-9F)
ATACGGGAGCCAACACCAGTCCCCGCCCAGCCGTGAGCCGTACCCCCGCA

CACCAGAGCAGGTGTGACGGAT

SEQ ID NO. 182
(EcO-9R)
ATCCGTCACACCTGCTCTGGTGTGCGGGGGTACGGCTCACGGCTGGGCGG

GGACTGGTGTTGGCTCCCGTAT

-continued

SEQ ID NO. 183
(EcO-10F)
ATCCGTCACACCTGCTCTCAAGGTTGGGCCTGCAAGAGCAAAAACGGGGCGGGA TGGTGTTGGCTCCCGTAT

SEQ ID NO. 184
(EcO-10R)
ATACGGGAGCCAACACCATCCCGCCCCGTTTTTGCTCTTGCAGGCCCAACCTTGAGAGCAGGTGTGACGGAT

SEQ ID NO. 185
(EcO-11F)
ATCCGTCACACCTGCTCTACTTGGCTTGCGACTATTATTCACAGGGCCAAAGACTGGTGTTGGCTCCCGTAT

SEQ ID NO. 186
(EcO-11R)
ATACGGGAGCCAACACCAGTCTTTGGCCCTGTGAATAATAGTCGCAAGCCAAGTAGAGCAGGTGTGACGGAT

SEQ ID NO. 187
(EcO-12F (69))
ATACGGGAGCCAACACCATAGTGTTGGACCAATACGGTAACGTGTCCTTGGAGAGCAGGTGTGACGGAT

SEQ ID NO. 188
(EcO-12R (69))
ATCCGTCACACCTGCTCTCCAAGGACACGTTACCGTATTGGTCCAACACTATGGTGTTGGCTCCCGTAT

SEQ ID NO. 189
(EcO-17F)
ATCCGTCACACCTGCTCTTGGAATGTCGGTGTTTTTCCAATTCCTTGGGTCGTGTGGTGTTGGCTCCCGTAT

SEQ ID NO. 190
(EcO-17R)
ATACGGGAGCCAACACCACACGACCCAAGGAATTGGAAAAACACCGACATTCCA AGAGCAGGTGTGACGGAT

SEQ ID NO. 191
(EcO-18F)
ATCCGTCACACCTGCTCTGCGACGGCGACGCGGTCCGGGCGGGGGTGGAGGACG TGGTGTTGGCTCCCGTAT

SEQ ID NO. 192
(EcO-18R)
ATACGGGAGCCAACACCACGTCCTCCACCCCCGCCCGGACCGCGTCGCCGTCGCAGAGCAGGTGTGACGGAT

SEQ ID NO. 193
(EcO-19Fa)
ATACGGGAGCCAACACCAGAGGGTTCTAGGGTCACTTCCATGAGAATGGCTCACAGAGCAGGTGTGACGGAT

SEQ ID NO. 194
(EcO-19Fb)
ATCCGTCACACCTGCTCTGGCCTGGGGACGCGAGGGAGGCGGGGGGAGTCGTGG TGGTGTTGGCTCCCGTAT

SEQ ID NO. 195
(EcO-19Ra)
ATACGGGAGCCAACACCACCACGACTCCCCCCGCCTCCCTCGCGTCCCAGGCCAGAGCAGGTGTGACGGAT

SEQ ID NO. 196
(EcO-19Rb)
ATCCGTCACACCTGCTCT GTGAGCCATTCTCATGGAAGTGACCCTAGAACCCTCTGGTGTTGGCTCCCGTAT

SEQ ID NO. 197
(EcO-20F)
ATCCGTCACACCTGCTCTCACAGGGCCTCTTACTATACAGTTCTCCAGCGCTGCTGGTGTTGGCTCCCGTAT

SEQ ID NO. 198
(EcO-20R)
ATACGGGAGCCAACACCAGCAGCGCTGGAGAACTGTATAGTAAGAGGCCCTGTG AGAGCAGGTGTGACGGAT

SEQ ID NO. 199
(EcO-21F)
ATCCGTCACACCTGCTCTGCACGGGCTCAGTTTGGCTTTGTATCCTAAGAGAGATGGTGTTGGCTCCCGTAT

SEQ ID NO. 200
(EcO-21R)
ATACGGGAGCCAACACCATCTCTCTTAGGATACAAAGCCAAACTGAGCCCGTGCAGAGCAGGTGTGACGGAT

SEQ ID NO. 201
(EcO-22F)
ATACGGGAGCCAACACCAGGGGTGGCGAACATGGTATAACTTGATAAGTGTGAAGAGCAGGTGTGACGGAT

SEQ ID NO. 202
(EcO-22R)
ATCCGTCACACCTGCTCTTCACACTTATCAAGTTATACCATGTTCGCCACCCCCTGGTGTTGGCTCCCGTAT

SEQ ID NO. 203
(EcO-23F)
ATACGGGAGCCAACACCACTCCGACACCGGCCGCCGGCACCACCCACTCCCCCTAGAGCAGGTGTGACGGAT

SEQ ID NO. 204
(EcO-23R)
ATCCGTCACACCTGCTCTAGGGGGAGTGGGTGGTGCCGGCGGCCGGTGTCGGAGTGGTGTTGGCTCCCGTAT

SEQ ID NO. 205
(EcO-24F)
ATACGGGAGCCAACACCATCCGGCGCGCCCTCCTCCCCCACTGCTCCCCGCCCGAGAGCAGGTGTGACGGAT

SEQ ID NO. 206
(EcO-24R)
ATCCGTCACACCTGCTCTCGGGCGGGAGCAGTGGGGGAGGAGGGCGCGCCGGA TGGTGTTGGCTCCCGTAT

SEQ ID NO. 207
(EcO-25F)
ATACGGGAGCCAACACCATACGCAGAGGTCCCCTACCCAGGCCAGCCGGATGCC AGAGCAGGTGTGACGGAT

SEQ ID NO. 208
(EcO-25R)
ATCCGTCACACCTGCTCTGGCATCCGGCTGGCCTGGGTAGGGGACCTCTGCGTATGGTGTTGGCTCCCGTAT

Shiga Toxins (Shiga-Like Toxin Type 1; Stx-1)

```
(SH-2F)                                             SEQ ID NO. 209
ATCCGTCACACCTGCTCTGGAGACATTAAAAACCGGAGTTTATTTATACC
TTTCTGGTGTTGGCTCCCGTAT (SH-2R)                                             SEQ ID NO. 210
ATACGGGAGCCAACACCAGAAAGGTATAAATAAACTCCGGTTTTTAATGT
CTCCAGAGCAGGTGTGACGGAT (SH-3F(59))                                         SEQ ID NO. 211
ATACGGGAGCCAACACCACTAACTTGTTGCTGATCTTATCCAGAGCAGGT
GTGACGGAT (SH-3R(59))                                         SEQ ID NO. 212
ATCCGTCACACCTGCTCTGGATAAGATCAGCAACAAGTTAGTGGTGTTGG
CTCCCGTAT (SH-4F(58))                                         SEQ ID NO. 213
ATCCGTCACACCTGCTCTGCATGGAGAGTTTTTTGGTCAGTGGTGTTGGC
TCCCGTAT (SH-4R(58))                                         SEQ ID NO. 214
ATACGGGAGCCAACACCACTGACCAAAAAACTCTCCATGCAGAGCAGGTG
TGACGGAT (SH-6F(58))                                         SEQ ID NO. 215
ATACGGGAGCCAACACCACGTTAACGCGTAGCCTTTGGACAGAGCAGGTG
TGACGGAT (SH-6R(58))                                         SEQ ID NO. 216
ATCCGTCACACCTGCTCTGTCCAAAGGCTACGCGTTAACGTGGTGTTGGC
TCCCGTAT (SH-8/21/23/24/25F(59))                             SEQ ID NO. 217
ATCCGTCACACCTGCTCTGCCGGACCATCCAATATCAGCTGTGGTGTTGG
CTCCCGTAT (SH-8/21/23/24/25 Rev(59))                          SEQ ID NO. 218
ATACGGGAGCCAACACCACAGCTGATATTGGATGGTCCGGCAGAGCAGGT
GTGACGGAT (SH-9F)                                             SEQ ID NO. 219
ATCCGTCACACCTGCTCTCGTCCGTCATTAAGTTCGGAGGCTGGCGGGTT
GCGTTGGTGTTGGCTCCCGTAT (SH-9R)                                             SEQ ID NO. 220
ATACGGGAGCCAACACCAACGCAACCCGCCAGCCTCCGAACTTAATGACG
GACGAGAGCAGGTGTGACGGAT (SH-10F)                                            SEQ ID NO. 221
ATACGGGAGCCAACACCATTCTATCGTTCCGGACGCTTATGCCTTGCCAT
CTACAGAGCAGGTGTGACGGAT (SH-10R)                                            SEQ ID NO. 222
ATCCGTCACACCTGCTCTGTAGATGGCAAGGCATAAGCGTCCGGAACGAT
AGAATGGTGTTGGCTCCCGTAT (SH-11F)                                            SEQ ID NO. 223
TCCGTCACACCTGCTCTAACTCTTACTACTTTGTTGCTATCACATTCAAC
TGTTGGTGTTGGCTCCCGTAT (SH-11R)                                            SEQ ID NO. 224
ATACGGGAGCCAACACCAACAGTTGAATGTGATAGCAACAAAGTAGTAAG
AGTTAGAGCAGGTGTGACGGAT (SH-12 F(58))                                       SEQ ID NO. 225
ATCCGTCACACCTGCTCTGGCCTTTCACCAAGCGTCCTTGTGGTGTTGGC
TCCCGTAT (SH-12R(58))                                        SEQ ID NO. 226
ATACGGGAGCCAACACCACAAGGACGCTTGGTGAAAGGCCAGAGCAGGTG
TGACGGAT (SH-16F(58))                                        SEQ ID NO. 227
ATCCGTCACACCTGCTCTGGCACCGAGCACGGGAACCCAGTGGTGTTGGC
TCCCGTAT (SH-16R(58))                                        SEQ ID NO. 228
ATACGGGAGCCAACACCACTGGGTTCCCGTGCTCGGTGCCAGAGCAGGTG
TGACGGAT (SH-17F(69))                                        SEQ ID NO. 229
ATACGGGAGCCAACACCATAGTGTTGGGCCAATACGGTAACGTGTCCTTG
GAGAGCAGGTGTGACGGAT (SH-17R(69))                                        SEQ ID NO. 230
ATCCGTCACACCTGCTCTCCAAGGACACGTTACCGTATTGGCCCAACACT
ATGGTGTTGGCTCCCGTAT (SH-18F)                                            SEQ ID NO. 231
ATCCGTCACACCTGCTCTACCCGATGCCGCCCCGGGATTGTTGTATGACC
ATCTTGGTGTTGGCTCCCGTAT (SH-18R)                                            SEQ ID NO. 232
ATACGGGAGCCAACACCAAGATGGTCATACAACAATCCCGGGGCGGCATC
GGGTAGAGCAGGTGTGACGGAT (SH-19F)                                            SEQ ID NO. 233
ATACGGGAGCCAACACCACCCCATGAGTACACGTGAACGGACACAGCCTC
CGGCAGAGCAGGTGTGACGGAT (SH-19R)                                            SEQ ID NO. 234
ATCCGTCACACCTGCTCTGCCGGAGGCTGTGTCCGTTCACGTGTACTCAT
GGGGTGGTGTTGGCTCCCGTAT
```

```
                                             SEQ ID NO. 235
(SH-20F)
ATCCGTCACACCTGCTCTTAACCATTCATTTCTTTTGTGGTATGACCGTT

CGCCTGGTGTTGGCTCCCGTAT

SEQ ID NO. 236
(SH-20R)
ATACGGGAGCCAACACCAGGCGAACGGTCATACCACAAAAGAAATGAATG

GTTAAGAGCAGGTGTGACGGAT

SEQ ID NO. 237
(SH-22F(58))
ATCCGTCACACCTGCTCTGGGGCTCTTTTCGTTAACCAGGTGGTGTTGGC

TCCCGTAT

SEQ ID NO. 238
(SH-22R(58))
ATACGGGAGCCAACACCACCTGGTTAACGAAAAGAGCCCCAGAGCAGGTG

TGACGGAT
```

*S. typhimurium* (*S. enterica* serovar Typhimurium Type 13311) OMPs

```
                                             SEQ ID NO. 239
(StO-2F)
ATACGGGAGCCAACACCAGATAAATTTTGCGTTCATTCTTATTTCCTGTC

CGCCAGAGCAGGTGTGACGGAT

SEQ ID NO. 240
(StO-2R)
ATCCGTCACACCTGCTCTGGCGGACAGGAAATAAGAATGAACGCAAAATT

TATCTGGTGTTGGCTCCCGTAT

SEQ ID NO. 241
(StO-4F)
ATACGGGAGCCAACACCAGATAAATTTTGGTTCATTCTTATTTCCTGTCC

GCCAGAGCAGGTGTGACGGAT (71)

SEQ ID NO. 242
(StO-4R)
ATCCGTCACACCTGCTCTGGCGGACAGGAAATAAGAATGAACCAAAATTT

ATCTGGTGTTGGCTCCCGTAT (71)

SEQ ID NO. 243
(StO-5F)
ATACGGGAGCCAACACCACGGGGCTACCAGCACCGTCACCCCTCATTCTG

CCACAGAGCAGGTGTGACGGAT

SEQ ID NO. 244
(StO-5R)
ATCCGTCACACCTGCTCTGTGGCAGAATGAGGGGTGACGGTGCTGGTAGC

CCCGTGGTGTTGGCTCCCGTAT

SEQ ID NO. 245
(StO-6F)
ATACGGGAGCCAACACCAAAAGATGGAAAACACTGGAAGGAAATGCGGT

CAGAGCAGGTGTGACGGAT (69)

SEQ ID NO. 246
(StO-6R)
ATCCGTCACACCTGCTCTGACCGCATTTTCCTTCCAGTGTTTTCCATCTT

TTGGTGTTGGCTCCCGTAT (69)

SEQ ID NO. 247
(StO-7F)
ATACGGGAGCCAACACCACCGGGCCGATGGGCACCAGGAACTCTCGGACG

AGTGAGAGCAGGTGTGACGGAT

SEQ ID NO. 248
(StO-7R)
ATCCGTCACACCTGCTCTCACTCGTCCGAGAGTTCCTGGTGCCCATCGGC

CCGGTGGTGTTGGCTCCCGTAT

SEQ ID NO. 249
(StO-8F)
ATACGGGAGCCAACACCACAGCTGATATTGGATGGTCCGGCAGAGCAGGT

GTGACGGAT(59)

SEQ ID NO. 250
(StO-8R)
ATCCGTCACACCTGCTCTGCCGGACCATCCAATATCAGCTGTGGTGTTGG

CTCCCGTAT(59)

SEQ ID NO. 251
(StO-9F)
ATACGGGAGCCAACACCAGTCGAAAGGCGGCCGTCCAGTCGAGTGATTTG

ACCTAGAGCAGGTGTGACGGAT

SEQ ID NO. 252
(StO-9R)
ATCCGTCACACCTGCTCTAGGTCAAATCACTCGACTGGACGGCCGCCTTT

CGACTGGTGTTGGCTCCCGTAT

SEQ ID NO. 253
(StO-10F)
ATACGGGAGCCAACACCACGGGGCGTGCCGTCAAAAGACCGAGATGTGGC

TGCGAGAGCAGGTGTGACGGAT

SEQ ID NO. 254
(StO-10R)
ATCCGTCACACCTGCTCTCGCAGCCACATCTCGGTCTTTTGACGGCACGC

CCCGTGGTGTTGGCTCCCGTAT

SEQ ID NO. 255
(StO-11/13F)
ATACGGGAGCCAACACCACTAACTTGTTGCTGATCTTATCCAGAGCAGGT

GTGACGGAT(59)

SEQ ID NO. 256
(StO-11/13R)
ATCCGTCACACCTGCTCTGGATAAGATCAGCAACAAGTTAGTGGTGTTGG

CTCCCGTAT(59)

SEQ ID NO. 257
(StO-12F)
ATACGGGAGCCAACACCATTTAGCGTAGGGCTCGCTTATCATTTCTCATT

CCCTAGAGCAGGTGTGACGGAT

SEQ ID NO. 258
(StO-12R)
ATCCGTCACACCTGCTCTAGGGAATGAGAAATGATAAGCGAGCCCTACGC

TAAATGGTGTTGGCTCCCGTAT

SEQ ID NO. 259
(StO-14F)
ATACGGGAGCCAACACCACCGCAACCCAAATCTCTACACGGATTATCGTC

GAGCAGAGCAGGTGTGACGGAT
```

SEQ ID NO. 260
(StO-14R)
ATCCGTCACACCTGCTCTGCTCGACGATAATCCGTGTAGAGATTTGGGTTGCGGTGGTGTTGGCTCCCGTAT

SEQ ID NO. 261
(StO-16F)
ATACGGGAGCCAACACCAACACATTCTATAATGAATGTTCCTGTCGCGTTGCGTAGAGCAGGTGTGACGGAT

SEQ ID NO. 262
(StO-16R)
ATCCGTCACACCTGCTCTACGCAACGCGACAGGAACATTCATTATAGAATGTGTTGGTGTTGGCTCCCGTAT

SEQ ID NO. 263
(StO-17F)
ATACGGGAGCCAACACCAGCCTACCCCCCCTGTACGAGGGCCGCAACCACGTAGAGAGCAGGTGTGACGGAT

SEQ ID NO. 264
(StO-17R)
ATCCGTCACACCTGCTCTCTACGTGGTTGCGGCCCTCGTACAGGGGGGTAGGCTGGTGTTGGCTCCCGTAT

SEQ ID NO. 265
(StO-18F)
ATACGGGAGCCAACACCACATCTAGCACGAGACCCTATCCCAGAGCAGGTGTGACGGAT(59)

SEQ ID NO. 266
(StO-18R)
ATCCGTCACACCTGCTCTGGGATAGGGTCTCGTGCTAGATGTGGTGTTGGCTCCCGTAT(59)

SEQ ID NO. 267
(StO-19F)
ATACGGGAGCCAACACCAACAGCGACTCGAGTCTGACGACTCGCGGGCAAATGAGAGCAGGTGTGACGGAT

SEQ ID NO. 268
(StO-19R)
ATCCGTCACACCTGCTCTCATTTGCCCCGCGAGTCGTCAGACTCGAGTCGCTGTTGGTGTTGGCTCCCGTAT

SEQ ID NO. 269
(StO-20/24F)
ATACGGGAGCCAACACCATAGTGTTGGGCCAATACGGTAACGTGTCCTTGGAGAGCAGGTGTGACGGAT(69)

SEQ ID NO. 270
(StO-20/24R)
ATCCGTCACACCTGCTCTCCAAGGACACGTTACCGTATTGGCCCAACACTATGGTGTTGGCTCCCGTAT(69)

SEQ ID NO. 271
(StO-21F)
ATACGGGAGCCAACACCACTAAGGAGAGGTCGCGACAGACTCTTCTGGTCAAGGAGAGCAGGTGTGACGGAT

SEQ ID NO. 272
(StO-21R)
ATCCGTCACACCTGCTCTCCTTGACCAGAAGAGTCTGTCGCGACCTCTCCTTAGTGGTGTTGGCTCCCGTATG

SEQ ID NO. 273
(StO-22F)
ATACGGGAGCCAACACCAACTTCGACTCAAAGAAGTCCACGTGAGACTGGTGGAAGAGCAGGTGTGACGGAT

SEQ ID NO. 274
(StO-22R)
ATCCGTCACACCTGCTCTTCCACCAGTCTCACGTGGACTTCTTTGAGTCGAAGTTGGTGTTGGCTCCCGTAT

SEQ ID NO. 275
(StO-23F)
ATACGGGAGCCAACACCACCCGGGGAGACCCGCACGGGCGCACAATCCTTGTCGAGAGCAGGTGTGACGGAT

SEQ ID NO. 276
(StO-23R)
ATCCGTCACACCTGCTCTCGACAAGGATTGTGCGCCCGTGCGGGTCTCCCCGGGTGGTGTTGGCTCCCGTAT

SEQ ID NO. 277
(StO-25F)
ATACGGGAGCCAACACCAGCTGGACCAAACTACGCCCATTGTGGGGTCCCCGGAGAGCAGGTGTGACGGAT

SEQ ID NO. 278
(StO-25R)
ATCCGTCACACCTGCTCTCCGGGGACCCCCACAATGGGCGTAGTTTGGTCCAGCTGGTGTTGGCTCCCGTAT

Gram Negative Quorum Sensing Molecules (N-Acylhomoserine Lactones; AHLs)

SEQ ID NO. 279
(Dec AHL 1F)
ATACGGGAGCCAACACCATCCTAACTGGTCTAATTTTTGCTGTTACCGATCCCGAGAGCAGGTGTGACGGAT

SEQ ID NO. 280
(Dec AHL 1R)
ATCCGTCACTCCTGCTCTCGGGATCGGTAACAGCAAAAATTAGACCAGTTAGGATGGTGTTGGCTCCCGTAT

SEQ ID NO. 281
(Dec AHL 13F)
ATACGGGAGCCAACACCAGCCTGACGAAAAAATTTTATCACTAAGTGATACGCAAGAGCAGGTGTGACGGAT

SEQ ID NO. 282
(Dec AHL 13R)
ATCCGTCACACCTGCTCTTGCGTATCACTTAGTGATAAAATTTTTTCGTCAGGCTGGTGTTGGCTCCCGTAT

SEQ ID NO. 283
(Dec AHL 14F)
ATACGGGAGCCAACACCAGACCTACTTCAGAAACGGAAATGTTCTTAGCCGTCAGAGCAGGTGTGACGGAT

SEQ ID NO. 284
(Dec AHL 14R)
ATCCGTCACACCTGCTCTGACGGCTAAGAACATTTCCGTTTCTGAAGTAGGTCTGGTGTTGGCTCCCGTAT

SEQ ID NO. 285
(Dec AHL 15F)
ATACGGGAGCCAACACCAGGCCAACGAAACTCCTACTACATATAATGCTT

ATGCAGAGCAGGTGTGACGGAT

SEQ ID NO. 286
(Dec AHL 15R)
ATCCGTCACACCTGCTCTGCATAAGCATTATATGTAGTAGGAGTTTCGTT

GGCCTGGTGTTGGCTCCCGTAT

SEQ ID NO. 287
(Dec AHL 17F)
ATACGGGAGCCAACACCATCCTAACTGGTCTAATTTTTGCTGTTACCGAT

CCCGAGAGCAGGTGTGACGGAT

SEQ ID NO. 288
(Dec AHL 17R)
ATCCGTCACACCTGCTCTCGGGATCGGTAACAGCAAAAATTAGACCAGTT

AGGATGGTGTTGGCTCCCGTAT

Shiga Toxins (Shiga-Like Toxin Type 2; Stx-2)

SEQ ID NO. 289
(S2-1 For)
ATACGGGAGCCAACACCAGGCGACCAAGTTTGAATCACCACAATCGTGAC

GGTGAGAGCAGGTGTGACGGAT

SEQ ID NO. 290
(S2-1 Rev)
ATCCGTCACACCTGCTCTCACCGTCACGATTGTGGTGATTCAAACTTGGT
CGCCTGGTGTTGGCTCCCGTAT

SEQ ID NO. 291
(S2-2 For)
ATACGGGAGCCAACACCACCATCACATCTTGGCCCGGTACCCTGGATACT
AGCCAGAGCAGGTGTGACGGAT

SEQ ID NO. 292
(S2-2 Rev)
ATCCGTCACACCTGCTCTGGCTAGTATCCAGGGTACCGGGCCAAGATGTG
ATGGTGGTGTTGGCTCCCGTAT

SEQ ID NO. 293
(S2-3 For)
ATACGGGAGCCAACACCAGCACTAGCTCGGGTAACGGGGACATTAGAGTT
TGCCAGAGCAGGTGTGACGGAT

SEQ ID NO. 294
(S2-3 Rev)
ATCCGTCACACCTGCTCTGGCAAACTCTAATGTCCCCGTTACCCGAGCTA
GTGCTGGTGTTGGCTCCCGTAT

SEQ ID NO. 295
(S2-4 For)
ATCCGTCACACCTGCTCTAGTTGGAAGTCTTGTAGATCTGGGCGCGGTGG
GCTTTGGTGTTGGCTCCCGTAT

SEQ ID NO. 296
(S2-4 Rev)
ATACGGGAGCCAACACCAAAGCCCACCGCGCCCAGATCTACAAGACTTCC
AACTAGAGCAGGTGTGACGGAT

-continued

SEQ ID NO. 297
(S2-5 For)
ATACGGGAGCCAACACCATCTTTGTCACTCTGGATTAGGTTAATCCACTG
AAACAGAGCAGGTGTGACGGAT

SEQ ID NO. 298
(S2-5 Rev)
ATCCGTCACACCTGCTCTGTTTCAGTGGATTAACCTAATCCAGAGTGACA
AAGATGGTGTTGGCTCCCGTAT

SEQ ID NO. 299
(S2-7 For)
ATCCGTCACACCTGCTCTCGCTCGAGGGGGACAATTGCTAGAATCCCGGG
TTCGTGGTGTTGGCTCCCGTAT

SEQ ID NO. 300
(S2-7 Rev)
ATACGGGAGCCAACACCACGAACCCGGGATTCTAGCAATTGTCCCCCTCG
AGCGAGAGCAGGTGTGACGGAT

SEQ ID NO. 301
(S2-8 For)
ATACGGGAGCCAACACCAATGATTAATAGAACCCCCTATGACCTGGCCGC
TGGGAGAGCAGGTGTGACGGAT

SEQ ID NO. 302
(S2-8 Rev)
ATCCGTCACACCTGCTCTCCCAGCGGCCAGGTCATAGGGGGTTCTATTAA
TCATTGGTGTTGGCTCCCGTAT

SEQ ID NO. 303
(S2-9 For)
ATCCGTCACACCTGCTCTTGTTAAACCCGACAACATGGACATGCTATCCG
ACCATGGTGTTGGCTCCCGTAT

SEQ ID NO. 304
(S2-9 Rev)
ATACGGGAGCCAACACCATGGTCGGATAGCATGTCCATGTTGTCGGGTTT
AACAAGAGCAGGTGTGACGGAT

SEQ ID NO. 305
(S2-10 For)
ATACGGGAGCCAACACCAGGGGAATCTTGCTTGCGTAGCGACGCATAATG
ACGTAGAGCAGGTGTGACGGAT

SEQ ID NO. 306
(S2-10 Rev)
ATCCGTCACACCTGCTCTACGTCATTATGCGTCGCTACGCAAGCAAGATT
CCCCTGGTGTTGGCTCCCGTAT

SEQ ID NO. 307
(S2-12 For)
ATCCGTCACACCTGCTCTCCGGTACGTCAGGGGAACGCACATTTGTCCAC
TTCATGGTGTTGGCTCCCGTAT

SEQ ID NO. 308
(S2-12 Rev)
ATACGGGAGCCAACACCATGAAGTGGACAAATGTGCGTTCCCCTGACGTA
CCGGAGAGCAGGTGTGACGGAT

SEQ ID NO. 309
(S2-13 For)
ATCCGTCACACCTGCTCTCCTCGACTCGATATCACTTAGTCTAACACTAA
ATGGTGGTGTTGGCTCCCGTAT

SEQ ID NO. 310
(S2-13 Rev)
ATACGGGAGCCAACACCACCATTTAGTGTTAGACTAAGTGATATCGAGTC
GAGGAGAGCAGGTGTGACGGAT

SEQ ID NO. 311
(S2-14 For)
ATACGGGAGCCAACACCACTTCCACTTTTTCGCCTAATTGCCTGTTGCAT
GGTAAGAGCAGGTGTGACGGAT

SEQ ID NO. 312
(S2-14 Rev)
ATCCGTCACACCTGCTCTCAACTATATTCGCCTTAAAGACTTTAGGACAT
CGCCTGGTGTTGGCTCCCGTAT

SEQ ID NO. 313
(S2-15 For)
ATACGGGAGCCAACACCAGGCGATGTCCTAAAGTCTTTAAGGCGAATATA
GTTGAGAGCAGGTGTGACGGAT

SEQ ID NO. 314
(S2-15 Rev)
ATCCGTCACACCTGCTCTTACCATGCAACAGGCAATTAGGCGAAAAAGTG
GAAGTGGTGTTGGCTCCCGTAT

SEQ ID NO. 315
(S2-16 For)
ATACGGGAGCCAACACCACCCCCCCCTCCGTGGGCCGCTCCCCTCGGCCG
GGCCAGAGCAGGTGTGACGGAT

SEQ ID NO. 316
(S2-16 Rev)
ATCCGTCACACCTGCTCTGGCCCGGCCGAGGGGAGCGGCCCACGGAGGGG
GGGGTGGTGTTGGCTCCCGTAT

SEQ ID NO. 317
(S2-17 For)
ATCCGTCACACCTGCTCTCCTTCGCTCGTCTTGTATTGTCGTTGCTTCAC
GGGATGGTGTTGGCTCCCGTAT

SEQ ID NO. 318
(S2-17 Rev)
ATACGGGAGCCAACACCATCCCGTGAAGCAACGACAATACAAGACGAGCG
AAGGAGAGCAGGTGTGACGGAT

SEQ ID NO. 319
(S2-18 For)
ATCCGTCACACCTGCTCTGGCCCCAAGCGCTCTGTATCTGTTGAAGAAGT
CGCGTGGTGTTGGCTCCCGTAT

SEQ ID NO. 320
(S2-18 Rev)
ATACGGGAGCCAACACCACGCGACTTCTTCAACAGATACAGAGCGCTTGG
GGCCAGAGCAGGTGTGACGGAT

SEQ ID NO. 321
(S2-19 For)
ATACGGGAGCCAACACCAGGAAATGGTACCTAAGAAATGAGAACTTTGAC
GCACAGAGCAGGTGTGACGGAT

SEQ ID NO. 322
(S2-19 Rev)
ATCCGTCACACCTGCTCTGTGCGTCAAAGTTCTCATTTCTTAGGTACCAT
TTCCTGGTGTTGGCTCCCGTAT

SEQ ID NO. 323
(S2-20 For)
ATACGGGAGCCAACACCATTAAAGTTAATCTTACACGTTTCCGACTTCCA
TTTGAGAGCAGGTGTGACGGAT

SEQ ID NO. 324
(S2-20 Rev)
ATCCGTCACACCTGCTCTCAAATGGAAGTCGGAAACGTGTAAGATTAACT
TTAATGGTGTTGGCTCCCGTAT

SEQ ID NO. 325
(S2-21 For)
ATCCGTCACACCTGCTCTCAAAGGCCTTAGCTCGTAAAACGTAGACGGAC
TCCTTGGTGTTGGCTCCCGTAT

SEQ ID NO. 326
(S2-21 Rev)
ATACGGGAGCCAACACCAAGGAGTCCGTCTACGTTTTACGAGCTAAGGCC
TTTGAGAGCAGGTGTGACGGAT

Leishmania donovani Parasites

SEQ ID NO. 327
(LD-3F)
GATACGGGAGCCAACACCAC-CCGTATCGTTCCCAATGCACT-
CAGAGCAGGTGTGACGGATG

SEQ ID NO. 328
(LD-3R)
CATCCGTCACACCTGCTCTG-AGTGCATTGGGAACGATACGG-
GTGGTGTTGGCTCCCGTATG

SEQ ID NO. 329
(LD-5F)
GATACGGGAGCCAACACCAC-GTTCCCATACAAGTTACTGA-
CAGAGCAGGTGTGACGGATG

SEQ ID NO. 330
(LD-5R)
CATCCGTCACACCTGCTCTG-TCAGTAACTTGTATGGGAAC-
GTGGTGTTGGCTCCCGTATC

Crimean-Congo Hemorrhagic Fever (CCHF) Viruses

SEQ ID NO. 331
(C1-1 F)
ATACGGGAGCCAACACCAATAAAGAGCGGAACTTTTAGAACTGGATAGAC
TCATAGAGCAGGTGTGACGGAT

SEQ ID NO. 332
(C1-1 R)
ATCCGTCACACCTGCTCTATGAGTCTATCCAGTTCTAAAAGTTCCGCTCT
TTATTGGTGTTGGCTCCCGTAT

SEQ ID NO. 333
(C1-1/7 F)
ATACGGGAGCCAACACCATAGTGTTGGGCCAATACGGTAACGTGTCCTTG
GAGAGCAGGTGTGACGGAT (69)

SEQ ID NO. 334
(C1-1/7 R)
ATCCGTCACACCTGCTCTCCAAGGACACGTTACCGTATTGGCCCAACACT
ATGGTGTTGGCTCCCGTAT (69)

SEQ ID NO. 335
(C1-2 F)
ATACGGGAGCCAACACCACTAACTTGTTGCTGATCTTATCCAGAGCAGGT

GTGACGGAT (59)

SEQ ID NO. 336
(C1-2 R)
ATCCGTCACACCTGCTCTGGATAAGATCAGCAACAAGTTAGTGGTGTTGG

CTCCCGTAT (59)

SEQ ID NO. 337
(C1-3 F)
ATACGGGAGCCAACACCAATGAGAGCAAAGATCCCAGGATACACTAATCC

CTGTAGAGCAGGTGTGACGGAT

SEQ ID NO. 338
(C1-3 R)
ATCCGTCACACCTGCTCTACAGGGATTAGTGTATCCTGGGATCTTTGCTC

TCATTGGTGTTGGCTCCCGTAT

SEQ ID NO. 339
(C1-4 F)
ATACGGGAGCCAACACCACCTAGTGTTGAATCTGACCACAAGCTAAGTCT

TCGGAGAGCAGGTGTGACGGAT

SEQ ID NO. 340
(C1-4 R)
ATCCGTCACACCTGCTCTCCGAAGACTTAGCTTGTGGTCAGATTCAACAC

TAGGTGGTGTTGGCTCCCGTAT

SEQ ID NO. 341
(C1-5 F)
ATACGGGAGCCAACACCAAGCACGGAAAGAGGGTCGCCTGATAGCCCGCC

AATCAGAGCAGGTGTGACGGAT

SEQ ID NO. 342
(C1-5 R)
ATCCGTCACACCTGCTCTGATTGGCGGGCTATCAGGCGACCCTCTTTCCG

TGCTTGGTGTTGGCTCCCGTAT

SEQ ID NO. 343
(C1-6 F)
ATACGGGAGCCAACACCAAGAAATGCCAACACAACGACACCGGTAGTGCT

GCCCAGAGCAGGTGTGACGGAT

SEQ ID NO. 344
(C1-6 R)
ATCCGTCACACCTGCTCTGGGCAGCACTACCGGTGTCGTTGTGTTGGCAT

TTCTTGGTGTTGGCTCCCGTAT

SEQ ID NO. 345
(C1-9 F)
ATACGGGAGCCAACACCATGGTGACGGACCTTGAGAGCAAGACCGCTACG

ATTCAGAGCAGGTGTGACGGAT

SEQ ID NO. 346
(C1-9 R)
ATCCGTCACACCTGCTCTGAATCGTAGCGGTCTTGCTCTCAAGGTCCGTC

ACCATGGTGTTGGCTCCCGTAT

SEQ ID NO. 347
(C1-10 F)
ATACGGGAGCCAACACCAGAAGAACACTGCCTAGAATAAGTGGTGCAGGG

CCGTAGAGCAGGTGTGACGGAT

SEQ ID NO. 348
(C1-10 R)
ATCCGTCACACCTGCTCTACGGCCCTGCACCACTTATTCTAGGCAGTGTT

CTTCTGGTGTTGGCTCCCGTAT

SEQ ID NO. 349
(C2-4 F)
ATACGGGAGCCAACACCATTAGGTGGTAGACTGTAGGTTACAGATAGCCG

GGGAGAGCAGGTGTGACGGAT (71)

SEQ ID NO. 350
(C2-4 R)
ATCCGTCACACCTGCTCTCCCCGGCTATCTGTAACCTACAGTCTACCACC

TAATGGTGTTGGCTCCCGTAT (71)

SEQ ID NO. 351
(C2-5 F)
ATACGGGAGCCAACACCATCTGGCGCCGACCCTGTGGATTGCAGTCGCGG

TTACAGAGCAGGTGTGACGGAT

SEQ ID NO. 352
(C2-5 R)
ATCCGTCACACCTGCTCTGTAACCGCGACTGCAATCCACAGGGTCGGCGC

CAGATGGTGTTGGCTCCCGTAT

SEQ ID NO. 353
(C2-6/9 F)
ATACGGGAGCCAACACCATAGTGTTGGGCCAATACGGTAACGTGTCCTTG

GAGAGCAGGTGTGACGGAT (69)

SEQ ID NO. 354
(C2-6/9 R)
ATCCGTCACACCTGCTCTCCAAGGACACGTTACCGTATTGGCCCAACACT

ATGGTGTTGGCTCCCGTAT (69)

SEQ ID NO. 355
(C2-8 F)
ATACGGGAGCCAACACCACAGACACCGAATGAGCAACACAACAACGGGAC

CCGTAGAGCAGGTGTGACGGAT

SEQ ID NO. 356
(C2-8 R)
ATCCGTCACACCTGCTCTACGGGTCCCGTTGTTGTGTTGCTCATTCGGTG

TCTGTGGTGTTGGCTCCCGTAT

SEQ ID NO. 357
(C2-10 F)
ATACGGGAGCCAACACCAGGTATCCGACCGGACACGGCACTACGACCTCT

TTGCAGAGCAGGTGTGACGGAT

SEQ ID NO. 358
(C2-10 R)
ATCCGTCACACCTGCTCTGCAAAGAGGTCGTAGTGCCGTGTCCGGTCGGA

TACCTGGTGTTGGCTCCCGTAT

SEQ ID NO. 359
(C3-3 F)
ATACGGGAGCCAACACCAGGGTTGGTGTAAAGTGGCCAGCCCTTTACGCT

AAGTAGAGCAGGTGTGACGGAT

SEQ ID NO. 360
(C3-3 R)
ATCCGTCACACCTGCTCTACTTAGCGTAAAGGGCTGGCCACTTTACACCA

ACCCTGGTGTTGGCTCCCGTAT

SEQ ID NO. 361
(C3-4 F)
ATACGGGAGCCAACACCACAGCTGACAATAGAAGGATATCCTGGGTACCG
ATGCAGAGCAGGTGTGACGGAT

SEQ ID NO. 362
(C3-4 R)
ATCCGTCACACCTGCTCTGCATCGGTACCCAGGATATCCTTCTATTGTCA
GCTGTGGTGTTGGCTCCCGTAT

SEQ ID NO. 363
(C3-5 F)
ATACGGGAGCCAACACCACTGTGTATAACCCTAACGCTCTATGTTCGTTA
TGCAAGAGCAGGTGTGACGGAT

SEQ ID NO. 364
(C3-5 R)
ATCCGTCACACCTGCTCTTGCATAACGAACATAGAGCGTTAGGGTTATAC
ACAGTGGTGTTGGCTCCCGTAT

SEQ ID NO. 365
(C3-6 F)
ATACGGGAGCCAACACCAGCCCCCGCCTGGTTCCCGCAGGCCGCTCGCGT
CCCGAGAGCAGGTGTGACGGAT

SEQ ID NO. 366
(C3-6 R)
ATCCGTCACACCTGCTCTCGGGACGCGAGCGGCCTGCGGGAACCAGGCGG
GGGCTGGTGTTGGCTCCCGTAT

SEQ ID NO. 367
(C3-7 F)
ATACGGGAGCCAACACCACGGGCGTCACTAGCTCAGACCGTCCCCCGTTG
GTATAGAGCAGGTGTGACGGAT

SEQ ID NO. 368
(C3-7 R)
ATCCGTCACACCTGCTCTATACCAACGGGGACGGTCTGAGCTAGTGACG
CCCGTGGTGTTGGCTCCCGTAT

SEQ ID NO. 369
(C3-8 F)
ATACGGGAGCCAACACCATAGTGTTGGGCCAATACGGTGACGTGTCCTTG
GAGAGCAGGTGTGACGGAT (69)

SEQ ID NO. 370
(C3-8 R)
ATCCGTCACACCTGCTCTCCAAGGACACGTCACCGTATTGGCCCAACACT
ATGGTGTTGGCTCCCGTAT (69)

SEQ ID NO. 371
(C3-9 F)
ATACGGGAGCCAACACCAATGTCCTCGTTACAAGAATATTTCCTGTTACG
CACCAGAGCAGGTGTGACGGAT

SEQ ID NO. 372
(C3-9 R)
ATCCGTCACACCTGCTCTGGTGCGTAACAGGAAATATTCTTGTAACGAGG
ACATTGGTGTTGGCTCCCGTAT

SEQ ID NO. 373
(C4-7/10/5e F)
ATACGGGAGCCAACACCATAGTGTTGGGCCAATACGGTAACGTGTCCTTG
GAGAGCAGGTGTGACGGAT (69)

SEQ ID NO. 374
(C4-7/10/5e R)
ATCCGTCACACCTGCTCTCCAAGGACACGTTACCGTATTGGCCCAACACT
ATGGTGTTGGCTCCCGTAT (69)

SEQ ID NO. 375
(C4e-6 F)
ATACGGGAGCCAACACCAGTCGTGCTCACTGGTCATCAATACGTCGCTCT
GCCTAGAGCAGGTGTGACGGAT

SEQ ID NO. 376
(C4e-6 R)
ATCCGTCACACCTGCTCTAGGCAGAGCGACGTATTGATGACCAGTGAGCA
CGACTGGTGTTGGCTCCCGTAT

SEQ ID NO. 377
(C4e-9 F)
ATACGGGAGCCAACACCAACTCCGGCCCCTCCCATTGCCGTGACGTGATG
GCGCAGAGCAGGTGTGACGGAT

SEQ ID NO. 378
(C4e-9 R)
ATCCGTCACACCTGCTCTGCGCCATCACGTCACGGCAATGGGAGGGGCCG
GAGTTGGTGTTGGCTCCCGTAT

What is claimed is:

1. A synthetic aptamer comprising:
a first polynucleotide;
wherein the first polynucleotide comprises at least 60 nucleotides;
wherein a 3' terminal oligonucleotide of the first polynucleotide is selected from the group consisting of adenine, cytosine and guanine; and
a protein moiety that is operatively coupled to a primary amine group of the 3' terminal oligonucleotide to form a single-stranded polynucleotide-3' protein conjugate.

2. The synthetic aptamer of claim 1, further comprising:
a second polynucleotide hybridized to the first polynucleotide to form a double-stranded polynucleotide-3' protein conjugate;
wherein the double-stranded polynucleotide-3' protein conjugate comprises an overhang consisting of the 3' terminal oligonucleotide of the first polynucleotide and the protein moiety.

3. The synthetic aptamer of claim 2, wherein the second polynucleotide has at least about 70% complementarity to the first polynucleotide.

4. The synthetic aptamer of claim 2, wherein the second polynucleotide has at least about 95% complementarity to the first polynucleotide.

5. The synthetic aptamer of claim 2, wherein the first polynucleotide is selected from at least one of SEQ ID NO: 107.

6. The synthetic aptamer of claim 1, wherein the first polynucleotide is selected from at least one of SEQ ID NO: 107.

7. The synthetic aptamer of claim 1, wherein the protein moiety is selected from the group consisting of a biocidal protein, a phage lysis protein, a protein that recruits the cells of the immune system, a protein that activates the immune system, and a serum stable protein.

8. The synthetic aptamer of claim 1, wherein the protein moiety is selected from the group consisting of Clqrs, Fc, C3b, C4b, C5a, C567, alpha-globulins, beta-globulins, gamma-globulins, serum albumin, and hemoglobin.

9. The synthetic aptamer of claim 1, wherein the aptamer specifically binds to a toxin, and the protein moiety prevents degradation and clearance of said aptamer when administered in vivo.

10. The synthetic aptamer of claim 9, wherein the toxin is selected from the group consisting of bacterial biotoxins, botulinum toxins, cholera toxin, ricin, staphylococcal enterotoxins, plant toxins, insect toxins, arachnid toxins, or reptilian venoms.

11. The synthetic aptamer of claim 1, further comprising:
a biocompatible bifunctional linker operatively coupling the first polynucleotide to the protein moiety.

12. The synthetic aptamer of claim 1, wherein the protein moiety prevents degradation and clearance of said aptamer when administered in vivo.

13. The synthetic aptamer of claim 1, wherein operative coupling of the protein moiety to the primary amine group comprises covalent bonding of the protein moiety to the primary amine group.

14. A nucleic acid-protein conjugate comprising:
a first polynucleotide;
wherein a 3' terminal oligonucleotide of the first polynucleotide is selected from the group consisting of adenine, cytosine and guanine; and
a protein moiety that is operatively coupled to a primary amine group of the 3' terminal oligonucleotide to form a single-stranded nucleic acid-protein conjugate; and
wherein said single-stranded nucleic acid-protein conjugate has a greater in vivo stability relative to the first polynucleotide alone.

15. The nucleic acid-protein conjugate of claim 14, further comprising:
a second polynucleotide hybridized to the first polynucleotide to form a double-stranded nucleic acid-protein conjugate;
wherein the double-stranded nucleic acid-protein conjugate comprises an overhang consisting of the 3' terminal oligonucleotide of the first polynucleotide and the protein moiety.

16. The nucleic acid-protein conjugate of claim 15, wherein the second polynucleotide has at least about 70% complementarity to the first polynucleotide.

17. The nucleic acid-protein conjugate of claim 15, wherein the second polynucleotide has at least about 95% complementarity to the first polynucleotide.

18. The nucleic acid-protein conjugate of claim 14, wherein the protein moiety is selected from the group consisting of a biocidal protein, a phage lysis protein, a protein that recruits the cells of the immune system, a protein that activates the immune system, and a serum stable protein.

19. The nucleic acid-protein conjugate of claim 14, wherein the protein moiety is selected from the group consisting of Clqrs, Fc, C3b, C4b, C5a, C567, alpha-globulins, beta-globulins, gamma-globulins, serum albumin, and hemoglobin.

20. The nucleic acid-protein conjugate of claim 14, wherein operative coupling of the protein moiety to the primary amine group comprises covalent bonding of the protein moiety to the primary amine group.

\* \* \* \* \*